(12) United States Patent
Chiang et al.

(10) Patent No.: US 7,432,057 B2
(45) Date of Patent: Oct. 7, 2008

(54) GENETIC TEST FOR PSE-SUSCEPTIBLE TURKEYS

(75) Inventors: Wen Chiang, Lansing, MI (US); Gale Strasburg, East Lansing, MI (US); John Linz, East Lansing, MI (US)

(73) Assignee: Michigan State University, Lansing, MI (US)

( * ) Notice: Subject to any disclaimer, the term of this patent is extended or adjusted under 35 U.S.C. 154(b) by 52 days.

(21) Appl. No.: 11/044,111

(22) Filed: Jan. 27, 2005

(65) Prior Publication Data

US 2005/0272362 A1    Dec. 8, 2005

Related U.S. Application Data

(60) Provisional application No. 60/540,490, filed on Jan. 30, 2004.

(51) Int. Cl.
  C07H 21/04    (2006.01)
  C12Q 1/68    (2006.01)

(52) U.S. Cl. .................. 435/6; 435/91.1; 435/91.2; 536/23.1; 536/24.3

(58) Field of Classification Search ............... None
See application file for complete search history.

(56) References Cited

U.S. PATENT DOCUMENTS

| | | | |
|---|---|---|---|
| 4,650,764 A | 3/1987 | Temin et al. .............. 435/350 |
| 4,657,760 A | 4/1987 | Kung et al. .............. 424/154.1 |
| 4,683,195 A | 7/1987 | Mullis et al. ................... 435/6 |
| 4,683,202 A | 7/1987 | Mullis et al. ............... 435/91.2 |
| 4,797,368 A | 1/1989 | Carter et al. ............. 435/320.1 |
| 4,861,719 A | 8/1989 | Miller ......................... 435/236 |
| 4,873,191 A | 10/1989 | Wagner et al. ................ 800/25 |
| 4,946,778 A | 8/1990 | Ladner et al. .............. 435/69.6 |
| 4,965,188 A | 10/1990 | Mullis et al. .................... 435/6 |
| 4,980,289 A | 12/1990 | Temin et al. ............. 435/235.1 |
| 5,096,815 A | 3/1992 | Ladner et al. .............. 435/69.1 |
| 5,124,263 A | 6/1992 | Temin et al. ................ 435/349 |
| 5,139,941 A | 8/1992 | Muzycka et al. ........... 435/456 |
| 5,206,344 A | 4/1993 | Katre et al. ................. 530/351 |
| 5,223,409 A | 6/1993 | Ladner et al. .............. 435/69.7 |
| 5,225,212 A | 7/1993 | Martin et al. ............... 424/450 |
| 5,399,346 A | 3/1995 | Anderson et al. ......... 424/93.21 |
| 5,459,127 A | 10/1995 | Felgner et al. ................. 514/7 |
| 5,474,796 A | 12/1995 | Brennan ..................... 427/2.13 |
| 5,538,848 A | 7/1996 | Livak et al. ...................... 435/6 |
| 5,580,859 A | 12/1996 | Felgner et al. ................ 514/44 |
| 5,584,807 A | 12/1996 | McCabe ........................ 604/71 |
| 5,589,466 A | 12/1996 | Felgner et al. ................ 514/44 |
| 5,605,789 A | 2/1997 | Chen et al. .................. 430/567 |
| 5,614,396 A | 3/1997 | Bradley et al. .............. 435/463 |
| 5,618,682 A | 4/1997 | Scheirer ......................... 435/8 |
| 5,652,096 A | 7/1997 | Cimino .......................... 435/6 |
| 5,674,713 A | 10/1997 | McElroy et al. ............ 435/69.7 |
| 5,719,208 A | 2/1998 | Wideman et al. ........... 523/216 |
| 5,733,731 A | 3/1998 | Schatz et al. ................... 435/6 |
| 5,777,324 A | 7/1998 | Hillenkamp ................. 250/288 |
| 5,811,238 A | 9/1998 | Stemmer et al. ................ 435/6 |
| 5,837,458 A | 11/1998 | Minshull et al. ............... 435/6 |
| 5,843,654 A | 12/1998 | Heister et al. .................. 435/6 |
| 5,843,669 A | 12/1998 | Kaiser et al. ................... 435/6 |
| 5,846,717 A | 12/1998 | Brow et al. ..................... 435/6 |
| 5,858,659 A | 1/1999 | Sapalsky et al. ............... 435/6 |
| 5,888,780 A | 3/1999 | Dahlberg et al. ......... 435/91.53 |
| 5,919,626 A | 7/1999 | Shi et al. ........................ 435/6 |
| 5,925,525 A | 7/1999 | Fodor et al. .................... 435/6 |
| 5,928,689 A | 7/1999 | Milkowski et al. ........... 426/56 |
| 5,952,174 A | 9/1999 | Nikiforov et al. .............. 435/6 |
| 5,976,796 A | 11/1999 | Szalay et al. ................... 435/6 |
| 5,985,551 A | 11/1999 | Brennan ........................ 435/6 |
| 5,985,557 A | 11/1999 | Prudent et al. ................. 435/6 |
| 5,994,069 A | 11/1999 | Hall et al. ....................... 435/6 |
| 6,001,311 A | 12/1999 | Brennan ...................... 422/131 |
| 6,001,567 A | 12/1999 | Brow et al. ..................... 435/6 |
| 6,017,696 A | 1/2000 | Heller ............................ 435/6 |
| 6,020,012 A | 2/2000 | Kauffman et al. ........... 426/281 |
| 6,043,031 A | 3/2000 | Köster et al. ................... 435/6 |
| 6,045,996 A | 4/2000 | Cromin et al. ................. 435/6 |
| 6,051,380 A | 4/2000 | Sosnowski et al. ............. 435/6 |
| 6,068,818 A | 5/2000 | Ackley et al. ................ 422/50 |
| 6,074,859 A | 6/2000 | Hirokawa et al. ............ 435/189 |
| 6,080,912 A | 6/2000 | Bremel et al. ................. 800/23 |
| 6,090,543 A | 7/2000 | Prudent et al. ................. 435/6 |

FOREIGN PATENT DOCUMENTS

| | | |
|---|---|---|
| EP | 0 025 949 | 4/1981 |
| EP | 0 178 220 | 4/1986 |

(Continued)

OTHER PUBLICATIONS

Chiang et al. (Gene, vol. 330, pp. 177-184, 2004).*

(Continued)

*Primary Examiner*—Jeanine A Goldberg
(74) *Attorney, Agent, or Firm*—Medlen + Carroll, LLP

(57) ABSTRACT

This invention relates to methods and compounds for the improvement of turkey meat and turkey populations, but not limited to, a genetic screen to select for turkeys that produce a better quality of meat characterized by a higher postmortem pH and better water holding capacity.

19 Claims, 36 Drawing Sheets

FOREIGN PATENT DOCUMENTS

| | | |
|---|---|---|
| EP | 0 185 573 | 6/1986 |
| EP | 0 453 242 | 10/1991 |
| EP | 0 488 528 | 6/1992 |
| WO | WO 84/03564 | 9/1984 |
| WO | WO 89/07150 | 8/1989 |
| WO | WO 90/02806 | 3/1990 |
| WO | WO 90/08832 | 8/1990 |
| WO | WO 91/18088 | 11/1991 |
| WO | WO 92/05263 | 4/1992 |
| WO | WO 93/03367 | 2/1993 |
| WO | WO 93/09239 | 5/1993 |
| WO | WO 94/12649 | 6/1994 |
| WO | WO 94/21807 | 9/1994 |
| WO | WO 94/26914 | 11/1994 |
| WO | WO 94/28152 | 12/1994 |
| WO | WO 94/28938 | 12/1994 |
| WO | WO 95/02697 | 1/1995 |
| WO | WO 95/07358 | 3/1995 |
| WO | WO 95/18863 | 7/1995 |
| WO | WO 95/21931 | 8/1995 |
| WO | WO 96/17823 | 6/1996 |
| WO | WO 96/22378 | 7/1996 |
| WO | WO 96/25508 | 8/1996 |
| WO | WO 99/67641 | 12/1999 |
| WO | WO 00/39587 | 7/2000 |

OTHER PUBLICATIONS

Strasburg (56th Annual Reciprocal Meta Conference, Jun. 15-18, 2003).*

Chiang et al. (J. Diary Science, vol. 84, (Suppl 1), 394, 2001).*

Airey et al.,"Crooked neck dwarf (cm) mutant chicken skeletal muscle cells in low density primary cultures fail to express normal alpha ryanodine receptor and exhibit a partial mutant phenotype," *Dev. Dyn.*, 197:189-202 (1993).

Alvarado, C.Z., A.R. Sams, "The Role of Carcass Chilling Rate in the Development of Pale, Exudative Turkey Pectoralis" *Poultry Science* 81:1365-1370 (2002).

Baker et al.,"The skeletal muscle Ca2+ release channel has an oxidoreductase-like domain," *PNAS, USA*, 99:12155-12160 (2002).

Beard et al.,"Transcription mapping of mouse adenovirus type 1 early region 3," *Virol.*, 75-81 (1990).

Ben-Bassat et al.,"Processing of the initiation methionine from proteins: Properties of the *Escherichia coli* methionine aminopeptidase and its gene structure," *J. Bacteriol.*, 169:751-757 (1987).

Bender et al.,"Evidence that the packaging signal of moloney murine leukemia virus extends into the gag region," *J. Virol.*, 61:1639-1646 (1987).

Bernstein et al., "Gene transfer with retrovirus vectors" *Genet. Eng.*, 7:235 (1985).

Black,"Mechanism of alternative pre-messenger RNA splicing," *Ann. Rev. Biochem.* 72:291-336 (2003).

Bradley et al.,"Formation of germ-line chimaeras from embryo-derived teratocarcinoma cell lines," *Nature* 309:255-258 (1984).

Brinster et al.,"Factors affecting the efficiency of introducing foreign DNA into mice by microinjecting eggs," *PNAS, USA* 82:4438-4442 (1985).

Caldwell and Joyce, "Randomization of Genes by PCR Mutagenesis" *PCR Methods Appl.*, 2:28-33 (1992).

Caruthers et al.,"New chemical methods for synthesizing polynucleotides," *Nucl. Acids Res. Symp. Ser.*, 7:215-233 (1980).

Catterall,"Excitation-contraction coupling in vertebrate skeletal muscle: A tale of two calcium channels," *Cell* 64:871-874 (1991).

Chow and Kempe,"Synthesis of oligodeoxyribonucleotides on silca gel support," *Nucl. Acids Res.*, 9:2807-2817 (1981).

Cole et al., in *Monoclonal Antibodies and Cancer Therapy*, "The EBV-hybridoma technique and its application to human lung cancer," Alan R. Liss, pp. 77-96 (1985).

Cote et al., "Generation of human monoclonal antibodies reactive with cellular antigens," *PNAS, USA* 80:2026-2030 (1983).

Crameri et al., "Improved green fluorescent protein by molecular evolution using DNA shuffling," *Nat. Biotech.*, 14:315-19 (1996).

Crameri, et al., "Molecular evolution of an arsenate detoxification pathway by DNA shuffling," *Nat. Biotech.*, 15:436-38 (1997).

Crea and Horn,"Synthesis of oligonucleotides on cellulose by a phosphotriester method," *Nucl. Acids Res.*, 9:2331-2348 (1980).

Creighton, *Proteins Structures And Molecular Principles*, W H Freeman and Co, New York N.Y. (1983).

Curiel et al., "High-Efficiency Gene Transfer Mediated by Adenovirus Coupled to DNA-Polylysine Complexes," *Hum. Gene Ther.*, 3:147-154 (1992).

Cwirla et al.,"Peptides on phage: A vast library of peptides for identifying ligands," *PNAS, USA* 87:6378-6382 (1990).

Denyer et al.,"HTS approaches to voltagegated ion channel drug discovery," *Drug Discov. Today* 3:323-32 (1998).

Devlin et al.,"Random peptide libraries: a source of specific protein binding molecules," *Science* 249: 404-406 (1990).

deWet et al.,"Firefly luciferase gene: Structure and expression in mammalian cells," *Mol. Cell. Biol.* 7:725-737 (1987).

Eckert and Kunkel, "DNA Polymerase Fidelity and the Polymerase Chain Reaction" *PCR Methods Appl.*, 1:17-24 (1991).

Evans et al.,"Establishment in culture of pluripotential cells from mouse embryos," *Nature* 292:154-156 (1981).

Evans et al.,"An engineered poliovirus chimaera elicits broadly reactive HIV-1 neutralizing antibodies," *Nature* 339:385-388 (1989).

Felgner et al.,"Lipofection:A highly efficient, lipid-mediated DNA-transfection procedure," *PNAS, USA* 84:7413-7417 (1987).

Felgner and Ringold, "Cationic liposome-mediated transfection" *Nature* 337:387-388 (1989).

Freud et al., *Statistical Methods*, Rev. Ed. Acad. Press, San Diego, CA (1997).

Fujii et al.,"Indentification of mutation in porine ryanodine receptor associated with malignant hyperthermia," *Science* 253:448-451 (1991).

Futatsugi et al.,"Tissue-specific and developmentally regulated alternative splicing in mouse skeletal ryanodine receptor mRNA,"*Biochem. J.* 305:373-378 (1995).

Gluzman,"SV40-transformed simian cells support the replication of early SV40 mutants," *Cell* 23:175-182 (1981).

Gossler et al.,"Transgenesis by means of blastocyst-derived embryonic stem cell lines," *PNAS, USA* 83:9065-9069 (1986).

Graham, "Covalently closed circles of human adenovirus DNA are infectious," *EMBO J.*, 3:2917-2922 (1984).

Graham and van der Eb,"A new technique for the assay of infectivity of human adenovirus 5 DNA," *Virol.*, 52:456-467 (1973).

Graham et al., "Characteristics of a human cell line transformed by DNA from human adenovirus type 5" *J. Gen. Virol.*, 36:59 (1977).

Haskell and Bowen,"Efficient production of transgenic cattle by retroviral infection of early embryos," *Mol. Reprod. Dev.*, 40:386-390 (1995).

Hochuli et al.,"New metal chelate absorbent selective for proteins and peptides containing neighbouring histidine residues," *J. Chromatogr.*, 411:177-184 (1987).

Huang et al.,"Vaccinia virus recombinants expressing an 11-kilodalton β-galactosidase fusion protein incorporate active β-galactosidase in virus particles," *J. Virol.*, 62:3855-3861 (1988).

Huse et al., "Generation of a large combinatorial library of the immunoglobulin repertoire in phage lambda," *Science* 246:1275-1281 (1989).

Ike et al., "Solid phase synthesis of polynucleotides. VIII. Synthesis of mixed oligodeoxyribonucleotides by the phosphotriester solid phase method," *Nucl. Acid Res.*, 11:477 (1983).

Inohara et al., "An induced proximity model for NF-κB activation in the Nod1/RICK and RIP signaling pathways" *J. Biol. Chem.* 275:27823-31 (2000).

Itakura et al., "Chemical Synthesis and Application of Oligonucleotides of Mixed Sequence," *Recombinant DNA*, in Walton (ed.), Proceedings of the 3rd Cleveland Symposium on Macromolecules, Elsevier, Amsterdam, pp. 273-289 (1981).

Itakura, et al., "Synthesis and use of synthetic oligonucleotides" *Annu. Rev. Biochem.*, 53:323 (1984).

Itakura et al.,"Expression in *Escherichia coli* of a chemically synthesized gene for the hormone somatostatin," *Science* 198:1056-1062 (1984).

Jaenisch,"Transgenic animals," *Science* 240:1468-1474 (1988).

Jähner et al.,"*De novo* methylation and expression of retroviral genomes during mouse embryogenesis," *Nature* 298:623-628 (1982).

Jähner et al.,"Insertion of the bacterial *gpt* gene into the germ line of mice by retroviral infection," *PNAS, USA* 82:6927-693 (1985).

Jiang et al.,"Smooth muscle tissues express a major dominant negative splice variant of the type 3 Ca2+ release channel (ryanodine receptor)," *J. Biol. Chem.* 278:4763-4769 (2003).

Janenich,"Germ line integration and mendelian transmission of the exogenous moloney leukemia virus," *PNAS, USA* 73:1260-1264 (1976).

Janknecht et al.,"Rapid and efficient purification of native histidine-tagged protein expressed by recombinant vaccinia virus," *PNAS, USA* 88:8972-8976 (1991).

Jurkat-Rott et al.,"Genetics and pathogenesis of malignant hyperthermia," *Muscle & Nerve* 23:4-17 (2000).

Kacian et al.,"A replicating RNA molecule suitable for a detailed analysis of extracellular evolution and replication," *PNAS USA*, 69:3038-3042 (1972).

Kaplitt et al., "Expression of a Functional Foreign Gene in Adult Mammalian Brian following *in Vivo* Transfer via a Herpes Simplex Virus Type 1 Defective Viral Vector," *Mol. Cell. Neurosci.*, 2:320-330 (1991).

Köhler and Milstein,"Continous cultures of fused cells secreting antibody of predefined specificity," *Nature* 256:495-497 (1975).

Kozbor, et al.,"The production of monoclonal antibodies from human lymphocytes," *Immunol. Tod.*, 4:72-79 (1983).

Kuo et al.,"Efficient gene transfer into primary murine lymphocytes obviating the need for drug selection," *Blood* 82:845-852 (1993).

Lai et al.,"Purification and reconstruction of the calcium release channel from skeletal muscle," *Nature* 331:315-319 (1988).

La Salle et al.,"An adenovirus vector for gene transfer into neurons and glia in the brain," *Science* 259:988-990 (1993).

Lebkowski, et al.,"Adeno-associated virus: a vector system for efficient introduction and integration of DNA into a variety of mammalian cell type," *Mol. Cell. Biol.*, 8:3988-3996 (1988).

Leeb and Brenig,"cDNA cloning and squencing of the human ryanodine receptor type 3(RYR3) reveals a novel alternative splice site in the RYR3 gene," *FEBS Lett* 423:367-370 (1998).

Leung et al., "A method for random mutagenesis of a defined DNA segment using a modified polymerase chain reaction," *Technique*, 1:11-15 (1989).

Levrero et al., "Defective and nondefective adenovirus vectors for expressing foreign genes in vitro and in vivo," *Gene* 101:195-202 (1991).

Machey et al.,"Gene transfer fromtargeted liposomes to specific lymphoid cells by electroporation," *PNAS, USA* 85:8027-8031 (1988).

Maniatis, et al.,"Regulation of Inducible and tissue-specific gene expression," *Science* 236:1237-1244 (1987).

Mann et al.,"Construction of a retrovirus packaging mutant and its use to produce helper-free defective retrovirus," *Cell* 33:153-159 (1983).

Markowitz et al.,"A safe packaging line for gene transfer: separating viral genes on two different plasmids," *J. Virol.*, 62:1120-1124 (1988).

Marziali et al.,"cDNA cloning reveals a tissue specific expression of alternative spliced transcripts of the ryanodine receptor type 3 (RyR3) calcium release channel," *FEBS lett.*, 394:76-82 (1996).

Matteucci and Caruthers,"The synthesis of oligodeoxypyrimidines on a polymer support," *Tetrahedron Lett.*, 21:719-722 (1980).

McCartney,"A randombred control population of turkeys," *Poultry Sci.* 43:739-744 (1964).

McCormick,"Human gene therapy: the first round," *BioTechnol.*, 3:689 (1985).

Miller and Rosman,"Improved retroviral vectors for gene transfer and expression," *BioTech.*, 7:980-990 (1992).

Miller et al.,"N-terminal methionine-specific peptidase in *Salmonella typhimurium*," *PNAS, USA* 84:2718-1722 (1990).

Miyatake et al.,"Tissue-specific alternative splicing of mouse brain type ryanodine receptor/calcium release channel mRNA," *FEBS lett.*, 395:123-126 (1996).

Moore and Arnold,"Directed evolution of a *para*-nitrobenzyl esterase for aqueous-organic solvents," *Nat. Biotech.*, 14, 458-67 (1996).

Nardelli et al.,"A chemically defined synthetic vaccine model for HIV-I," *J. Immunol.*, 148:914-920 (1992).

Needleman and Wunsch,"A general method applicable to the search for similarities in the amino acid sequence of two proteins," *J. Mol. Biol.* 48:443-453 (1970).

O'Brien et al.,"Physiological difference between the α and β ryanodine receptors of fish skeletal muscle," *Biophys. J.* 68:471-482 (1995).

Ottini et al.,"α and β isoforms of ryanodine receptor from chicken skeletal muscle are homologues of mammalian RyRI anf RyR3," *Biochem. J.* 315:207-216 (1996).

Owens, C.M. and A.R. Sams, "The Influence of Transportation on Turkey Meat Quality" *Poultry Science* 79:1204-1207 (2000).

Oyamada et al.,"Primary structure and distribution of ryanodine-binding protein isoforms of the bullfrog skeletal muscle," *J. Biol. Chem.* 269:17206-17214 (1994).

Parker et al.,"Targeted gene walking polymerase chain reaction," *Nucleic Acids Res.*, 19:3055-60 (1991).

Pearson and Lipman,"Improved tools for biological sequence comparison," *PNAS, USA)* 85:2444-248 (1988).

Phillips et al.,"The structural organization of the human skeletal muscle ryanodine receptor (RYRI) gene," *Genomics* 34:24-41 (1996).

Pietrzak et al.,"Effect of rapid rigor mortis processes on protein functionality in pectoralis major muscle of domestic turkrys," *J. Anim. Sci.* 75:2106-2116 (1997).

Posnett et al.,"A novel method for producing anti-peptide antibodies," *J. Biol. Chem.*, 263:1719-1725 (1988).

Ritty et al.,A new hincll RFLP for epidermal growth factor (EGF) on chromsome 4, *Nucl. Acids Res.*, 17:5870 (1989).

Roberge et al.,"A strategy for a convergent synthesis of N-linked glycopeptides on a solid support," *Science* 269:202-204 (1995).

Roberts et al.,"Directed evolution of a protein: selection of potent neutrophil elastase inhibitors displayed om M13 fusion phage," *PNAS, USA* 89:2429-2433 (1992).

Robertson et al.,"Germ-line transmission of genes introduced into cultured pluripotential cells by retroviral vector," *Nature* 322:445-448 (1986).

Rose et al.,"Consensus-degenerated hybrid oligonucleotide primers for amplification of distantly related sequences," *Nucl. Acids Res.*, 26:1628-1635 (1998).

Sambrook, et al., *Molecular Cloning: A Laboratory Manual*, 2nd ed., Cold Spring Harbor Laboratory Press, New York (1989) pp. 16.6-16.8.

Sambrook, et al., *Molecular Cloning: A Laboratory Manual*, 2nd ed., Cold Spring Harbor Laboratory Press, New York (1989) pp. 7.39-7.52.

Sambrook, et al., *Molecular Cloning: A Laboratory Manual*, 2nd ed., Cold Spring Harbor Laboratory Press, New York (1989) pp. 9.31-9.58.

Sambuughin et al.,"Single-amino acid deletion in the RyR1 gene, associated with malignant hyperthermia susceptibility and unusual contraction phenotype," *Am. J. Hum. Genet.*, 69:204-208 (2001).

Samulski et al., "Helper-free stocks of recombinant adeno-associated viruses: normal integration does not require viral gene expression," *J. Virol.*, 63:3822-3828 (1989).

Samulski et al., "A recombinant plasmid from which an infectious adeno-associated virus genome can be excised in vitro and its use to study viral replication," *J. Virol.*, 61:3096-3101 (1987).

Sarkar et al., "Restriction-site PCR: A Direct Method of Unknown Sequence Retreival Adjacent to a Known Locus by Using Universal Primers," *PCR Methods Applic.*, 2:318-22 (1993).

Schlienger et al.,"Human immunodeficiency virus type 1 major neutralizing determinant exposed on hepatitis B surface antigen particles is highly immunogenic in primates," *J. Virol.*, 66:2570-2576 (1992).

Schroeder and Neagle,"FLIPR: a new instrument for accurate, high throughput optical screening," *J. Biomol. Screening* 1:75-80 (1996)[abstract only].

Scott et al., "Searching for peptide ligands with an epitope library" *Science* 249:386-390 (1980).

Shapiro and Senapathy,"RNA splice junctions of different classes of eukaryotes:sequences statistics and functional implications in gene expression," *Nucleic Acids Res.*, 15:7155-7174 (1987).

Smith,"The progeny of sexual PCR," *Nature*, 370:324-25 (1994).

Smith et al.,"Single-step purification of polypeptides expressed in *Escherichia coli* as fusions with glutathione *S*-transferase," *Gene* 67:31-40 (1988).

Smith and Waterman,"Comparison of biosequences," *Adv. Appl. Math.* 2: 482-489 (1981).

Stemmer,"DNA shuffling by random fragmentation and reassembly: *in vitro* recombination for molecular evolution," *PNAS, USA*, 91, 10747-51 (1994).

Stemmer,"Rapid evolution of a protein *in vitro* by DNA shuffling," *Nature*, 370:389-91 (1994).

Stewart et al.,"Expression of retroviral vectors in transgenic mice obtained by embryo infection," *EMBO J.*, 6:383-388 (1987).

Stratford-Perricaudet et al., "Widespread long-term gene transfer to mouse skeletal muscles and heart" *J. Clin. Invest.*, 90:626-630 (1992).

Stryer ed., *Biochemistry*, p. 17-21, 2nd ed, WH Freeman and Co., 1981 (cover copy only).

Triglia et al.,"A procedure for *in vitro* amplification of DNA segments that lie outside the boundaries of known sequences," *Nucleic Acids Res.*, 16:8186 (1988).

Ulmer et al.,"Heterlogous protection against influenza by injection of DNA encoding a viral protein," *Science* 259:1745-1748 (1993).

Voss et al.,"The role of enhancers in the regulation of cell-type-specific transcriptional control," *Trends Biochem. Sci.*, 11:287-289, (1986).

Wahl et al.,"Molecular hybridization of immobilized nucleic acids: theoretical concepts and prectical considerations," *Meth. Enzymol.*, 152:399-407 (1987).

Wheeler et al., "A Halothane Test to Detect Turkeys Prone to Developing Pale, Soft and Exudative Meat" *Poultry Science* 78:1634-1638 (1999).

Williams et al.,"Introduction of foreign genes into tissues of living mice by DNA-coated microprojectiles," *PNAS, USA* 88:2726-2730 (1991).

Wilson et al.,"The structure of an antigenic determinant in a protein," *Cell*, 37:767-778 (1984).

Wilson et al.,"Hepatocyte-directed gene transfer in vivo leads to transient improvement of hypercholesterolemia in low density lipoprotein receptor-deficient rabbits," *J. Biol. Chem.*, 267:963-967 (1992).

Wu et al.,"Functional interactions between cytoplasmic domains of the skeletal muscle Ca2+ release channel," 40:25051-25061 (1997).

Wu and Wu,"Receptor-mediated *in vitro* gene transformation by a soluble DNA carrier system," *J. Biol. Chem.*, 262:4429-4432 (1987).

Wu and Wallace,"The ligation amplification reaction (lar)-amplification of specific DNA sequences using sequential rounds of template-dependent ligation," *Genomics*, 4:560-569 (1989).

Wu and Wu,"Receptor-mediated gene delivery and expression *in vivo*," *J. Biol. Chem.*, 263:14621-14624 (1988).

Zhang et al.,"Directed evolution of a fucosidase from a galactosidase by DNA shuffling and screening," *PNAS, USA*, 94:4504-09 (1997).

Zhao and Arnold,"Optimization of DNA shuffling for high fidelity recombination,"*Nuc. Acids. Res.*, 25:1307-08 (1997).

Zorzato, et al.,"Indentification of two ryanodine receptor transcripts in neonatal, slow, and fast-twitch rabbit skeletal muscles," *Biochem Biophys Res Commun*. 203:1725-30 (1994).

US 5,962,233, 10/1999, Livak et al. (withdrawn)

\* cited by examiner

```
                376                                                                     435    Seq. ID No.
PRYR1        ILHQEGHMDD ALSLTRCQQE ESQAARMIYS TAGLYNHFIK GLDSFSGKPR GSGAPAGTAL            1
HRyR1        MLHQEGHMDD ALSLTRCQQE ESQAARMIHS TNGLYNQFIK SLDSFSGKPR GSGPPAGTAL            2
Bfr-αRyR     ILHQEGHMDD ALSLSRSQRE ESQAARMIYS TAGLFNIFIK GLDSLNGKNK PSKP...ISL            3
FαRYR        ILHKEGHMDD ALTVARSQTE EAQAARMIYS TTGLFNQFIK GLDTLSGKNK SANPP...SL            4
TαRyR        ILHQEGHMDD ALSLSRSQGE ESQAARMIYS TAGLYGSFIR SLDALSSRGR GGG-AGNAAL            5
TαRyR-AS81   ILHQEGHMDD ALSLSRSQGE ESQAARMIYS TAGLYGSFIR .......... ..........            6
TαRyR-AS193  ILHQEGHMDD ALSLSRSQGE ESQAARMIYS TAGLYGSFIR G*                                7

436                                                                     495
PRYR1        PLEGVILSLQ DLIGYFEPPS EELQHEEKQS KLRSLRNRQS LFQEEGMLSL VLNCIDRLNV
HRYR1        PIEGVILSLQ DLIIYFEPPS EDLQHEEKQS KLRSLRNRQS LFQEEGMLSM VLNCIDRLNV
Bfr-αRyR     PLDMVVLTLQ DLIGYFQHPE EELQHEEKQT KLRSLKNRQN LFQEEGIISQ VLDCIDRLNV
FαRYR1       PMDTVVLSLQ DLIFYFRPPG HELEHEDKQF KLRSLKNRQN LFQEEGMITL VLDCVDRLNV
TαRyR        PIAAVILSLR DLIAYFRAPH TELQHEQRQN RLRSLRRRQD LFQQEGMISL VLNCIDRLNV
TαRyR-AS81   ........LR DLIAYFRAPH TELQHEQRQN RLRSLRRRQD LFQQEGMISL VLNCIDRLNV 496                                                                     555
PRYR1        YTTAAHFAEF AGEEAAESWK EIVNLLYEIL ASLIRGNRAN CALFSNNLDW LVSKLDRLEA
HRYR1        YTTAAHFAEF AGEEAAESWK EIVNLLYELL ASLIRGNRSN CALFSTNLDW LVSKLDRLEA
Bfr-αRyR     YSTAAHFAEF AGEEAAESWK EIVNLLYELL ASLIRGNRSN CALFSNNLDW VVSKLDRLEA
FαRYR        YNTAAHFSEY AGEEAAESWK EIVNLLYELL ASLIRGNRAN CALFCDNLDW LVSKLDRLEA
TαRyR        YSTAAHFAEF AGEEAAAAWK EIVNLLYELL ASLIRGNRTN CALFSTNLDW LVSKLDRLEA
TαRyR-AS81   YSTAAHFAEF AGEEAAAAWK EIVNLLYELL ASLIRGNRTN CALFSTNLDW LVSKLDRLEA 556                                                                     615
PRYR1        SSGILEVLYC VLIESPEVLN IIQENHIKSI ISLLDKHGRN HKVLDVLCSL CVCNGVAVRS
HRYR1        SSGILEVLYC VLIESPEVLN IIQENHIKSI ISLLDKHGRN HKVLDVLCSL CVCNGVAVRS
Bfr-αRyR     SSGILEVLYC VLIESPEVLN IIKKNHIKSI ISLLDKHGRN HKVLDVLCSL CVCNGVAVRS
FαRYR        SSGILEVLYC VLIESPEVLN IIQENHIKSI ISLLDKHGRN HKVLDVLCSL CVCNGVAVRS
TαRyR        SSGILEVLYC VLIESPEVLN IIQENHIKSI ISLLDKHGRN HKVLDVLCSL CVCNAVAVRS
TαRyR-AS81   SSGILEVLYC VLIESPEVLN IIQENHIKSI ISLLDKHGRN HKVLDVLCSL CVCNAVAVRS
```

FIG 1

| Name | Alternative Splice Junction | Product |
|---|---|---|
| Wild type | exon 12 ...atc cg \| gt....tag \| exon 13 g agc...atc ctc agc ctg...gag \| gt...tag \| exon 14 ggg atg atc...g<br>I  R        S......I  L  S  L......E        G  M  I.....A | Full length |
| AS-81 | exon 12 ...atc cg \| gt....tag \| exon 13 g agc...atc ctc agc ctg...gag \| gt..tag \| exon 14 ggg atg atc...g<br>I  R                              L......E        G  M  I....A | 81-bp deletion Δ1350-1430 |
| AS-193 | exon 12 ...atc cg \| gt....tag \| exon 13 g agc...atc ctc agc ctg...gag \| gt...tag \| exon 14 g gga tga<br>I  R                                                        G  stop | 193-bp deletion Frameshift Δ1350-1542 |

FIG 4

Turkey αRyR, start-#3767 nucleotide sequence
Turkey 5'end Length: 3168  November 18, 2003 16:51

```
   1  atgggtgacg gaggagaggg cgatgtgcag ttcctgagga cggacgatga
  51  ggtggtgctg caatgcacca cgacgctgct gaaggagcag ctgaagctct
 101  gcctggcggc cgaaggcttc gggaaccgcc cgtgcttcct ggagcccacg
 151  tccaacgcac agaatgtgcc ccccGAcCTG GCCgTCTGCT GCTTCGTCTT
 201  GGAGCAGTCG CTGTCAgTCC GAGCGCTGCA GGAGATGTTG GCCAACTGTG
 251  CAGAGAGCGG CaGAGAGTCG TCGCAGGGCG GGGGGCATCg CACGCTGCTC
 301  TATGGACACG CCATCCTGCT GCGGCACTCC CATAgCGGGA TGTACCTGAG
 351  CTGCCTGACC ACCTCCCGCT CCGTCACCGA CAAACTGGCC TTCGATGTGG
 401  GGCTGCAGAA GGACgCAGCG GGGGAGGCCT GTTGGTGGAC GCTGCACCCG
 451  GCGTCGAAGC AGCGCTCAgA GGGGGAAAAG GTGCgAGTGG GGGACGACAT
 501  CATCCTGGTG AGCGTCTCCT cCGAGCGCTA CCTGCACCTC TCGACGGCCA
 551  GCGGGGAGCT GCAGGCGGAC GCCTCCTTCA TGCAGACCCT GTGGAACATG
 601  AACCCCATcT GCTCGGGGGC CGAGGAAGGT TATGTGACGG GGGGCCACGT
 651  GCTGCGTCTG TTCCACGGCC ACATGGATGA GTGCCTCAGC ACCTCCCCCC
 701  CCGAGCAGGG GGACGAGCGC AGCAGCGTGG TGAGCTACGA GGGGGGGGCC
 751  GTCTGCACCC ACGCACGGTC GCTGTGGAGG TTGGAGCCGC TGCGCATCAG
 801  TTGGAGCGGC AGCCACCTCC GCTGGGGGCA GCCCTTCCGG GTTCGTCACG
 851  TGACGTCGGG CCGCTATTTG GCGCTGAGCG AAGAGCGCGG CCTCGTGGTG
 901  GTGGAAGCGG CGGCGGCCGG GACCCGAGCG GCTGCGTTCT GCTTCCGGGC
 951  CTCCAAGGAG AAGCTGGAAG CGGGGACGAA gCGCGATGTG GAGGGGATGG
1001  GACCCCCGGA GATCAAATAT GGGGAGTCGC TGTGCTTCGT GCAGCACGCG
1051  GCCTCGGGGc TGTGGCTCAC CTACGCTGCT GCTGACACCA AGCGCTGCG
1101  CCTGGGGCTG ATGAAACGGA GGCCcAtCCT GCACCAGGAg GCCACATGG
1151  ACGACGCGCT GTCGCTCAGC CGCTCGCAGG GCGAGgAGTC GCAGgCGGCG
```

FIG 6

```
1201  CGgATGATTT ACAGCACGGC GGGGCTCTAC GGGAGCTTCA TCCgGAGCCT

1251  GGACGCGCTG AGCTCTCGTG GCCGTGGCGG CGGTGCGGGG AACGCGGCTC

1301  TGCCCATCGC CGCCGTCATC CTCAGCCTGC GGGATCTGAT CGCTTATTTC

1351  CGCGCCCCGC ACACCGAGCT GCAGCACGAG CAGCGCCAGA ACCGCCTGCG

1401  CTCCCTGCGG CgcCGCCAGG ACCTCTTCCA GCAGGAGGGG ATGATCTCCC

1451  TGGTGCTGAA CTGCATCGAC CGGCTGAACG TGTACAGCAC GGcCGCGCAC

1501  TTCGCCGAGT TCGCCGGGGA GGAGGCGGCG GCCGCcTGGA AGGAGATCGT

1551  CAACCTCCTC TATGAGCTGC TGGCGTCGCT GATCCGGGGG AACCGAACCA

1601  ACTGCGCCCT GTTCTCcACC AACCTGGACT GGCTGGTCAG CAAACTGGAC

1651  CGGCTGGAGG CGTCGTCAGG GATCCTGGAG GTGCTTTACT GcGTCCTGAT

1701  CGAGAGCCCC GAGGtTCTGA ACATCatcca ggagaaccac atcaagtcca 1751  tcatctccct gctggacaaa cacggccgca accataaggt cctgaacgtg 1801  ctctgctctc tgtgtgtctg caatgctgtg gccgttcgtt ccaaccaaaa 1851  tctcatcacc gaaaatctgc tcccgcgacg cgacctcctg ctgcagaccg 1901  ggccggtcag ctacgtcagc agcatccggc caacatcct cctggggacc 1951  cacgagggct ccacgcagta cccacgctgg tacttcgagg tggccgtgga 2001  tcacgtggag cccttcgtga cggcgcagcc cacccacctg cgcgtggggt 2051  gggcgatggc ggagggttac agcccctacc cgggggggggg agagggctgg 2101  ggggcctacg gagccggaga cgacctttat tccttcgcct ttgatgggct 2151  gcacctctgg gccggcgggg ttccgcgggc cgcccccctcc ccccagcagc 2201  acatcctggc ccccggggac gtggtgagct gctgcctgga cctctctgtt 2251  cccaccatct cctcccgcct caacggcagc ccggtgctgg ggatgttcga 2301  gaagttcaat cgcgacgcgc tcttctcccc cgtcgtcagc ttctccgccg 2351  gcgtgcggct gcgcttcctg ctgggggggcc gccacgggga tttccagttc 2401  ctgccccccc ccggttactc ccctgtgcc gaggcgctgc tgccccgcga 2451  gcggctgcgc ctggaaccca tcaaagctta tagggcgac ggccccccgc
```

FIG 6 (cont.)

```
2501  cccactgcct gctcggcccc acaaaggcgc tgccccacac cgccttcacc 2551  ccctgccccg tggacaccgc gcagatcgtt ctgccccccc acctggagcg 2601  catccgggag aagctggcgg agaacatcca tgagctgtgg gcgctgaccc 2651  gcatcgagca gggatggacc tacggcccca tccatgacga tgctgagcag 2701  ctccatccct gcctgctgga tttccacagc ctccccgagc cggagcgcaa 2751  ctacaacctg cagatgtcgg gggagacgct caagacgctg ctggcgctgg 2801  gctgccacgt ggggatggcg gacgagaagg cggaggagaa cctgaggaaa 2851  atcaaactgc ccaaaacgta cacgatgcgc aacggttaca aaccggcccc 2901  gctggacctg gcccacgtgc gcctgacgcc ggcgcagctg acgctggtgg 2951  atcggctggc ggagaacgcg cacaacgtct gggcgcggga ccgcgtgcag 3001  cagggccgga cctacagcat cgtgcaggac attaagaaca agcgcaaccc 3051  ccgcctggtg ccctacaacc tgctggacga gcgcaccaag aagaccaaca 3101  gggacagcct gtgcgaggcg gtgcggaccc tcatcggcta cggctacaac 3151  atcgagccac ctgaccag
```

Note: There is a gap of approximately 1,000-1,500 base pairs between the 5'end and 3'end sequence. We are still working on filling the gap.

α-RyR, 3'-end nucleotide sequence
Length: 10129  January 30, 2004  15:50  Type: N

```
  1  ctgccggcgg tgccgcgcct ggaggaggac gtggtgccgg acgagcggga 51  cgaccccgat gtcatcatga acagcaccac gtactacttc tcggtgcgga 101  tctttgctgg ccaggacccc tcccacgtct gggtgggcag ggtgaccccc 151  gattaccacc agcacgaccc caacttcgac ctgacgcgcg tccgcaccgt 201  caccgtcacc atggggacg acaggggaa cgtgcacgac agcatcagac 251  gcagcagctg ctacatgctg tgggccgggg agttcggctc cgcttccccg 301  cagagccgca gccacagcga cgccgtcatc ggctgcctgg tggacgtggc 351  cacggggctg atgaccttca ccgccaacgg caaggagctc aacaccttct 401  tccaggtgga gcccaacacc aagctgttcc ccgccgtctt cgtgctgccc
```

FIG 6 (cont.)

```
 451   agcagtcagc acgtggtgca gttcgagctg gggaagctga agaacatcct
 501   gccgctgtcg gccgcgctgt tcagcagcga gcgctgcaac ccggagccgc
 551   agtgcccgcc ccggctgtgc atccagcgcc tgaccgccgt cacctggagc
 601   cggatggcgg ccgaggagct gcccgtgagc agcggccggg ccgccgacgg
 651   ccgcggctgg gaggtgcgct gttccgaacc gcgcctgatg atggcgctgc
 701   acattccgga ggagaacaga tgcatggaca tcatggagct gtgggagcgg
 751   caggacctgc tccgcttcca ttggcacacg ctgaagctgt actgcgccgt
 801   gtgcgcgctg ggcaacacgc gggtggcgca cgcgctgtgc agccacgtgg
 851   atccgtcgca gctcctcttc gccatccgca gcccggagct gcccggcccc
 901   ctccgcgccg gttactacga cctgctgctg gccgtgcacc tggagcaggg
 951   cgtccgcgcc cgggcctcca tgagcaccga gttcatcgtc cccatggacg
1001   aggcgtccaa acgcatctcc ctgttccccg ccggcggggg gggcgacgtc
1051   aaagtgcccg gcccccccgg cgtcgggctc agcgcctgcc tccgcccccg
1101   gccgcacttc gccgagccgt gcttcgtgcg gccgcccgac ggcagggcgc
1151   tgctgggtcc ctctatcccg ctgcgggcgc tgggcaggag ggccatcagg
1201   atgctgaggg aggcggtggc gggggggggg ccgcacgccc gggaccccgt
1251   cggcggcggc gtggagttcc agctggtgcc ggtgttgaag ttggtgtcgg
1301   ctctgctggc cgtcggggcg ctgcgggacc cggaggtgcg caaggtgctg
1351   cggatgatcg aacccagggt gttcgggggg ggcgaggagg aggaggagga
1401   ggaggagagg aggaggagga ggaaggccgt ggaggccggc gaggaggagg
1451   aggaggtgga cgaggaggag gaggtagatg aggaggagga cgaggaggag
1501   gaggaggacg ggccggagga agggctgctg CAgATGAAGT TGCCAGaGTC
1551   TGTGAAGCTG cAGaTGTGCA ACcTACTGCA GTTCTTCTGC GACCAgGAgC
1601   TGCAGCACCG CGTGGAAgCG ATCGTCGCCT TCTCGGAgCG CCACGTGGAg
1651   CGGCTGCAGC GCGACCAGAg GCGGCGCTAC GGGCGGCTGA TGGGGGCCGT
1701   GACGATGAGC GCGGCTGAGA CCGCGAgGAg AACCAGGGAG TTCCGGTcCC
1751   CCCCCCAGGA ACAGATCAAC ATGCTGCTGC AGTACAAGGG gGGGGCGGAC
1801   GAGGAGGACT GCCCCGTGCC CCCCGACATC CGCGGGGAGC TGCTGCAATT
```

FIG 6 (cont.)

```
1851   CCACAGCGAC CTGCTGGCGC ACTGCGGCAT CGAGCTGCAG GGCGAGGAGG
1901   AGGAGGAGGA GGAAGACGCG TCGCTGCGGC AGCGGCTGCT GGCCTTGGTG
1951   CAACGCGTGG TGGGGAGGCA GCAGAAGGAG GAGGAGGAGG AGGAGGCGAC
2001   GTCCCCAGAG CCCCCCGTGC CACGCACCCT GCAGGAGCTG ATCTCGCACA
2051   CCATGGTTCA CTGGGCTCAG GAATCCTTCA TCCAGAGCCC CGAGCTGGTT
2101   CGCTCCATGT TCAGCCTGCT GCACCGGCAG TACGACGGGC TGGGGGAGCT
2151   GGTGCGGGCG CTGCCCAAGG CTTACACCAT CAGCGCCCAC TCGGTGCCCG
2201   ACACCACGGC GCTGCTCgAG TGCCTGGGGC AgATCCGCTC GCTGCTCATC
2251   GtACAgATGG GGCCCGAGGA GGAgAACCTc ATGATaCAgA gCATcGGGAA
2301   CATcATGAAc aACAAAGTCT TCTACCAGCA CCCCAACCTG ATGCGGGCGC
2351   TGGGGATGCA CGAGACGGTC ATGCAGGTGA TGGTGAGCGT GCTGGGCGGC
2401   GGCGAGACCA AGGAGATCCG CTTCCCCAAA ATGGTCACCA ACTGCTGCCG
2451   CTTCCTCTGC TACTTCTGCC GCATCAGCCG CCAGAACCAG CGCTCCATGT
2501   TCGACCACCT GGGCTACCTG CTGGAGAACA GCAGCATCGG CCTGGGCATG
2551   CAGGGCTCCA CCCCATTGGA CGTGGCGGCC GCTTCTGTCA TCGACAACAA
2601   CGAGTTGGCA CTGGCACTGA AGGAGCAGGA CCTGGAGAAG GTGGTGACGT
2651   ACCTGGCGAG CTGCGGGCTG CAGAGCTGCC CCATGCTGCT GTCCAAGGGT
2701   TACCCCGACA TCGGCTGGAA CCCCTGCGGG GGGGAGCGCT ACCTCGACTT
2751   CCTGCGCTTC GCCGTCTTCG TCAACGGTGA GAGCGTGGAG GAAAACGCCA
2801   ACGTGGTGGT CCGGCTGCTG ATCCGACGCC CCGAATGCTT CGGGCCGGCG
2851   CTGCGCGGGG AGGGGGGCAG CGGGCTGCTG GCCGcCATCG AGGACGCCAT
2901   TAAGATCAGC GAGGATCCGG CACGGGACGG cCCCACCGTC AAGAAGGAGA
2951   GGAGGAGGGA GATATTCGGG GCAGAGGAGC CCCACGAGGA GAACCGCGTc
3001   CACCTGGGCA ACGCCATCAT GTCCTTCTAC GCCGCCTCgA TCGACCTGCT
3051   GGGCCGCTGC GCCCCCGAAA TGCACCTGAT CCAAGCAGGG AAGGGCGAAG
3101   CGCTGCGGAT CCGCGCCATC CTGCGCTCCC TGGTGCCACT GGATGACCTG
3151   GTGGGCGTCA TCAGCCTCCC CCTGCAGATC CCGGCCTTCG GGAAAGACGG
3201   GAACGTGGTG CAGCCCCGCA TGGCTGCCAG CTTTGTGCCG GACCACAAGG
3251   CTCCCATGGT GCTTTTCCTG GACCGCGTTT ACGGCATCGA GACGCAGCAG
```

FIG 6 (cont.)

```
3301  TTCCTGCTCC ACGTGCTGGA GGTCGGCTTC CTGCCCGACA TGAGACCGGC
3351  CGCCTCCCTC GACACGGCGG CGTTCAGCAC GACGAAGATG GCGCTGGCGC
3401  TgAACCGCTA CCTGTGCGTG CCGGTGTTgC CGCTCATCAC CAAATGCGCG
3451  CCGCTGTTTG CCGGCACGGA GCACCGCGCC ATCATGGTGG ACTCCATGCT
3501  GCACACCATC TACCGCCTGT CGCGCGgCCG CGCGCTCACC AAGGCGCAGC
3551  GCGACGCCAT CGAGGAGTGC CTGATGGCTC TGTGCCGGTA CATCCGGCCC
3601  TCCATGCTGC AGCACCTCCT GCGCCGCCTC GTCTTCGACG TCCCCATCCT
3651  CAACGAGTTC GCCAAGATGC CGCTCAAGCT GCTGACCAAC CACTACGAGC
3701  GCTGCTGGAA GTATTACTGC CTGCCCAGCG GGTGGCCCAA CTACGGGGTC
3751  AGCTCCGAGG AGGAGCTGCA CCTGACCCGG AAGCTCTTCT GGGGCATCTT
3801  TGAGTCCCTG GCTCACAAGA AGTTCGACCC CGAGCTGTAC AAGCTGGCCA
3851  TGCCGTGCCT CTGCGCCATC GCGGGCGCCC TGCCCCCCGA CTACGTGGAC
3901  GCCAGCTACT CCTCCAAGAC CGAGAAGAAG GCGTCGGTGG ACGCCGAGGG
3951  CAACTTCGAC CCCAAACCCG TCGAGACCCT CAACGTCATC ATCCCTGAGA
4001  AGTTGGACGG CTTCATCAAC AAATACGCCG AGTTCACCCA CGAGAAGTGG
4051  GCGTTCGATA AGATCCAGAA CAACTGGACC TACGGGGAGA CGGTGGACGA
4101  GGAGGCCAAG ACCCACCCCA TgcTGCGGCC CTACAAGACC TTCTCAGAgA
4151  AGGACAAGGA AATTTACCGG TGGCCCATCA AGGAGTCGCT GAAGGCGATG
4201  CTGGCGTGGG AGTGGATGGT GGAAAAGGCG CGGGAGGGCG ACGAGGAGAA
4251  GGCGGAGAAG AAGAAAACGC GGAAGATCTC GCAGTCGGCG CAGGCCACCT
4301  ACGACCCCAG CCATGGCTAC AACCCGCAGC CCGTGGACCT CTCGGGGGTG
4351  ACGCTGTCCC GAGAGCTGCA GGCGATGGCG GAGCAGCTGG CTGAGAACTA
4401  CCACAACACG TGGGGCCGCA AGAAGAAGCA GGAGCTGGAG GCCAAAGGGG
4451  GGGGCTCCCA CCCCCTGCTG GTGCCCTACG ACACGCTGAC GGCCAAGgAG
4501  AAGGCGCGCG ACCGCGAGAA GGCGCAGGAG CTGCTCAAGT TCCTGCAGCT
4551  GAACGGCTAC GCCGTCACAC GGGGGCTGAA GGACATGGAG TTGGACACGT
4601  CtTCCATCGA GAAGCGCTTC GCCTACGGCT TCCTGCAGCA GCTGCTGCGG
4651  TGGATGGACA TCTCCCAGGA GTTCATCGCC CACCTGGAGG CTGTGGTGAG
```

FIG 6 (cont.)

```
4701  CAGCGGCCGC GTGGAGAAGT CGCCCCACGA ACAGGAGATC AAATTCTTTG
4751  CCAAGATCCT GCTGCCCCTC ATCAACCAGT ACTTCCACAA CCACTGCCTC
4801  TACTTCCtcT CcACCCCCGC CAAAGTGCTG GGCAGCGGCG GCCACGCGTC
4851  CAACAAGGAG AAGGAGATGA TCACCAGCCT GTTCTGCAAG CTGGCCGCGC
4901  TCGTCCGCCA CCGCGTCACT CTCTTTGGCA CCGACGCGCC GGCCGTGGTC
4951  AACTGCCTCC ACATCCTGGC ACGGTCGCTG GACGCCAGGA CGGTGATGAA
5001  GTCCGGCCCC GAGATCGTGA AGGCCGGGCT GCGCTCCTTC TTCGAGAGCG
5051  CCTCGGAGGA CATCGAGAAG ATGGTGGAGA ACCTGAAGCT GGGCAaGGTG
5101  ACGCAGAGCC GCACGCAGGT GAAGGGGGTG GCCCAGAACA TCAACTACAC
5151  CACGGTGGCT CTGCTGCCCG TCCTCACGTC GCTCTTCGAG CACATCGCCC
5201  AGCACCAGTT TGGGGACGAC GTCATCCTGG ACGATGTCCA GGTCTCGTGT
5251  TACCGCATCC TGTGCAGCAT TTACTCCTTG GGCACCACCA GGAACCCCTA
5301  CGTGGAAAGG CAGCGCCCGG CGCTGGGGGA GTGCCTGGCC CGGCTGGCGG
5351  CCGCCATGCC TGTGGCCTTC CTGGAGCCGC GGCTCAATGA GTTCAACCCC
5401  TGCTCCGTCT ACAGCACCAA GTCGCCCCGC GAGCGTGCCA ACCCCCATCT
5451  TTGGGGCACT GCAGACCCCC ACCCCATCTT TGGGACCCCA ACACCAGTCC
5501  TGGGGCTGCC GAGCCACGTG GAGGAGATGT GCCCCGACAT CCCGGACCTG
5551  GAGCGCCTGA TGAAGGACAT CGGGGGGCTG GCGGAGTCgG GCGCTCGCTA
5601  CACGGAGATG CCCCACGTCA TCGAGGTGAC GCTGCCCATG CTGTGCAATT
5651  ATTTGcCCCG CTGGTGGGAG CGCGGgCCGG ACAGcAgcCC CCAgGGGCCG
5701  TGGGCCACGG cCGTCACCGG GCAGCACCTG AACGCCCTGG cTGGGAAACA
5751  TcCTGCGCAT CGTGGtCAAC AACCTGGGCA TcGACgAGGC GTCCTGGATG
5801  AAACGCtgGC AGTGTTCGCT CAGCCCATCG TCAGCAAGGC GAAGCCGGAG
5851  CTGCTGCGCA CCCACTTCAT CCCCACGATG GAGAAGCTGA GAAGCGGGC
5901  AGGGAAGGTG GTGTCGGAGG AGGAGCAGCT GCGCATGGAG GCGAAGGCGG
5951  AGGCCGAGGA CGCCGAGCTG CTCATCCGCG ACGAGTTCTC CGTGCTCTGC
6001  CGCGACCTCT ACGCCCTGTA CCCTCTGCTC ATCCGCTACG TCGACAACAG
6051  CCGGGCCAAG TGGCTGACGG AGCCCAACGC GGACGCGGAG GAGCTGTTCC
6101  GCATGGTGGG AGAGGTCTTC ATCTACTGGT CCAAATCCCA CAACTTTAAG
```

```
6151  CGCGAGGAGC AGAACTTTGT GGTGCAGAAT GAGATCAACA ACATGTCCTT
6201  CCTGACGGCC GACAGCAAGA GCAAGATGGC CAAGTCCGGA GACGGCCAGG
6251  GCGGTGGCTC GGAGCAGGAG CGCACCAAGA AGAAGCGCCG CGGCGACCGT
6301  TACTCCATCC ACACCTCCCT GATCGTGGCC ACCCTGAAGA AGATGCTGCC
6351  CATCGGCCTC AACATGTGCT CCCCCACCGA CCAGGAGCTC ATCAGCCTGG
6401  CCAAGAGCCG CTACGCCCTG AAGGACACGG ATGAAGAGGT GCAGGAGTGC
6451  CTGAACAACA ACCTGCACCT GCAGGGCAAG TGTGAGAACT CGTCGGCCAT
6501  GCGCTGGCAG CTGGCTCTGT ATCGCGCCAT GGCCGGCAGG GCTGAGGACT
6551  CTGACAGCCC AGAGAAAATC GTGAGACGAG TGCAGGAGGT GTCAGCAGTG
6601  CTGTATCACC TGGAGCAGAC GGAGCACCCC TACAAGTCCA AGAAGGCGGT
6651  GTGGCACAAA CTGCTCTCCA GCAGCGGCG CCGCGCCGTG GTCGCCTGTT
6701  TCCGAATGAC GCCGCTCTAC AACCTGCCCA GGCATCGCGC CTGCAATATG
6751  TTCCTGGAGG CCTACAAGCT GCTGTGGTTG GTGACGGAGG AGCATCCCTT
6801  CGAGGACCGC ATGATTGACG ACCTGGCGAA ATCAGGGGAG GAGGAGGAGG
6851  AGGAGGAAGA GGAGAAGGAC AAGAAGCCAG ACCCGCTGCA TCAGCTCATC
6901  CTGCACTTCA GCCGCACGGC GCTGACCGAG AAAAGCAAGT GGAGAAGGA
6951  TCACCTGTAC ATGGCGTACG CGGGTATCAT GGCCAAGAGC TGTCACATTG
7001  AAgAAGGGAA TGAAGAGGAG AAGGAGGAGA AGAAGGAGGA GGAGGACCCG
7051  GAGGATTCGT TTGAGGAGAA GGAGATGGAG AAGCAGAAGC TGCTGTACCA
7101  GCAGTCGCGG CTGCACACGA GGGGAGCAGC TGAGATGGTG CTGCAGATGA
7151  TCAGCGCCTG CAAAGGGGAG CGGGGGGAGA TGGTTTCCTC CACGCTGAAG
7201  TTGGGGATCT CCATCCTCAA CGGGGGAAAC GCCGATGTGC AGCAGAAAAT
7251  GTTGGATTAC CTGAAGGAGA AACGTGAGAT CGGATTCTTC CAAAGCGTCC
7301  AGGCGCTGAT GCAGACCTGC AGCGTCCTGG ACCTGAACGC CTTTGAGCGG
7351  CAGAACAAAG CGGAGGGGCT GGGGATGGTG ACGGAGGAGG GGACGATCAT
7401  CAGCCGTGAG AACGGGGAGA AGGTGATGTC GGATGATGAG TTCACGCAGG
7451  Atctgttccg gctgctgcag ctgctgtgcg aggggcacaa caacgacttc
7501  cagaattacc tccgcacgca gacgggcaac accaccacca tcaacatcat
```

FIG 6 (cont.)

```
7551  catctgcacc gtggattacc tgctgcgcct gcaggagtcc atcagcgatt
7601  tctattggta ttactcgggg aaggacgtca tcgacgagca gggaaagcgc
7651  aacttctcca aggccatggc tgtggccaag caggtcttca acagcctcac
7701  cgagtacatc cagggtccgt gcacggggaa ccagcagagc ctggctcaca
7751  gccgcctgtg ggacgccgtg gtcggattcc tgcacgtctt cgcacacatg
7801  atgaagaagt tggcacagga ctccagccag atcgggctgc tgaaggagct
7851  gctggacctg cagaaggaca tggtggtgat gctgctgtcc ctgctggaag
7901  gcaatgtggt gaacgggacg atcgcacggc aggtggtgga catgccggtg
7951  gagtcgtcca gcaacgtcac catgatcctg aagttcttcg atatgttcct
8001  gaagctgcgc gacatcgtgg cctccgacgc cttccgcgat tacgtgacgg
8051  acccgcgggg gctcatctcc aaaaaggact tccagaaggc catggacagc
8101  cagaagcagt acgagccgtc cgaggtgcag ttcctgctct cgtgctcgga
8151  ggcggacgag aacgagatga tcgacgtgga ggcgttcgtc gggcgctccc
8201  aggagccggc tcgcgacatc ggcttcaacg tggcggtgct gctgaccaac
8251  ctggccgagc acgtccccca cgaccagagg ctgcgcacct ttttggagca
8301  ggccgccagc atcctggagt atttccggcc gtttctgggc cgcatcgaga
8351  tcatgggagc ggcgcggcgc atcgagcgcc tctacttcga gatcagcgcg
8401  gccaacaagg cgcagtggga gatgccccag gaggatggaa aggaggtggt
8451  ggaggaaccg cagaaggagg aggaggaggc ggcggccgaa accgaaaagg
8501  ccgatacgga gaatggagag aagggcgatg ggggcgcaga ggggggtccg
8551  gaggtggaga ccccgaaaa gcagcagaag gcgtcgcccc ccgggagcg
8601  taaagagccc ccccgcccg aagggccctt cgagttctgg acggagttgg
8651  aggtgcagag ggtgaagttc ctgaactacc tctcccgcaa cttctacaat
8701  ctccgcttcc tggcgctctt cctcgccttc gccatcaact tcATCCTCCT
8751  CTTCTATAAG GTGTCGGAGC GGCCGCCGGG AATGGAGGAG GCGGAGTTGG
8801  AGGGGTCGGG AATGGCGGCG GTGTTGGACG GGATCGGAGA CTTCGGGGAC
8851  GGCGGGGACG GGACGGCGG GGACGGGGAG GAGGAGCCGA GCGTGGTGTA
8901  TTACTGCCTG GAGGAGAGCA CGGGCTACAT GCAGCCCGCC CTGCGCGCCC
8951  TGGCCGTGGC TCACACCATC GTGGCGTTCC TCTGCATCAT CGGCTACAAC
```

```
9001   TGCCTCAAGA TCCCCCTGGT GATCTTTAAG CGGGAGAAGG AGGTGGCCCG
9051   GCGCCTGGAG TTCTCAGGGC TGTACATCAC TGAGCAGCCG CCGGACGACG
9101   ACGTGAAGGG GCAGTGGGAT CGCCTGGTCC TGAATGCGCA GTCCTTCCcT
9151   AGCAATTACT GGGACAAGTT CGTCAAGAGA AAGGTGCTGG AGAAATATGG
9201   GGACATTTAT GGCCGTGAGC GCATCGCGGA GCTGCTGGGG ATGGAGCTCT
9251   cCAGcCTCGA AATCGGGGCA CGGGGGGAGA GGAAACCCCC CCCCGACAAC
9301   TcCGTGCTCA CCTGGATCAC CTTCATCGAT ATCCGCTATC AGATCTGGAA
9351   GTTTGGGGTC ATCTTCACTG ATAACTCGtT CCTGtACCTG ACGTGGtATA
9401   TGGGCATGTC CCTTCTGGgC CAcTACAaCA ACTTCTTCTT CGTTGCACAC
9451   CTCcTGGACA TCGCCATGGG GGTgAAGACG CTGCGCACCA TCCTGTCCTC
9501   CGTCACCCAT AATGGAAGCA ACCTGGCCAT GACCGTGGGG CTGCTGGCTG
9551   TCGTCGTGTA TCTTTACACC GTCGTGGCCT TCAACTTCTT CCGGAAATTC
9601   TaCAATAAGA GTGAAGATGA GGATGAGCCC GACATGAAAT GCGACGACAT
9651   GATGACGTGC TACCTGTTCC ATATGTACGT GGGGGTCCGC GCCGGGGGGG
9701   GCATCGGGGA TGAAATCGAG GACCCGGCTG GGGATGAATA CGAGCTGTAC
9751   CGCGTGGTCT TCGACATCAC CTTCTTCTTC TTCGTCATCG TCATCCTGCT
9801   GGCCATCATC CAAGGTCTGA TCATCGACGC CTTCGGGGAG CTGCGGGACC
9851   AGCAGGAGCA GGTGAAGGAG GACATGGAGA CAAAATGCTT CATCTGTGGC
9901   ATTGGCAGCG ATTACTTTGA CACGACGCCC CACGGCTTCG AGACCCACAC
9951   GTTGGAGGAG CACAATTTGG CAAATTACAT GTTCTTCCTG ATGTATCTGA
10001  TCAATAAGGA TGAGACGGAG CACACGGGGC AGGAGTCCTA cGTATGGAAG
10051  ATGTACCAGG AGCGcTGCtg ggatttcttc cctgccggtg actgcttccg
10101  caagcagtac gaggaccagc tgggctgac
```

FIG 6 (cont.)

TRANSLATE of: turkey αRyR 5'end check: 7813 from: 1 to: 3168
OH-H, αRyR, start-#3767; amino acid sequence
Turkey 5'end  Length: 1056  November 18, 2003 16:51

```
   1  MGDGGEGDVQ FLRTDDEVVL QCTTTLLKEQ LKLCLAAEGF GNRPCFLEPT
  51  SNAQNVPPDL AVCCFVLEQS LSVRALQEML ANCAESGRES SQGGGHRTLL
 101  YGHAILLRHS HSGMYLSCLT TSRSVTDKLA FDVGLQKDAA GEACWWTLHP
 151  ASKQRSEGEK VRVGDDIILV SVSSERYLHL STASGELQAD ASFMQTLWNM
 201  NPICSGAEEG YVTGGHVLRL FHGHMDECLS TSPPEQGDER SSVVSYEGGA
 251  VCTHARSLWR LEPLRISWSG SHLRWGQPFR VRHVTSGRYL ALSEERGLVV
 301  VEAAAAGTRA AAFCFRASKE KLEAGTKRDV EGMGPPEIKY GESLCFVQHA
 351  ASGLWLTYAA ADTKALRLGL MKRRPILHQE GHMDDALSLS RSQGEESQAA
 401  RMIYSTAGLY GSFIRSLDAL SSRGRGGGAG NAALPIAAVI LSLRDLIAYF
 451  RAPHTELQHE QRQNRLRSLR RRQDLFQQEG MISLVLNCID RLNVYSTAAH
 501  FAEFAGEEAA AAWKEIVNLL YELLASLIRG NRTNCALFST NLDWLVSKLD
 551  RLEASSGILE VLYCVLIESP EVLNIIQENH IKSIISLLDK HGRNHKVLNV
 601  LCSLCVCNAV AVRSNQNLIT ENLLPRRDLL LQTGPVSYVS SIRPNILLGT
 651  HEGSTQYPRW YFEVAVDHVE PFVTAQPTHL RVGWAMAEGY SPYPGGGEGW
 701  GAYGAGDDLY SFAFDGLHLW AGGVPRAAPS PQQHILAPGD VVSCCLDLSV
 751  PTISSRLNGS PVLGMFEKFN RDALFSPVVS FSAGVRLRFL LGGRHGDFQF
 801  LPPPGYSPCA EALLPRERLR LEPIKAYRGD GPPPHCLLGP TKALPHTAFT
 851  PCPVDTAQIV LPPHLERIRE KLAENIHELW ALTRIEQGWT YGPIHDDAEQ
 901  LHPCLLDFHS LPEPERNYNL QMSGETLKTL LALGCHVGMA DEKAEENLRK
 951  IKLPKTYTMR NGYKPAPLDL AHVRLTPAQL TLVDRLAENA HNVWARDRVQ
1001  QGRTYSIVQD IKNKRNPRLV PYNLLDERTK KTNRDSLCEA VRTLIGYGYN
1051  IEPPDQ
```

TRANSLATE of: αRyR-3'end check: 3572 from: 1 to: 10129
αRyR, 3'-end amino acid sequence
αRyR 3'-end Length: 3376  January 30, 2004 15:51  Type: P  Check: 7207

```
   1  LPAVPRLEED VVPDERDDPD VIMNSTTYYF SVRIFAGQDP SHVWVGRVTP

51  DYHQHDPNFD LTRVRTVTVT MGDDRGNVHD SIRRSSCYML WAGEFGSASP

101  QSRSHSDAVI GCLVDVATGL MTFTANGKEL NTFFQVEPNT KLFPAVFVLP

151  SSQHVVQFEL GKLKNILPLS AALFSSERCN PEPQCPPRLC IQRLTAVTWS

201  RMAAEELPVS SGRAADGRGW EVRCSEPRLM MALHIPEENR CMDIMELWER

251  QDLLRFHWHT LKLYCAVCAL GNTRVAHALC SHVDPSQLLF AIRSPELPGP

301  LRAGYYDLLL AVHLEQGVRA RASMSTEFIV PMDEASKRIS LFPAGGGGDV

351  KVPGPPGVGL SACLRPRPHF AEPCFVRPPD GRALLGPSIP LRALGRRAIR

401  MLREAVAGGG PHARDPVGGG VEFQLVPVLK LVSALLAVGA LRDPEVRKVL

451  RMIEPRVFGG GEEEEEEEER RRRRKAVEAG EEEEEVDEEE EVDEEEDEEE

501  EEDGPEEGLL QMKLPESVKL QMCNLLQFFC DQELQHRVEA IVAFSERHVE

551  RLQRDQRRRY GRLMGAVTMS AAETARRTRE FRSPPQEQIN MLLQYKGGAD

601  EEDCPVPPDI RGELLQFHSD LLAHCGIELQ GEEEEEEEDA SLRQRLLALV

651  QRVVGRQQKE EEEEEATSPE PPVPRTLQEL ISHTMVHWAQ ESFIQSPELV

701  RSMFSLLHRQ YDGLGELVRA LPKAYTISAH SVPDTTALLE CLGQIRSLLI

751  VQMGPEEENL MIQSIGNIMN NKVFYQHPNL MRALGMHETV MQVMVSVLGG

801  GETKEIRFPK MVTNCCRFLC YFCRISRQNQ RSMFDHLGYL LENSSIGLGM

851  QGSTPLDVAA ASVIDNNELA LALKEQDLEK VVTYLASCGL QSCPMLLSKG

901  YPDIGWNPCG GERYLDFLRF AVFVNGESVE ENANVVVRLL IRRPECFGPA

951  LRGEGGSGLL AAIEDAIKIS EDPARDGPTV KKERRREIFG AEEPHEENRV

1001  HLGNAIMSFY AASIDLLGRC APEMHLIQAG KGEALRIRAI LRSLVPLDDL

1051  VGVISLPLQI PAFGKDGNVV QPRMAASFVP DHKAPMVLFL DRVYGIETQQ

1101  FLLHVLEVGF LPDMRPAASL DTAAFSTTKM ALALNRYLCV PVLPLITKCA

1151  PLFAGTEHRA IMVDSMLHTI YRLSRGRALT KAQRDAIEEC LMALCRYIRP

1201  SMLQHLLRRL VFDVPILNEF AKMPLKLLTN HYERCWKYYC LPSGWPNYGV

1251  SSEEELHLTR KLFWGIFESL AHKKFDPELY KLAMPCLCAI AGALPPDYVD
```

FIG 6 (cont.)

```
1301  ASYSSKTEKK ASVDAEGNFD PKPVETLNVI IPEKLDGFIN KYAEFTHEKW
1351  AFDKIQNNWT YGETVDEEAK THPMLRPYKT FSEKDKEIYR WPIKESLKAM
1401  LAWEWMVEKA REGDEEKAEK KKTRKISQSA QATYDPSHGY NPQPVDLSGV
1451  TLSRELQAMA EQLAENYHNT WGRKKKQELE AKGGGSHPLL VPYDTLTAKE
1501  KARDREKAQE LLKFLQLNGY AVTRGLKDME LDTSSIEKRF AYGFLQQLLR
1551  WMDISQEFIA HLEAVVSSGR VEKSPHEQEI KFFAKILLPL INQYFHNHCL
1601  YFLSTPAKVL GSGGHASNKE KEMITSLFCK LAALVRHRVT LFGTDAPAVV
1651  NCLHILARSL DARTVMKSGP EIVKAGLRSF FESASEDIEK MVENLKLGKV
1701  TQSRTQVKGV AQNINYTTVA LLPVLTSLFE HIAQHQFGDD VILDDVQVSC
1751  YRILCSIYSL GTTRNPYVER QRPALGECLA RLAAAMPVAF LEPRLNEFNP
1801  CSVYSTKSPR ERANPHLWGT ADPHPIFGTP TPVLGLPSHV EEMCPDIPDL
1851  ERLMKDIGGL AESGARYTEM PHVIEVTLPM LCNYLPRWWE RGPDSSPQGP
1901  WATAVTGQHL NALAGKHPAH RGQQPGHRRG VLDETLAVFA QPIVSKAKPE
1951  LLRTHFIPTM EKLKKRAGKV VSEEEQLRME AKAEAEDAEL LIRDEFSVLC
2001  RDLYALYPLL IRYVDNSRAK WLTEPNADAE ELFRMVGEVF IYWSKSHNFK
2051  REEQNFVVQN EINNMSFLTA DSKSKMAKSG DGQGGGSEQE RTKKKRRGDR
2101  YSIHTSLIVA TLKKMLPIGL NMCSPTDQEL ISLAKSRYAL KDTDEEVQEC
2151  LNNNLHLQGK CENSSAMRWQ LALYRAMAGR AEDSDSPEKI VRRVQEVSAV
2201  LYHLEQTEHP YKSKKAVWHK LLSKQRRRAV VACFRMTPLY NLPRHRACNM
2251  FLEAYKLLWL VTEEHPFEDR MIDDLAKSGE EEEEEEEEKD KKPDPLHQLI
2301  LHFSRTALTE KSKLEKDHLY MAYAGIMAKS CHIEEGNEEE KEEKKEEEDP
2351  EDSFEEKEME KQKLLYQQSR LHTRGAAEMV LQMISACKGE RGEMVSSTLK
2401  LGISILNGGN ADVQQKMLDY LKEKREIGFF QSVQALMQTC SVLDLNAFER
2451  QNKAEGLGMV TEEGTIISRE NGEKVMSDDE FTQDLFRLLQ LLCEGHNNDF
2501  QNYLRTQTGN TTTINIIICT VDYLLRLQES ISDFYWYYSG KDVIDEQGKR
2551  NFSKAMAVAK QVFNSLTEYI QGPCTGNQQS LAHSRLWDAV VGFLHVFAHM
2601  MKKLAQDSSQ IGLLKELLDL QKDMVVMLLS LLEGNVVNGT IARQVVDMPV
2651  ESSSNVTMIL KFFDMFLKLR DIVASDAFRD YVTDPRGLIS KKDFQKAMDS
2701  QKQYEPSEVQ FLLSCSEADE NEMIDVEAFV GRSQEPARDI GFNVAVLLTN
```

FIG 6 (cont.)

```
2751    LAEHVPHDQR  LRTFLEQAAS  ILEYFRPFLG  RIEIMGAARR  IERLYFEISA

2801    ANKAQWEMPQ  EDGKEVVEEP  QKEEEEAAAE  TEKADTENGE  KGDGGAEGGP

2851    EVETPEKQQK  ASPPRERKEP  PPPEGAFEFW  TELEVQRVKF  LNYLSRNFYN

2901    LRFLALFLAF  AINFILLFYK  VSERPPGMEE  AELEGSGMAA  VLDGIGDFGD

2951    GGDGDGGDGE  EEPSVVYYCL  EESTGYMQPA  LRALAVAHTI  VAFLCIIGYN

3001    CLKIPLVIFK  REKEVARRLE  FSGLYITEQP  PDDDVKGQWD  RLVLNAQSFP

3051    SNYWDKFVKR  KVLEKYGDIY  GRERIAELLG  MELSSLEIGA  RGERKPPPDN

3101    SVLTWITFID  IRYQIWKFGV  IFTDNSFLYL  TWYMGMSLLG  HYNNFFFVAH

3151    LLDIAMGVKT  LRTILSSVTH  NGSNLAMTVG  LLAVVVYLYT  VVAFNFFRKF

3201    YNKSEDEDEP  DMKCDDMMTC  YLFHMYVGVR  AGGGIGDEIE  DPAGDEYELY

3251    RVVFDITFFF  FVIVILLAII  QGLIIDAFGE  LRDQQEQVKE  DMETKCFICG

3301    IGSDYFDTTP  HGFETHTLEE  HNLANYMFFL  MYLINKDETE  HTGQESYVWK

3351    MYQERCWDFF  PAGDCFRKQY  EDQLG*

Note: "*" represents the stop codon.
```

FIG 6 (cont.)

Turkey OH-H, β-RyR: entire coding region (Nucleotide sequence)
    Turkey β-Total  Length: 14620  August 27, 2001 18:12

```
   1  ATGGCTGAAG GGGGTGAAGG AGGAGAAGAT GAAATACAGT TCCTACGAAC
  51  TGATGACGAA GTAGTACTTC AGTGTGTTTC CAGTATTCAC AAAGAACAAA
 101  GGAAGTTTTG CTTGGCAGCT GAGGGACTTG GAAATCGCTT GTGCTTTTTG
 151  GAACCAACGT CAgAAGCTAA ATATGTTCCT CCAGACCTTT GCATCTGTAA
 201  CTTTGTCCTT GAACAGTCTC TGTCTGTAAG AGCCCTTCAA GAGATGCTGA
 251  CCAACACAGG GGATAATGCC AGTGAAGGGG CAGCTCAAGG TGGTCACAGA
 301  ACTTTGCTGT ATGGCCATGC TATACTACTT CGACATTCAT TCAgTGAAAT
 351  GTATTTAACT TGCTTAACAT CATCAAGATC CCAGACTGAT AAACTTGCAT
 401  TTGATGTGGG ACTACGAGAA AATGCAGCAG GTGAGGCATG CTGGTGGACG
 451  ATACACCCTG CTTCTAAACA AGATCAgAA GGAGAAAAAG TTCGAATAGG
 501  TGATGATCTT ATCCTGGTTA GTGTGTCCTC TGAAAGATAC CTGCATCTCT
 551  CCATGTCAAA TGGAAGTATT CAGGTGGACG CCTcCTTCAT GCAGACACTT
 601  TGGAATGTAC ATCCTACATG CTCAGGAAGC AATATTACAG AAGGATATCT
 651  TCTTGGTGGG CATGTAGTAC GTTTTTTCCA TGGTCATGAT GAGTGTTTGA
 701  CAaTTCCTTC TACAGATCAG AATGATTCAC AGCAGAAGAA AGTACTTTAT
 751  GAAACTGGAG GAGCAGGTGT TCGAGCGAGA TCTTTGTGGA GAGTAGAACC
 801  CCTTCGAATA AGTTGGAGCG GAAGTAACAT CAGATGGGGA CAGCCTTTCC
 851  GTCTTCGACA TATAACAACA GGAATGTACT TGGCTTTGAA TGATGATGAA
 901  GGTCTTGTAA TGTTGGACAG AGAAAAGTCA GACACAACAT CTTCTGCTTT
 951  TTGTTTCAGA GCATCAAAGG AACTAAAAGA AAAGCAGGAT TCTACTCTTA
1001  AACGTGACAT TGATGGAATG GGAGTCCCAG AAATAAAATA CGGTGATTCA
1051  GTCTGTTTTG TTCAACATGT AGCCAGTGCC TTATGGCTGA CTTATAAAGC
1101  ACCAGATGCT AAATCAGCAC GCTTAGGGCT CCTGAAAAGA AAGGTTATAT
1151  TACACCAGGA AGGTCATATG GATGATGGTC TAACCTTACA AAGATGTCAA
1201  CATGAAGAAT CACAGGCTGC TCGAATCATT CGCAATACTA CAAGCTTATT
1251  CAGCCAGTTT ATAAGTGGGA ACAACAGAAC ACTATCACCC ATTGCCCTGC
1301  CTGTTGAGGA GATGGCTCAg ACTCTGCAAG ACCTGATCAA GTaCTTCCAg
```

FIG 7

```
1351  CCTCCTGGAG AAGACCTGGA ACATGAGGAT AAGCAAAACA AGCTTCGGTC
1401  CCTCAAAAAC AGACAAAACC TATTCAAAGA TGAGGGAATG CTGGCACTAG
1451  TTTTGAATTG CATCGATCGT TTAAATGACT ACAACAGTGC AGCTCATTTT
1501  GCAGAAATTG CAAGAGAAGA AAATAGTACA GCATGGAAAG AAATTTTAAA
1551  TCTCCTTTAT GAACTGCTTG CTGCTCTCAT TCGTGGCAAC AGAAACAATT
1601  GTACTCAGTT CTCCAGTAAC CTTGATTGGC TAATAAGCAA ATTGGACAGA
1651  CTGGAATCTT CCTCAGGTAT TTTGGAAGTG TTGCACTGTA TCTTGATTGA
1701  AAGTCCAGAA GCTTTAAATG TGATAGCTGA GGAGCATATA AAATCTATTA
1751  TTTCACTGTT GGACAAGCAT GGGCGCAATT ACAAGGTTCT TGATGTGCTT
1801  TGCTCTCTTT GTGTGTGTAA TGGAGTTGCA GTTCGTGCCA ATCAAAACTT
1851  gATCTGtGAC AATCTACTGC CAAGAAGAGA CTTACTTTtG CAAACACGTT
1901  TgATTAATGA TGTGACAAGc aTAAGGCCAA ACATATTTTT GGGTGTTGCT
1951  GAGGGCTCTG CACAATACAA GAAGTGGTAC TTTGAATTAA TAATTGATCA
2001  GGTTGATCCA TTCTTGACGG CAGAACCCAC CCATTTACGG GTTGGGTGGG
2051  CTTCTACTTC AGGTTATGCC CCTTATCCTG GAGGTGGAGA AGGATGGGGT
2101  GGCAATGGCG TTGGAGATGA CCTATATTCC TTTGGTTTTG ATGGCCTTCA
2151  TCTGTGGTCT GGTCGTGTAC CCAGAGCTGT GGCATCTGTC AATCAACATT
2201  TGCTGTCATC TGATGATGTA GTTAGCTGCT GCTTGGATTT AGGTGTGCCC
2251  AGCATTTCAT TCCGCATTAA TGGTCAGCCT GTACAAGGAA TGTTTGAGAA
2301  CTTCTGTACT GAAGGGTTTT TCTTCCCTGT TGTAAGCTTA TCAGCAGGTG
2351  TAAAAGCTCG TTTCTTACTG GGTGGACGTC ATGGAGAGTT TAAATTTCTG
2401  CCTCCTGCTG GCTATGCTCC CTGTTATGAA gCCTTGCTTC CAAAAGAAAA
2451  GATGAAATTG GAACCAGTGA AGAATATAA GAgAGATTCT GATGGAgTGA
2501  GAGATTTGCT GGGTACgACA CAATTCCTCT cCCAAGCTTC ATTTATACCT
2551  TGtCCTATAg ACACCAGTCA gAtTGCTCTT CCTTTTCATC TTGAAAAgAT
2601  CAgGGATAaa cTAGCAGaAA AtATCCATGA ACTGTGGGgA ATgAATAAaA
2651  TAGAgCTGGG CTGGACAtAT GGCaAGATac ggGATgATAA TAAAAGGcAT
2701  CATCCTTGTC TTGTGGAAtT cTCAAaGTta CCTgAGacAg AgaAGAATtA
```

FIG 7 (cont.)

```
2751  TaATCtaCAA ATGTCAACAg AAACCCTcaa AACGCtTTTG GCCCtTGgAT
2801  GTCACAtTGT TCATGCTAAT CCAGCAGcTG aGGAAGATCT TAAAAaAGTC
2851  AAGCTTCCTA AAAATTATAT CATGTCAAAT GGTTATAAAC CTGCCCCTCT
2901  TGATCTTTCT GAAGTGAAAT TGTTACCTTC TCAAGAATTT CTAGTTGACA
2951  AACTAGCAGA AAATGCACAT AATGTCTGGG CAAAAGACAG AATAAAGCAA
3001  GGATGGACCT ATGGCATTCA GCAGGATCTT AAGAACAAAC GTAATCCTCG
3051  GCTAGTGCCA TATGCATTAC TAGATGAACG TACTAAAAAA TCAAACAGAG
3101  ATAGCCTCCG TGAAGCTGTT AGGACATTTG CAGGCTATGG TTATAATATT
3151  GAGCCACCTG ACCAAGAAAT AGCTGACCAA ACATTGGAAA AGTCAGCAT
3201  TGACAAGATA CGTTTTTTCA GAGTAGAACA GTCTTATGCA GTGAAGTCTG
3251  GAAAGTGGTA TTTTGAATTT GAAGCTGTAA CAGGTGGAGA TATGCGTGTT
3301  GGCTGGGCCA GGCCAGGCTG TCGACCTGAC ATTGAACTGG GAGCTGATGA
3351  CCAAGCATTT GTTTTTGAAG GAAGCAAAGG CCAGCGTTGG CATCAAGGCA
3401  GTGGGTTTTT TGGACGAAGT TGGCAACCGG GAGATGTGGT TGGATGCATG
3451  ATAAACTTGG ATGACAAATC AATTATCTTT ACTCTGAATG GAGAGTTGCT
3501  TATAACCAGT AAAGGTTCAG AACTTGCATT TGCTGACTTT GGAATAGAAA
3551  GTGGTTTTGT TCCAATTTGC TCACTGGGTC TAGCTCAGAT TGGACGTATG
3601  AACCTTGGAA TGGATGCCAG TACATTCAAG TATTATACCA TGTGTGGTCT
3651  TCAAGAAGGT TTTGAACCTT TTGCAGTGAA CATGAACCGA GATGTCGCTA
3701  TGTGGTTTAG TAAACGCTTA CCAACATTTG TTAATGTGCC AAAAAATCAT
3751  CCTCACATAG AGATATGGAG AATTGATGGA ACCATTGAGA GTCCACCTCG
3801  GTTAAAAGTT ACTCACAAAA CACTTGGTAC ACAAACAGC AATTCTGATA
3851  TGATATATTG TCGTTTGAGT ATGCCCATTG AGTTCCGTTC ATCATTCAAC
3901  TTTGGCGTGG GTGTGGAAAA TGCCTCATCT GATGCTCTTC AAAAACGAAA
3951  ACACAGCCAA GAATTTCCTG CTTCTTCTAC CACATATTTT TATTCCTTAC
4001  GGATATTTGC TGGCCAAGAC CCATCTTCTG TCtGGGTTGG TTGGGTAACA
4051  CCAGACTATC ATTTTTACAG TGAGAATTTT GACATAAATA AAAACTGTAC
4101  AGTGACAGTT ACTTTAGGAG ATGAGAGAGG CAGGGTTCAT GAAAGTGTGA
4151  AGCGCAGTAA TTGCTATATG GTTTGGGGAG GAGATATAAC TGCTAATTCT
```

FIG 7 (cont.)

```
4201  CAGAGaTCAG GTCGCAGTAA TGTTGATTTA GAAATTGGAT GCTTTGTTGA
4251  CCTGGCTACT GGAATGTTGT CATTCACTGC CAATGGAAAA GAGCTTGGCA
4301  CTTGTTATCA GGTTGAACCA AACACAAAAC TTCTTCCTGC AGCTTTTGTA
4351  CAGCCTACAA GCACTAACTT AATTCAGTTT GAACTTGGTA AATTAAAGAA
4401  TACCATGCCG TTATCAGCAG CAATTTTTAA AAGTGAGGAA AGAAATCCTG
4451  TTCCTCAGTG TCCCCCTCGC CTTGATGTGC AAACAATTAC ACCTGTTTTA
4501  TGGAGTAGGA TGCCTAACAG CTTTCTAAAA GTAGAAACAG AGCGCGTGAG
4551  TGAACGTCAT GGCTGGGTTG TGCAGTGTTT GGAACCACTG CAGATGATGG
4601  CACTTCATAT CCCAGAGGAG AACAGATGTG TGGATATTTT GGAACTATGT
4651  GAACAAGAAG ATTTGATGAA GTTTCACTAT CACACTTTAA AACTTTATAG
4701  CTCAGTTTGT GCTCTAGGTA ACACTAGAGT TGCTTATGCA CTTTGTAGCC
4751  ATGTAGATAT ATCTCAGTTA TTTTACACAA TAGATAATCA GTATTTACCT
4801  GGACTCCTAC GTTCTGGATT CTATGACTTG CTCATTAGTA TTCATTTGGA
4851  CCATGCCAAG CAAGCCAAGC TCATGATGAA CAATGAATTT ATTATTCCAG
4901  TTACAGAGGA AACTCGAACT ATTAAATTAT ATCCTGATGA AACAAAGAAG
4951  CATGGTTTAC CCGGAGTAGG GCTTAGCACT TGTCTCAAAC CAAGCTTTAA
5001  TTTTTCTACT CCTTGCTTTA TTGTGACCTC GGaaGAACAT CAGACATCCA
5051  GCCCAGAAAT TCCCCTTGaC ACACTTAAAT CCAAAGCGAT AAGTATGCTG
5101  ACAGAGGCGG TaCAGTGCAG TGGTTCTCAT ATACGAGATC CTGTTGGAGG
5151  ACATATTGCA TTCCAGTTTG TTCCTGTTCT TAAACTCATA GCAACATTGC
5201  TTATAATGGG AGTTTTTGAT GATGATGATG TGAAGCAGGT GTTAATCCTC
5251  ATTGATCCCA ATGTCTTTGG AGATAACAAG GAAGAAACAG AAGAGAGGAC
5301  AGAGAAGGAA GAAGTTACAC AAGTTGAAGA AAAAGCTGTA GAAGCTGGAG
5351  AAAAGGCAGT AAAAGAAACA AAAACACCTA CAAAGGGCTT ATTGCAGACA
5401  AGATTACCAG AATCTGGTAA GCTTCAGATG TGCCACTTAC TCAATTATTT
5451  CTGTGACTGC GAGCTGCAAC ATAGAGTGGA AGCGATTGtA TCATTTGCAG
5501  aCCACTATGT ATCAAAACTG CAATATAATC AGAAGTACAG GTATAATGAA
5551  CTCATGCAAG CCTTGGACAT GTCTGCTGcT TTGaCTGCCA AGAAGACTAA
```

FIG 7 (cont.)

```
5601  GGaATTTCGA TCTCCTCCAC AAGAACAGAT TAATATGCTG CTGAATTTTC
5651  AACTGGGAGA GGATTGTCCC TGTCCAGAAG AGATTCGGGA TGAACTATAT
5701  GACTTCCATG ATGATCTTCT AATTCACTGT GGTATTCCAC TAGAAGAGGA
5751  GGAAGAGGAA GAGGAAGATT CCTCCTTGAC TGGCAAGCTT CGTTCATTAA
5801  TATACAAAAT CAAAGGTCCA CCAAAACCAG AAAAAATAGA GCCCAGAGAA
5851  GAAGAAGATA AATCGCCTAC TACACTGAAG GAACTCATAT CCCAAACTAT
5901  GGTGCGCTGG TCCCAGGAAG ATCAGATTCA AGATCCAGAA TTGGTTCGGA
5951  TTATGTACAC TCTGCTGCGT AGGCAATATG ATAGCATTGG TGAGCTACTT
6001  CAAGCTCTGA GGAAAGCATA CACTATTAGT GCTGGCTCTG TGAAGGATAC
6051  CATTAATCTG CTTGCTGCAC TGGGCCAGAT TCGCTCACTT CTCAGTGTAA
6101  GAATGGGAAA AGAAGAGGAA CTGCTAATGA TTAATGGATT AGGAGATATC
6151  ATGAACAACA AGGtTTTTTA TCAGCATCCT AACTTAATGA GAGTCTTGGG
6201  CATGCATGAG ACAGTTATGG ATGTGATGGT GAATGTGCTT GGAGGAGATA
6251  AATCTCAGAT CGTTTTTCCT AAGATGGTGG CAAGCTGTTG TCGATTTCTG
6301  TGCTACTTCT GTCGAATTAG TCGTCAAAAC CAAAAAGCCA TGTTTGAGCA
6351  TCTCAGTTAC TTACTGGAAA ACAGCAGCGT TGGGTTGGCA TTTCCTTCAA
6401  TGAGAGGTTC GACACCACTT GATGTTGCAG CAGCCTCTGT AATGGACAAC
6451  AATGAGCTTG CACTAGCACT GGAAGAACCA GATCTTGATA AAGTTGTTAC
6501  TTACCTGGCA GGTTGGGGCC TGCAGAGATG TCCAGTGTTG CTAGCTAAAG
6551  GATATCCAGA CATTGGGTGG AATCCAATAG AGGGTGAACG TTACCTGTCA
6601  TTCCTAAGAT TGCAGTTTT TGTTAACAGT GAAAGTGTTG AAGAAAATGC
6651  AAGTGTTGTT GTAAAGCTTC TTATTCGACG ACCAGAGTGC TTTGGACCAG
6701  AGCTTAGAGG AGAAGGAGGA AATGGATTGC TGGCAGCTAT GCAAGAAGCT
6751  ATACGGATCT CAGAGAATCC TTCTCGTGAC CTTCCCTCAC AAGGATATAA
6801  GAGAGAAGGT GATGAAGAGG AGGAGGAGGA GGAGATCGTA CACATGGGCA
6851  ATGCAATCAT GTCATTTTAC TCTGCTCTCA TAGATTTACT TGGACGCTGT
6901  GCACCAGAAA TGCACCTTAT TCAAAGTGGA AAAGGTGAAG CTATTCGAAT
6951  CAGATCAATC CTTCGATCTC TAGTGCCAAC TGAAGATTTG GTTGGGATTA
7001  TAAGTATACC ACTAAAGCTG TCAACAGTTA ACAAAGATGG CACTGTAAAT
```

FIG 7 (cont.)

```
7051  GAGCCAGACA TGTCTGCAAA TTTCTGTCCT GATCATAAGG CACCAATGGT
7101  ACTCTTTTTG GACCGTGTGT ATGGCATTAA GGACCAAAGC TTCCTCCTTC
7151  ACCTACTTGA AGTTGGATTT TTACCAGATT tAAgAGCTTC TGCCTcTCTG
7201  GATACAGTTT CTCTAAGTAC cACAGAAGCA GCTCTTGCAC TAAaCaGATA
7251  TATTTGCTCA GCTGtGTTTC CGTTACTCAA AAGATGTGCT CCCCTCTTTT
7301  CTGGAACAGA ACATCATGCC TCTCTTGTTG ACTCCATGCT TCACACAATA
7351  TATAGGTTAT CCAAAGGACG TTCCCTTACA AAAGCACAAC GAGACACTAT
7401  TGAAGAATGC CTGCTTGCTA TCTGCCACCA CTTACGTCCC TCTATGCTCC
7451  AACAGCTATT GAGAAGGCTA GTTTTTGATG TGCCCTTACT CAATGAATAC
7501  TGTAAAATGC CACTCAAGCT TCTGACAAAT CACTATGAAC AGTGTTGGAA
7551  ATATTATTGT CTACCTTCAG GAATGGGAAG CTATGGAATT GCAGCAGAAG
7601  ATGAATTACA TTTAACTGAA AAACTTTTTT GGGGAATATT TGATTCCTTG
7651  TCTCATAAGA AGTATGATCC AGAGCTCTTT AGAATGGCCT TGCCCTGCCT
7701  AAGTGCTATA GCTGGGGCTT TGCCTCCTGA TTATTTAGAT ACACGAATTA
7751  GATCAACATT GGAAAAGCAG ACCTCAGTGG ATCCAGAAGG AAATTTTGAT
7801  CCCAAACCCA TCAACACAGC AAACCTTGTA CTTCCTGAAA AGCTGGAGTA
7851  TATTGTCAGC AAATATGCTG AGCATTCTCA TGATAAATGG GCTTTTGATA
7901  AGACTAATAA TGGGTGGAAA TACGGTGTTT CACTGGATGA AAATACAAAG
7951  ACTCATCCAT TAATAAGACC TTTCAAAACT TTAACTGAGA AGGAAAAAGA
8001  AATTTATCGT TGGCCTGTGA GAGAATCCCT GAAAACCATG TTGGCCATGG
8051  GGTGGAGCCT CGAAAGGACC AAGGAAGGGG GCGAAGGAAT GTTACATCAG
8101  CGTGAAAATG AAAAGCTCCG CAGCATATCT CAGTCTAGCC AGGGAAATGG
8151  ATATAGCCCA GCACCACTTG ATCTCACTAA CGTGGTACTT TCTAGGGAAC
8201  TTCAGGGAAT GGTTGAGGTA ATGGCAGAAA ACTACCATAA TATATGGGCC
8251  AAAAAGAAGA AAATGGAGTT GGAAAGCAAA GGTGGAGGCA GTCATCCTTT
8301  ATTGGTACCT TACGACACAT TGACAGCCAA GGAGAAATCA CGGGACCGTG
8351  AAAAGGCACA AGAGCTGTTT AAATTCCTTC AAGTGAATGG CATAATCATA
8401  TCTCGGGGTC TGAATGACAT GGATTTGGAT GCTTCATCCA TGGAAAAGAG
```

FIG 7 (cont.)

```
8451  GTTTGCCTTT AAGTTTCTGA AGAAAATTTT AAAATATGTT GACTCTGCTC
8501  AAGAGTTCAT TGCACATTTG GAAGCCATTG TTACTAGTGG AAAAACTGAA
8551  AAATCCCCGC ATGACCAAGA AATAAAATTC TTTGCCAAAG TTCTTTTACC
8601  ATTAGTTGAT CAATACTTTA CAAATCACTG CTTGTACTTC CTGTCTTCTC
8651  CAACAAAAAC ACTCAGTAGC AGTGGATATG CATCAAATAA GGAAAAGGAA
8701  ATGGTAGCAA GCCTGTTCTG CAAACTAGCT GCTCTTGTTA GACATAGGAT
8751  CTCAATTTTT GGTAGTGATT CTACAACAAT GGTGAGCTGC CTGCACATCT
8801  TAGCTCAGTC TCTGGAtACT CGAACTGTTA TGAAATCAGG ATCTGAGCTA
8851  GTTAAAGCTG GACTACGTGC TTTTTTTGAA AATGCAGCTG AAGATCTGGA
8901  AAAAACTTCA GAAAATCTTA AACTTGGAAA ATTTACACAT TCACGAACAC
8951  AAATCAAAGG TGTTTCACAG AACATCAATT ATACTACAGT AGCATTGCTA
9001  CCTGTCTTGA CGTCAATTTT TGAGCATATT TCACAGTATC ATTTTGGAGT
9051  TGATTTACTT CTGGGTGATG TACAAGTTTC ATGTTACAGA ATTCTTTGTA
9101  GCCTCTATTC TCTTGGGACT GGGAAGAACA TCTACGTTGA AAGGCAACGT
9151  CCTGCACTTG GTGAATGCTT AGCATCTTTT GCAGCAGCCA TTCCAGTAGC
9201  ATTCCTTGAA CCTTCTCTCA ACCACTACAA CCCATTGTCT GTCTTCAACA
9251  CAAAAGTGC AAGAGAAAGA GCAATTTTAG GTATGCCTGA TACAGTAGAG
9301  GAAATGTGTC CAGAAATCCC TCAGCTGGAT GGACTAATAA AGGAAATTAA
9351  TAATTTAGCA GAGTCTGGAG CAAGGTATAC TGAAATGCCT CACGTAATTG
9401  AGGTTATCTT ACCCATGCTG TGCAATTATT TGTCCTACTG GTGGGAACGA
9451  GGGTCTGAGA GTGTTCCTGA AAGTGCTGGC CCTTGCTGTA CGATGATAAC
9501  ATCTGAGCAT CTGAGCATCA TTCTGGGAAA TATTCTGAAA ATCATTAACA
9551  CCAATCTGGG AATAGATGAA GCATCTTGGA TGAAAAGAAT TGCAGTTTAT
9601  GCTCAACCTA TCATCAGCAA AGCCAGACCT GATCTGCTGA AAACTCACTT
9651  TATTCCAACA CTGGAGAAAT TGAAGAAGAA AGCTATAAAG ATTGTGATGG
9701  AAGAGGAGCA ACTGAGAGCA GACAGTAAAA GTGACACTCA AGAAGCTGAG
9751  CTACTTATTC TCGATGAGTT TGCTGTTCTT TGTAGAGACC TCTATGCCTT
9801  CTATCCAATG CTGATACGTT ACGTAGACAA CAACAGAGCC AACTGGCTAA
9851  AGAAACCAGA TGCAGATTCT GATGAACTGT TTCGAATGGT AGCTGAAGTT
```

FIG 7 (cont.)

```
9901   TTTATCCTGT GGTGCAAGTC ACATAATTTC AAAAGAGAAG AACAAAATTT
9951   TGTCATACAG AATGAAATCA ACAATTTGGC ATTTTTAACA GGAGATACCA
10001  AAAGCAAGAT GTCTAAAGCC ATGCAAGTAA AGTCTGGAGG TCAAGATCAA
10051  GAGAGAAAGA AATCAAAACG CAGGGGGGAT TTGTACTCCA TACAAACATC
10101  CTTGATTGTA GCTGCACTTA AAAAGATGCT TCCTATTGGC TTGAATATGT
10151  GTACTCCAGG AGATCAAGAG CTCATCTCAT TGGCTAAGAC TAGATATAGC
10201  CATAAGGACA CTGATGAAGA AGTCAAAGAG CATATaCGTA ACAAtTTACA
10251  TcTGCAGGAA AAGTCTGATG ATCCAGCTGT GAAATGGCAG TTAAATCTAT
10301  ATAAAGACAT TCTGAAGAGT GATGAGCCTC CTGACCCTGA GAAAAATGTG
10351  GAACGTGTGC AGAGGATATC AGCTGCTCTG TATCATCTGG ACCAGGTTGA
10401  ACAACCACTG AGATCAAAGA AAGCTGTTTG CACAAACTT CTGTCAAAAC
10451  AACGCAAAAG AGCTGTTGTT GCTTGTTTTA GAATGGCGCC GTTATACAAC
10501  TTACCCAGGC ACCGTTCTAT TAACCTCTTC CTCCATGGCT ATCAGAACTA
10551  TTGGATAGAA ACAGAGGAAT ATTCATTTGA GGAGAAACTA GTTCAGGATT
10601  TGGCTACGTC TCCAAAAAAA GAGGAAGAAG AAGAGGAAGA TACAGAGAAA
10651  GAACAACCTG aCCCaCTTCA TCAGATTATC CTCTATTTTA GTCGCAATGC
10701  TCTCACAGAG AGGAGCAAAC TAGAAGATGA TCCCTTATAT ATTGCCTATG
10751  CTGCCATGAT GGCAAAGAGC TGTCAGGAAG AAGAAGAAGA GGAGGAGGAA
10801  GACAAAGAGA AGACATTTGA GGAGAAAGAA ATGGAAAAGC AGAGAACTCT
10851  TTATCAGCAA GCTCGCTTAC ATGATCGTGG AGCTGCTGAG ATGGTCCTTC
10901  AGATGATCAG TGCAAGCAAA GGTCATACAG GACCCATGGT TGTTGAAACA
10951  CTAAAACTTG GTATTGCTAT TCTAAATGGT GGGAATACAA TAGTTCAACA
11001  GAAAATGCTA GACTACTTGA AGGAGAAAAA GGATGCTGGA TTCTTTCAAA
11051  GTCTTTCTGG TTTGATGCAG TCCTGCAGTG TTCTTGACTT GAATGCGTTT
11101  GAGAGACAAA ATAAAGCAGA AGGCCTGGGA ATGGTTACTG AAGAAGGAAC
11151  TCTCATCGTA CGTGAGCGTG GTGAAAAAGT GTTGCAGCAT GATGAATTTA
11201  CTCGAGATCT ATTTAGATTT TTACAACTGC TCTGTGAAGG CATAACAAT
11251  GATTTTCAAA ATTATCTACG CACTCAGATG GGCAACACCA CAACAGTGAA
```

FIG 7 (cont.)

| | | | | | |
|---|---|---|---|---|---|
| 11301 | TATTATCATT | AGTACAGTTG | ACTACCTCTT | GCGTCTTCAG | GAATCAATCA |
| 11351 | GTGACTTCTA | TTGGTACTAT | TCAGGAAAAG | AGTTTATTGA | TGAATCAGGA |
| 11401 | CAACGTAACT | TCTCTAAAGC | TCTGGCTGTC | ACCAAACAAA | TATTCAATTC |
| 11451 | CCTTACCGAA | TATATACAGG | GACCTTGCAT | CGGTAACCAA | CAGAGTCTGG |
| 11501 | CTCATAGTAG | GCTGTGGGAT | GCAGTTGTTG | GATTTCTTCA | TGTATTTGCC |
| 11551 | AATATGCAGA | TGAAACTTTC | ACAGGACTCT | GCTCAGATTG | AACTGCTTAA |
| 11601 | GGAACTGCTA | GaTCTGCTAA | AGGATATGGT | TGTGATGTTG | TTGTCATTAC |
| 11651 | TTGAAGGTAA | CGTTGTAAAT | GGAACAATTG | GAAAACAAAT | GGTCGATACA |
| 11701 | CTTGTAGAAT | CATCTAGCAA | CGTAGAATTA | ATCTTGAAGT | TTTTTGACAT |
| 11751 | GTTTCTCAAA | TTAAAAGATT | TAACTAACTC | GGATGCTTTC | AAGGAGCATG |
| 11801 | ACCCAGATGG | TAAGGGCATC | ATTTCAAAGA | AGGATTTCCA | GAAGTCAATG |
| 11851 | GAGGCTCAAA | AACAATATAT | ACAATCAGAG | ATTGAATTCC | TGTTGTCATG |
| 11901 | TACGGAAGCT | GATGAAAATG | ATATGTTCAA | CTACATTGAT | TTTGTAGAAA |
| 11951 | GATTCCATGA | ACCAGCCAAA | GATATTGGCT | TTAATGTAGC | AGTTTTGCTA |
| 12001 | ACAAACCTTT | CAGAGCATAT | GCCTAATGAC | TCACGCCTTC | AGAGCTTACT |
| 12051 | TGAACCTGCA | GAAAGTGTTC | TTAATTACTT | TGAACCATAC | CTTGGCCGTA |
| 12101 | TTGAAATAAT | GGGTGGAGCC | AAGAAAATAG | AAAGAGTTTA | CTTTGAAATC |
| 12151 | AGTGAATCCA | GTAGAATGCA | GTGGGAAAAG | CCACAGGTGA | AGGAATCCAA |
| 12201 | AAGGCAATTC | ATATTTGATG | TTGTAAACGA | AGGTGGAGAG | CAAGAAAAAA |
| 12251 | TGGAGCTCTT | CGTGAACTTC | TGTGAAGACA | CGATCTTTGA | AATGCAGTTA |
| 12301 | GCATCCCAAA | TCTCTGAGAC | TGATTCAGCT | GAGAGACCTG | AGGAAGAGGA |
| 12351 | AGAAGAGCCT | TGCTACATTG | TGGATATCGG | AGATGATGAG | GAAGAAGAAA |
| 12401 | AGTCCCTGGA | ATCTCCTTCA | GCTTTTGCAA | TGGCCTGTGC | TGCAGTCAAG |
| 12451 | AAGAACGTCG | CCAACTTTTT | TAAAATGGTT | ACTGTGAAGA | ACCTAAGGAA |
| 12501 | ACAGTACAGG | AAAGTCAGAA | AGATGACAGT | AAAAGAGATG | GTGAAAGTGT |
| 12551 | TTTTCTCTTT | TTTCTGGATT | CTATTTGTAG | GGGTGTTCCA | ACTGTTTTTT |
| 12601 | ACTATAGTAT | GGGGAATTTT | CCAGATTCTT | GGAGCACCG | TATTTGGGGG |
| 12651 | TGGACTGGTT | GAAGGAGCCA | AAAATATTAA | AGTTACTAAA | ATACTAGGGG |
| 12701 | ACATGCCTGA | CCCAACGCAG | TTTGGAATCC | ATGATGATGT | CACAGAAGCA |

FIG 7 (cont.)

| | |
|---|---|
| 12751 | GAAAAAACTG AAGGTGCTGA GCATGGCATT AGAGATGAAC TTGTGCAGTT |
| 12801 | TGTAAAGGGT GAAAAGGGAG AAGCTGACAT AATTTCAGAT ATTTTTGGCA |
| 12851 | TTCCTACTAA GAAAGAAGGT GGCTCAAAAC ATGGTCATGA CGCTGGACTT |
| 12901 | GGAGATATTG CAGAAATACT TGGCTCTGAT ATCCAGTCTT CTCTGGAAAA |
| 12951 | CAATGTTCGT AAGAAAAAAG GATTACAGAC ACCTGAAACT GCAAAAGACG |
| 13001 | CTGAAGCAGA AGAAAAGTA GAAGCTGAGA AGGCTGACAT GGAAGATGGT |
| 13051 | GAGAAACAGG ATAAAGCAAA GGAAGAACAC TCTGAGCAGC AGGAAGAGGG |
| 13101 | AAAAACAAAG AAAAAGAAGC GAAGGCATGG ACAAAAAATT GAGAAACCTG |
| 13151 | TGGCTGTTAT GGCTAATTTC TTCAAAGCTT TGGAAATATA TCAAACAAAA |
| 13201 | ATGCTTCACT ACCTGGCAAG GAACTTTTAT AACTTACGGT TTCTTGCTCT |
| 13251 | ATTTGTTGCA TTTGCCATCA ACTTTATTCT GCTATTTTAC AAGGTGACAG |
| 13301 | AAGAGCCACT TGATGAAGTG GAGGAAGACT CTAATCTCTG GAACTCTTTT |
| 13351 | GAAGAAGAGG AAGAGGAGGA AGGAATGGTA TTTTTTGTTT TGGAAGAAAG |
| 13401 | TACAGGTTAC ATGGCACCTA CTCTCAGAGC ACTGGCAGTT ATTCATACTA |
| 13451 | TCATCTCCTT TGtCTGTGTG ATTGGATACT ATTGCTTAAA GGtCCCTTTG |
| 13501 | GTTGTATTCA AGAgAGAAAA GGAGGTAGCT AGGAAgCTGG AAtTTGATGG |
| 13551 | ATTATACaTA ACTGAACAAC CATCTGAAGA TGATATTAAA GGACAGTGGG |
| 13601 | ATCGCCTGGT TATAAACACA CCGTCCTTTC CTAACAATTA CTGGGATAAA |
| 13651 | TTTGTAAAAC GAAAGGTTAT TAACAAGTAT GGAGACTTGT ACGGAGCAGA |
| 13701 | GCGTATAGCA GAACTTTTGG GTTTGGACAA AAATGCCCTT GATTTTAGTC |
| 13751 | CAGTGGAAGA GAGCGAACCA GAAGCGGCAT CTCTTGTATC ATGGTTAAGT |
| 13801 | TCCATTGATA CAAAGTACCA CATTTGGAAG CTTGGTGTTG TTTTCACTGA |
| 13851 | TAATTCATTT TTGTATTTGG CTTGGTACAC AACTATGTCT ATCCTTGGAC |
| 13901 | ACTACAACAA CTTCTTTTTT GCTGCTCATC TGCTGGACAT CGCTATGGGT |
| 13951 | TTCAAGACAT TGCGAACCAT TTTGTCCTCT GTAACTCACA ATGGCAAACA |
| 14001 | GCTTGTGCTT ACTGTAGGAC TcCTGGCTGT AGTAGTGTAT CtTTACACTG |
| 14051 | tTGtGGCATT CAaCTTCtTc CGCaAATTCT ACAaTaAAAG tgaagaTGAA |
| 14101 | GATGAACCAG ATATGAAATG TGATGACATG ATGACGTGTT ACCTATTCCA |

FIG 7 (cont.)

```
14151  CATGTATGTG  GGTGTAAGAG  CTGGTGGTGG  CATTGGGGAT  GAAATTGAGG
14201  ATCCTGCTGG  AGACCCTTAT  GAAATTTATC  GAATTGTCTT  CGACATCACA
14251  TTTTTCTTCT  TTGTCATTGT  CATCCTACTG  GCCATTATTC  AAGGTCTGAT
14301  TATTGACGCT  TTTGGTGAAT  TAAGAGACCA  GCAAGAACAA  GTGAGAGAAG
14351  ATATGGAGAC  CAAATGCTTT  ATTTGTGGAA  TTGGCAACGA  CTATTTTGAC
14401  ACAACTCCAC  ATGGCTTTGA  ACACATACT   CTGCAGGAAC  ACAACTTGGC
14451  AAACTACCTG  TTCTTCTTAA  TGTACCTCAT  AAACAAGGAT  GAGACTGAGC
14501  ATACTGGCCA  GGAGTCATTT  GTGTGGAAGA  TGTACCAAGA  AAGATGCTGG
14551  GATTTCTTCC  CAGCAGGAGA  CTGCTTCCGG  AAACAGTATG  AGGATCAACT
14601  CGGCAATCGA  ATTCCCGCGG
```

Turkey (OH-H), β-RyR entire amino acid sequence
β-Turkey   Length: 4868   August 29, 2001 10:01   Type: P

```
  1  MAEGGEGGED  EIQFLRTDDE  VVLQCVSSIH  KEQRKFCLAA  EGLGNRLCFL
 51  EPTSEAKYVP  PDLCICNFVL  EQSLSVRALQ  EMLTNTGDNA  SEGAAQGGHR
101  TLLYGHAILL  RHSFSEMYLT  CLTSSRSQTD  KLAFDVGLRE  NAAGEACWWT
151  IHPASKQRSE  GEKVRIGDDL  ILVSVSSERY  LHLSMSNGSI  QVDASFMQTL
201  WNVHPTCSGS  NITEGYLLGG  HVVRFFHGHD  ECLTIPSTDQ  NDSQQKKVLY
251  ETGGAGVRAR  SLWRVEPLRI  SWSGSNIRWG  QPFRLRHITT  GMYLALNDDE
301  GLVMLDREKS  DTTSSAFCFR  ASKELKEKQD  STLKRDIDGM  GVPEIKYGDS
351  VCFVQHVASA  LWLTYKAPDA  KSARLGLLKR  KVILHQEGHM  DDGLTLQRCQ
401  HEESQAARII  RNTTSLFSQF  ISGNNRTLSP  IALPVEEMAQ  TLQDLIKYFQ
451  PPGEDLEHED  KQNKLRSLKN  RQNLFKDEGM  LALVLNCIDR  LNDYNSAAHF
501  AEIAREENST  AWKEILNLLY  ELLAALIRGN  RNNCTQFSSN  LDWLISKLDR
551  LESSSGILEV  LHCILIESPE  ALNVIAEEHI  KSIISLLDKH  GRNYKVLDVL
601  CSLCVCNGVA  VRANQNLICD  NLLPRRDLLL  QTRLINDVTS  IRPNIFLGVA
651  EGSAQYKKWY  FELIIDQVDP  FLTAEPTHLR  VGWASTSGYA  PYPGGGEGWG
701  GNGVGDDLYS  FGFDGLHLWS  GRVPRAVASV  NQHLLSSDDV  VSCCLDLGVP
```

```
 751  SISFRINGQP  VQGMFENFCT  EGFFFPVVSL  SAGVKARFLL  GGRHGEFKFL
 801  PPAGYAPCYE  ALLPKEKMKL  EPVKEYKRDS  DGVRDLLGTT  QFLSQASFIP
 851  CPIDTSQIAL  PFHLEKIRDK  LAENIHELWG  MNKIELGWTY  GKIRDDNKRH
 901  HPCLVEFSKL  PETEKNYNLQ  MSTETLKTLL  ALGCHIVHAN  PAAEEDLKKV
 951  KLPKNYIMSN  GYKPAPLDLS  EVKLLPSQEF  LVDKLAENAH  NVWAKDRIKQ
1001  GWTYGIQQDL  KNKRNPRLVP  YALLDERTKK  SNRDSLREAV  RTFAGYGYNI
1051  EPPDQEIADQ  TLEKVSIDKI  RFFRVEQSYA  VKSGKWYFEF  EAVTGGDMRV
1101  GWARPGCRPD  IELGADDQAF  VFEGSKGQRW  HQGSGFFGRS  WQPGDVVGCM
1151  INLDDKSIIF  TLNGELLITS  KGSELAFADF  GIESGFVPIC  SLGLAQIGRM
1201  NLGMDASTFK  YYTMCGLQEG  FEPPAVNMNR  DVAMWFSKRL  PTFVNVPKNH
1251  PHIEIWRIDG  TIESPPRLKV  THKTLGTQNS  NSDMIYCRLS  MPIEFRSSFN
1301  FGVGVENASS  DALQKRKHSQ  EFPASSTTYF  YSLRIFAGQD  PSSVWVGWVT
1351  PDYHFYSENF  DINKNCTVTV  TLGDERGRVH  ESVKRSNCYM  VWGGDITANS
1401  QRSGRSNVDL  EIGCFVDLAT  GMLSFTANGK  ELGTCYQVEP  NTKLLPAAFV
1451  QPTSTNLIQF  ELGKLKNTMP  LSAAIFKSEE  RNPVPQCPPR  LDVQTITPVL
1501  WSRMPNSFLK  VETERVSERH  GWVVQCLEPL  QMMALHIPEE  NRCVDILELC
1551  EQEDLMKFHY  HTLKLYSSVC  ALGNTRVAYA  LCSHVDISQL  FYTIDNQYLP
1601  GLLRSGFYDL  LISIHLDHAK  QAKLMMNNEF  IIPVTEETRT  IKLYPDETKK
1651  HGLPGVGLST  CLKPSFNFST  PCFIVTSEEH  QTSSPEIPLD  TLKSKAISML
1701  TEAVQCSGSH  IRDPVGGHIA  FQFVPVLKLI  ATLLIMGVFD  DDDVKQVLIL
1751  IDPNVFGDNK  EETEERTEKE  EVTQVEEKAV  EAGEKAVKET  KTPTKGLLQT
1801  RLPESGKLQM  CHLLNYFCDC  ELQHRVEAIV  SFADHYVSKL  QYNQKYRYNE
1851  LMQALDMSAA  LTAKKTKEFR  SPPQEQINML  LNFQLGEDCP  CPEEIRDELY
1901  DFHDDLLIHC  GIPLEEEEEE  EEDSSLTGKL  RSLIYKIKGP  PKPEKIEPRE
1951  EEDKSPTTLK  ELISQTMVRW  SQEDQIQDPE  LVRIMYTLLR  RQYDSIGELL
2001  QALRKAYTIS  AGSVKDTINL  LAALGQIRSL  LSVRMGKEEE  LLMINGLGDI
2051  MNNKVFYQHP  NLMRVLGMHE  TVMDVMVNVL  GGDKSQIVFP  KMVASCCRFL
2101  CYFCRISRQN  QKAMFEHLSY  LLENSSVGLA  FPSMRGSTPL  DVAAASVMDN
```

FIG 7 (cont.)

```
2151  NELALALEEP  DLDKVVTYLA  GWGLQRCPVL  LAKGYPDIGW  NPIEGERYLS
2201  FLRFAVFVNS  ESVEENASVV  VKLLIRRPEC  FGPELRGEGG  NGLLAAMQEA
2251  IRISENPSRD  LPSQGYKREG  DEEEEEEEIV  HMGNAIMSFY  SALIDLLGRC
2301  APEMHLIQSG  KGEAIRIRSI  LRSLVPTEDL  VGIISIPLKL  STVNKDGTVN
2351  EPDMSANFCP  DHKAPMVLFL  DRVYGIKDQS  FLLHLLEVGF  LPDLRASASL
2401  DTVSLSTTEA  ALALNRYICS  AVFPLLKRCA  PLFSGTEHHA  SLVDSMLHTI
2451  YRLSKGRSLT  KAQRDTIEEC  LLAICHHLRP  SMLQQLLRRL  VFDVPLLNEY
2501  CKMPLKLLTN  HYEQCWKYYC  LPSGMGSYGI  AAEDELHLTE  KLFWGIFDSL
2551  SHKKYDPELF  RMALPCLSAI  AGALPPDYLD  TRIRSTLEKQ  TSVDPEGNFD
2601  PKPINTANLV  LPEKLEYIVS  KYAEHSHDKW  AFDKTNNGWK  YGVSLDENTK
2651  THPLIRPFKT  LTEKEKEIYR  WPVRESLKTM  LAMGWSLERT  KEGGEGMLHQ
2701  RENEKLRSIS  QSSQGNGYSP  APLDLTNVVL  SRELQGMVEV  MAENYHNIWA
2751  KKKKMELESK  GGGSHPLLVP  YDTLTAKEKS  RDREKAQELF  KFLQVNGIII
2801  SRGLNDMDLD  ASSMEKRFAF  KFLKKILKYV  DSAQEFIAHL  EAIVTSGKTE
2851  KSPHDQEIKF  FAKVLLPLVD  QYFTNHCLYF  LSSPTKTLSS  SGYASNKEKE
2901  MVASLFCKLA  ALVRHRISIF  GSDSTTMVSC  LHILAQSLDT  RTVMKSGSEL
2951  VKAGLRAFFE  NAAEDLEKTS  ENLKLGKFTH  SRTQIKGVSQ  NINYTTVALL
3001  PVLTSIFEHI  SQYHFGVDLL  LGDVQVSCYR  ILCSLYSLGT  GKNIYVERQR
3051  PALGECLASF  AAAIPVAFLE  PSLNHYNPLS  VFNTKSARER  AILGMPDTVE
3101  EMCPEIPQLD  GLIKEINNLA  ESGARYTEMP  HVIEVILPML  CNYLSYWWER
3151  GSESVPESAG  PCCTMITSEH  LSIILGNILK  IINTNLGIDE  ASWMKRIAVY
3201  AQPIISKARP  DLLKTHFIPT  LEKLKKKAIK  IVMEEEQLRA  DSKSDTQEAE
3251  LLILDEFAVL  CRDLYAFYPM  LIRYVDNNRA  NWLKKPDADS  DELFRMVAEV
3301  FILWCKSHNF  KREEQNFVIQ  NEINNLAFLT  GDTKSKMSKA  MQVKSGGQDQ
3351  ERKKSKRRGD  LYSIQTSLIV  AALKKMLPIG  LNMCTPGDQE  LISLAKTRYS
3401  HKDTDEEVKE  HIRNNLHLQE  KSDDPAVKWQ  LNLYKDILKS  DEPPDPEKNV
3451  ERVQRISAAL  YHLDQVEQPL  RSKKAVWHKL  LSKQRKRAVV  ACFRMAPLYN
3501  LPRHRSINLF  LHGYQNYWIE  TEEYSFEEKL  VQDLATSPKK  EEEEEEDTEK
3551  EQPDPLHQII  LYFSRNALTE  RSKLEDDPLY  IAYAAMMAKS  CQEEEEEEEE
```

FIG 7 (cont.)

```
3601  DKEKTFEEKE MEKQRTLYQQ ARLHDRGAAE MVLQMISASK GHTGPMVVET

3651  LKLGIAILNG GNTIVQQKML DYLKEKKDAG FFQSLSGLMQ SCSVLDLNAF

3701  ERQNKAEGLG MVTEEGTLIV RERGEKVLQH DEFTRDLFRF LQLLCEGHNN

3751  DFQNYLRTQM GNTTTVNIII STVDYLLRLQ ESISDFYWYY SGKEFIDESG

3801  QRNFSKALAV TKQIFNSLTE YIQGPCIGNQ QSLAHSRLWD AVVGFLHVFA

3851  NMQMKLSQDS AQIELLKELL DLLKDMVVML LSLLEGNVVN GTIGKQMVDT

3901  LVESSSNVEL ILKFFDMFLK LKDLTNSDAF KEHDPDGKGI ISKKDFQKSM

3951  EAQKQYIQSE IEFLLSCTEA DENDMFNYID FVERFHEPAK DIGFNVAVLL

4001  TNLSEHMPND SRLQSLLEPA ESVLNYFEPY LGRIEIMGGA KKIERVYFEI

4051  SESSRMQWEK PQVKESKRQF IFDVVNEGGE QEKMELFVNF CEDTIFEMQL

4101  ASQISETDSA ERPEEEEEEP CYIVDIGDDE EEEKSLESPS AFAMACAAVK

4151  KNVANFFKMV TVKNLRKQYR KVRKMTVKEM VKVFFSFFWI LFVGVFQLFF

4201  TIVWGIFQIL WSTVFGGGLV EGAKNIKVTK ILGDMPDPTQ FGIHDDVTEA

4251  EKTEGAEHGI RDELVQFVKG EKGEADIISD IFGIPTKKEG GSKHGHDAGL

4301  GDIAEILGSD IQSSLENNVR KKKGLQTPET AKDAEAERKV EAEKADMEDG

4351  EKQDKAKEEH SEQQEEGKTK KKKRRHGQKI EKPVAVMANF FKALEIYQTK

4401  MLHYLARNFY NLRFLALFVA FAINFILLFY KVTEEPLDEV EEDSNLWNSF

4451  EEEEEEEGMV FFVLEESTGY MAPTLRALAV IHTIISFVCV IGYYCLKVPL

4501  VVFKREKEVA RKLEFDGLYI TEQPSEDDIK GQWDRLVINT PSFPNNYWDK

4551  FVKRKVINKY GDLYGAERIA ELLGLDKNAL DFSPVEESEP EAASLVSWLS

4601  SIDTKYHIWK LGVVFTDNSF LYLAWYTTMS ILGHYNNFFF AAHLLDIAMG

4651  FKTLRTILSS VTHNGKQLVL TVGLLAVVVY LYTVVAFNFF RKFYNKSEDE

4701  DEPDMKCDDM MTCYLFHMYV GVRAGGGIGD EIEDPAGDPY EIYRIVFDIT

4751  FFFFVIVILL AIIQGLIIDA FGELRDQQEQ VREDMETKCF ICGIGNDYFD

4801  TTPHGFETHT LQEHNLANYL FFLMYLINKD ETEHTGQESF VWKMYQERCW

4851  DFFPAGDCFR KQYEDQLG*

Note: "*" represents the stop codon.
```

FIG 7 (cont.)

```
LOCUS       AY372817                 717 bp    mRNA    linear   VRT 28-AUG-2003
DEFINITION  Meleagris gallopavo ryanodine receptor alpha isoform mRNA, partial
            cds.
ACCESSION   AY372817
VERSION     AY372817
KEYWORDS    .
SOURCE      Meleagris gallopavo (turkey)
  ORGANISM  Meleagris gallopavo
            Eukaryota; Metazoa; Chordata; Craniata; Vertebrata; Euteleostomi;
            Archosauria; Aves; Neognathae; Galliformes; Phasianidae; Meleagris.
REFERENCE   1  (bases 1 to 717)
  AUTHORS   Chiang,W., Allison,C., Linz,J.E. and Strasburg,G.M.
  TITLE     Identification of two alpha-RYR alleles and characterization of
            alpha-RYR transcript variants in turkey skeletal muscle
  JOURNAL   Unpublished
REFERENCE   2  (bases 1 to 717)
  AUTHORS   Chiang,W., Linz,J.E. and Strasburg,G.M.
  TITLE     Direct Submission
  JOURNAL   Submitted (22-AUG-2003) Food Science & Human Nutrition, Michigan
            State University, R323 G.M. Trout, East Lansing, MI 48824, USA
FEATURES             Location/Qualifiers
     source          1..717
                     /organism="Meleagris gallopavo"
                     /mol_type="mRNA"
                     /db_xref="taxon:9103"
                     /tissue_type="skeletal muscle"
     CDS             <1..>717
                     /note="alpha-RyR; similar to Homo sapiens RYR1 in GenBank
                     Accession Number J05200"
                     /codon_start=1
                     /product="ryanodine receptor alpha isoform"
                     /protein_id="AAQ63939"
                     /translation="ILEQEGHMDDALSLSRSQGEESQAARMIYSTAGLYGSFIRSLDA
                     LSSRGRGGGAGNAALPIAAVILSLRDLIAYFRAPHTELQHEQRQNRLRSLRRRQDLFQ
                     QEGMISLVLNCIDRLNVYSTAAHFAEFAGEEAAAAWKEIVNLLYELLASLIRGNRTNC
                     ALFSTNLDWLVSKLDRLEASSGILEVLYCVLIESPEVLNIIQENHIKSIISLLDKHGR
                     NHKVLDVLCSLCVCNAVAVRS"

BASE COUNT    122 a    238 c    230 g    127 t (nucleotide sequence of wild type)

1 attctgcacc aggagggcca catggacgac gcgctgtcgc tcagccgctc gcagggcgag
   61 gagtcgcagg cggcgcggat gatttacagc acggcggggc tctacgggag cttcatccgg
  121 agcctggacg cgctgagctc tcggggccgc ggcggcggtg cgggaacgc ggctctgccc
  181 atcgccgccg tcatcctcag cctgcgggat ctgatcgctt atttccgcgc ccgcacacc
  241 gagctgcagc acgagcagcg ccagaaccgc ctgcgctccc tgcggcgccg ccaggacctc
  301 ttccagcagg aggggatgat ctccctggtg ctgaactgca tcgaccggct gaacgtgtac
  361 agcacggccg cgcacttcgc cgagttcgcc ggggaggagg cggcggccgc ctggaaggag
  421 atcgtcaacc tcctctatga gctgctggcc tcgctgatcc gggggaaccg aaccaactgc
  481 gccctgttct ccaccaacct ggactggctg gtcagcaaac tggaccggct ggaggcgtcg
  541 tcagggatcc tggaggtgct ttactgcgtc ctgatcgaga gccccgaggt tctgaacatc
  601 atccaggaga accacatcaa gtccatcatc tccctgctgg acaaacacgg ccgcaaccat
  661 aaggtcctgg acgtgctctg ctctctgtgt gtctgcaatg ctgtggccgt tcgttcc
```

Note: The deleted 81-bp is underlined and the deleted 193-bp is shown in blue.

FIG 8

(nucleotide sequence of AS-81)
AS-81   Length: 636   January 30, 2004 16:16   Type: N

```
  1 attctgcacc aggagggcca catggacgac gcgctgtcgc tcagccgctc
 51 gcagggcgag gagtcgcagg cggcgcggat gatttacagc acggcggggc
101 tctacgggag cttcatccgc ctgcgggatc tgatcgctta tttccgcgcc
151 ccgcacaccg agctgcagca cgagcagcgc cagaaccgcc tgcgctccct
201 gcggcgccgc caggacctct tccagcagga ggggatgatc tccctggtgc
251 tgaactgcat cgaccggctg aacgtgtaca gcacggccgc gcacttcgcc
301 gagttcgccg gggaggaggc ggcggccgcc tggaaggaga tcgtcaacct
351 cctctatgag ctgctggcgt cgctgatccg ggggaaccga accaactgcg
401 ccctgttctc caccaacctg gactggctgg tcagcaaact ggaccggctg
451 gaggcgtcgt cagggatcct ggaggtgctt tactgcgtcc tgatcgagag
501 ccccgaggtt ctgaacatca tccaggagaa ccacatcaag tccatcatct
551 ccctgctgga caaacacggc cgcaaccata aggtcctgga cgtgctctgc
601 tctctgtgtg tctgcaatgc tgtggccgtt cgttcc
```

Amino acid sequence of AS-81 check: 1087 from: 1 to: 636
AS-81   Length: 212   January 30, 2004 16:17

```
  1 ILHQEGHMDD ALSLSRSQGE ESQAARMIYS TAGLYGSFIR LRDLIAYFRA
 51 PHTELQHEQR QNRLRSLRRR QDLFQQEGMI SLVLNCIDRL NVYSTAAHFA
101 EFAGEEAAAA WKEIVNLLYE LLASLIRGNR TNCALFSTNL DWLVSKLDRL
151 EASSGILEVL YCVLIESPEV LNIIQENHIK SIISLLDKHG RNHKVLDVLC
201 SLCVCNAVAV RS
```

FIG 8 (cont.)

Nucleotide sequence of AS-193
AS-193 Length: 524 January 30, 2004 16:22 Type: N

```
  1  attctgcacc aggagggcca catggacgac gcgctgtcgc tcagccgctc 51  gcagggcgag gagtcgcagg cggcgcggat gatttacagc acggcggggc 101  tctacgggag cttcatccgg ggatgatctc cctggtgctg aactgcatcg 151  accggctgaa cgtgtacagc acggccgcgc acttcgccga gttcgccggg 201  gaggaggcgg cggccgcctg gaaggagatc gtcaacctcc tctatgagct 251  gctggcgtcg ctgatccggg ggaaccgaac caactgcgcc ctgttctcca 301  ccaacctgga ctggctggtc agcaaactgg accggctgga ggcgtcgtca 351  gggatcctgg aggtgcttta ctgcgtcctg atcgagagcc ccgaggttct 401  gaacatcatc caggagaacc acatcaagtc catcatctcc ctgctggaca 451  aacacggccg caaccataag gtcctggacg tgctctgctc tctgtgtgtc 501  tgcaatgctg tggccgttcg ttcc
```

TRANSLATE of: as-193 check: 1195 from: 1 to: 524
Amino acid sequence of AS-193
AS-193 Length: 174 January 30, 2004 16:22

```
  1  ILHQEGHMDD ALSLSRSQGE ESQAARMIYS TAGLYGSFIR G*SPWC*TAS

51  TG*TCTARPR TSPSSPGRRR RPPGRRSSTS SMSCWRR*SG GTEPTAPCSP

101  PTWTGWSANW TGWRRRQGSW RCFTAS*SRA PRF*TSSRRT TSSPSSPCWT

151  NTAATIRSWT CSALCVSAML WPFV
```

(Note: The deletion of 193 base pairs leads to a premature stop codons indicated as "*")

SEQUENCE LISTING

```
<160> NUMBER OF SEQ ID NOS: 27

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5
<211> LENGTH: 239
<212> TYPE: PRT
<213> ORGANISM: Meleagris gallopavo

<400> SEQUENCE: 5

Ile Leu His Gln Glu Gly His Met Asp Asp Ala Leu Ser Leu Ser Arg
1               5                   10                  15

Ser Gln Gly Glu Glu Ser Gln Ala Ala Arg Met Ile Tyr Ser Thr Ala
            20                  25                  30

Gly Leu Tyr Gly Ser Phe Ile Arg Ser Leu Asp Ala Leu Ser Ser Arg
        35                  40                  45

Gly Arg Gly Gly Gly Ala Gly Asn Ala Ala Leu Pro Ile Ala Ala Val
    50                  55                  60

Ile Leu Ser Leu Arg Asp Leu Ile Ala Tyr Phe Arg Ala Pro His Thr
65                  70                  75                  80

Glu Leu Gln His Glu Gln Arg Gln Asn Arg Leu Arg Ser Leu Arg Arg
                85                  90                  95

Arg Gln Asp Leu Phe Gln Gln Glu Gly Met Ile Ser Leu Val Leu Asn
            100                 105                 110
```

Cys Ile Asp Arg Leu Asn Val Tyr Ser Thr Ala Ala His Phe Ala Glu
            115                 120                 125

Phe Ala Gly Glu Glu Ala Ala Ala Trp Lys Glu Ile Val Asn Leu
130                 135                 140

Leu Tyr Glu Leu Leu Ala Ser Leu Ile Arg Gly Asn Arg Thr Asn Cys
145                 150                 155                 160

Ala Leu Phe Ser Thr Asn Leu Asp Trp Leu Val Ser Lys Leu Asp Arg
                165                 170                 175

Leu Glu Ala Ser Ser Gly Ile Leu Glu Val Leu Tyr Cys Val Leu Ile
            180                 185                 190

Glu Ser Pro Glu Val Leu Asn Ile Ile Gln Glu Asn His Ile Lys Ser
        195                 200                 205

Ile Ile Ser Leu Leu Asp Lys His Gly Arg Asn His Lys Val Leu Asp
    210                 215                 220

Val Leu Cys Ser Leu Cys Val Cys Asn Ala Val Ala Val Arg Ser
225                 230                 235

<210> SEQ ID NO 6
<211> LENGTH: 212
<212> TYPE: PRT
<213> ORGANISM: Meleagris gallopavo

<400> SEQUENCE: 6

Ile Leu His Gln Glu Gly His Met Asp Asp Ala Leu Ser Leu Ser Arg
1               5                   10                  15

Ser Gln Gly Glu Glu Ser Gln Ala Ala Arg Met Ile Tyr Ser Thr Ala
            20                  25                  30

Gly Leu Tyr Gly Ser Phe Ile Arg Leu Arg Asp Leu Ile Ala Tyr Phe
        35                  40                  45

Arg Ala Pro His Thr Glu Leu Gln His Glu Gln Arg Gln Asn Arg Leu
    50                  55                  60

Arg Ser Leu Arg Arg Arg Gln Asp Leu Phe Gln Gln Glu Gly Met Ile
65                  70                  75                  80

Ser Leu Val Leu Asn Cys Ile Asp Arg Leu Asn Val Tyr Ser Thr Ala
                85                  90                  95

Ala His Phe Ala Glu Phe Ala Gly Glu Glu Ala Ala Ala Trp Lys
            100                 105                 110

Glu Ile Val Asn Leu Leu Tyr Glu Leu Leu Ala Ser Leu Ile Arg Gly
        115                 120                 125

Asn Arg Thr Asn Cys Ala Leu Phe Ser Thr Asn Leu Asp Trp Leu Val
130                 135                 140

Ser Lys Leu Asp Arg Leu Glu Ala Ser Ser Gly Ile Leu Glu Val Leu
145                 150                 155                 160

Tyr Cys Val Leu Ile Glu Ser Pro Glu Val Leu Asn Ile Ile Gln Glu
                165                 170                 175

Asn His Ile Lys Ser Ile Ile Ser Leu Leu Asp Lys His Gly Arg Asn
            180                 185                 190

His Lys Val Leu Asp Val Leu Cys Ser Leu Cys Val Cys Asn Ala Val
        195                 200                 205

Ala Val Arg Ser
    210

<210> SEQ ID NO 7
<211> LENGTH: 41
<212> TYPE: PRT

<213> ORGANISM: Meleagris gallopavo

<400> SEQUENCE: 7

```
Ile Leu His Gln Glu Gly His Met Asp Asp Ala Leu Ser Leu Ser Arg
1               5                   10                  15
Ser Gln Gly Glu Glu Ser Gln Ala Ala Arg Met Ile Tyr Ser Thr Ala
            20                  25                  30
Gly Leu Tyr Gly Ser Phe Ile Arg Gly
            35                  40
```

<210> SEQ ID NO 8
<211> LENGTH: 3168
<212> TYPE: DNA
<213> ORGANISM: Meleagris gallopavo

<400> SEQUENCE: 8

| | | | | | |
|---|---|---|---|---|---|
| atgggtgacg | gaggagaggg | cgatgtgcag | ttcctgagga | cggacgatga | ggtggtgctg | 60 |
| caatgcacca | cgacgctgct | gaaggagcag | ctgaagctct | gcctggcggc | cgaaggcttc | 120 |
| gggaaccgcc | cgtgcttcct | ggagcccacg | tccaacgcac | agaatgtgcc | ccccgacctg | 180 |
| gccgtctgct | gcttcgtctt | ggagcagtcg | ctgtcagtcc | gagcgctgca | ggagatgttg | 240 |
| gccaactgtg | cagagagcgg | cagagagtcg | tcgcagggcg | gggggcatcg | cacgctgctc | 300 |
| tatggacacg | ccatcctgct | gcggcactcc | catagcggga | tgtacctgag | ctgcctgacc | 360 |
| acctcccgct | ccgtcaccga | caaactggcc | ttcgatgtgg | ggctgcagaa | ggacgcagcg | 420 |
| ggggaggcct | gttggtggac | gctgcacccg | gcgtcgaagc | agcgctcaga | gggggaaaag | 480 |
| gtgcgagtgg | gggacgacat | catcctggtg | agcgtctcct | ccgagcgcta | cctgcacctc | 540 |
| tcgacggcca | gcggggagct | gcaggcggac | gcctccttca | tgcagaccct | gtggaacatg | 600 |
| aaccccatct | gctcggggc | cgaggaaggt | tatgtgacgg | ggggccacgt | gctgcgtctg | 660 |
| ttccacggcc | acatggatga | gtgcctcagc | acctcccccc | ccgagcaggg | ggacgagcgc | 720 |
| agcagcgtgg | tgagctacga | ggggggggcc | gtctgcaccc | acgcacggtc | gctgtggagg | 780 |
| ttggagccgc | tgcgcatcag | ttggagcggc | agccacctcc | gctgggggca | gcccttccgg | 840 |
| gttcgtcacg | tgacgtcggg | ccgctatttg | gcgctgagcg | aagagcgcgg | cctcgtggtg | 900 |
| gtggaagcgg | cggcggccgg | gacccgagcg | gctgcgttct | gcttccgggc | ctccaaggag | 960 |
| aagctggaag | cggggacgaa | gcgcgatgtg | gaggggatgg | gaccccgga | gatcaaatat | 1020 |
| ggggagtcgc | tgtgcttcgt | gcagcacgcg | gcctcgggc | tgtggctcac | ctacgctgct | 1080 |
| gctgacacca | agcgctgcg | cctggggctg | atgaaacgga | ggcccatcct | gcaccaggag | 1140 |
| ggccacatgg | acgacgcgct | gtcgctcagc | cgctcgcagg | gcgaggagtc | gcaggcggcg | 1200 |
| cggatgattt | acagcacggc | ggggctctac | gggagcttca | tccggagcct | ggacgcgctg | 1260 |
| agctctcgtg | gccgtggcgg | cggtgcgggg | aacgcggctc | tgcccatcgc | cgccgtcatc | 1320 |
| ctcagcctgc | gggatctgat | cgcttatttc | cgcgccccgc | acaccgagct | gcagcacgag | 1380 |
| cagcgccaga | accgcctgcg | ctccctgcgg | cgccgcagg | acctcttcca | gcaggagggg | 1440 |
| atgatctccc | tggtgctgaa | ctgcatcgac | cggctgaacg | tgtacagcac | ggccgcgcac | 1500 |
| ttcgccgagt | tcgccgggga | ggaggcggcg | ccgcctgga | aggagatcgt | caacctcctc | 1560 |
| tatgagctgc | tggcgtcgct | gatccggggg | aaccgaacca | actgcgccct | gttctccacc | 1620 |
| aacctggact | ggctggtcag | caaactggac | cggctggagg | cgtcgtcagg | gatcctggag | 1680 |
| gtgctttact | gcgtcctgat | cgagagcccc | gaggttctga | acatcatcca | ggagaaccac | 1740 |

```
atcaagtcca tcatctccct gctggacaaa cacggccgca accataaggt cctgaacgtg    1800
ctctgctctc tgtgtgtctg caatgctgtg gccgttcgtt ccaaccaaaa tctcatcacc    1860
gaaaatctgc tcccgcgacg cgacctcctg ctgcagaccg gccggtcag ctacgtcagc     1920 agcatccggc ccaacatcct cctggggacc cacgagggcc ccacgcagta cccacgctgg    1980
tacttcgagg tggccgtgga tcacgtggag cccttcgtga cggcgcagcc cacccacctg    2040
cgcgtggggt gggcgatggc ggagggttac agccccctacc cggggggggg agagggctgg   2100
ggggcctacg gagccggaga cgacctttat tccttcgcct ttgatgggct gcacctctgg    2160
gccggcgggg ttccgcgggc cgcccccctcc ccccagcagc acatcctggc ccccggggac   2220
gtggtgagct gctgcctgga cctctctgtt cccaccatct cctcccgcct caacggcagc    2280
ccggtgctgg ggatgttcga gaagttcaat cgcgacgcgc tcttctcccc cgtcgtcagc    2340
ttctccgccg gcgtgcggct gcgcttcctg ctgggggggcc gccacgggga tttccagttc   2400 ctgcccccc ccgttactc cccctgtgcc gaggcgctgc tgccccgcga gcggctgcgc      2460
ctggaaccca tcaaagctta tagggggcgac ggccccccgc cccactgcct gctcggcccc   2520
acaaaggcgc tgccccacac cgccttcacc ccctgccccg tggacaccgc gcagatcgtt    2580
ctgccccccc acctggagcg catccgggag aagctggcgg agaacatcca tgagctgtgg   2640
gcgctgaccc gcatcgagca gggatggacc tacggcccca tccatgacga tgctgagcag    2700
ctccatccct gcctgctgga tttccacagc ctccccgagc cggagcgcaa ctacaacctg    2760
cagatgtcgg gggagacgct caagacgctg ctggcgctgg gctgccacgt ggggatggcg    2820
gacgagaagg cggaggagaa cctgaggaaa atcaaactgc ccaaaacgta cacgatgcgc   2880
aacggttaca aaccggcccc gctggacctg gcccacgtgc gcctgacgcc ggcgcagctg    2940
acgctggtgg atcggctggc ggagaacgcg cacaacgtct gggcgcggga ccgcgtgcag    3000
cagggccgga cctacagcat cgtgcaggac attaagaaca gcgcaaccc ccgcctggtg     3060 ccctacaacc tgctggacga gcgcaccaag aagaccaaca gggacagcct gtgcgaggcg    3120
gtgcggaccc tcatcggcta cggctacaac atcgagccac ctgaccag                3168
```

<210> SEQ ID NO 9
<211> LENGTH: 240
<212> TYPE: PRT
<213> ORGANISM: Homo sapiens

<400> SEQUENCE: 9

```
Met Leu His Gln Glu Gly His Met Asp Asp Ala Leu Ser Leu Thr Arg
1               5                   10                  15

Cys Gln Gln Glu Glu Ser Gln Ala Ala Arg Met Ile His Ser Thr Asn
                20                  25                  30

Gly Leu Tyr Asn Gln Phe Ile Lys Ser Leu Asp Ser Phe Ser Gly Lys
            35                  40                  45

Pro Arg Gly Ser Gly Pro Ala Gly Thr Ala Leu Pro Ile Glu Gly
        50                  55                  60

Val Ile Leu Ser Leu Gln Asp Leu Ile Ile Tyr Phe Glu Pro Pro Ser
65                  70                  75                  80

Glu Asp Leu Gln His Glu Glu Lys Gln Ser Lys Leu Arg Ser Leu Arg
                85                  90                  95

Asn Arg Gln Ser Leu Phe Gln Glu Glu Gly Met Leu Ser Met Val Leu
                100                 105                 110

Asn Cys Ile Asp Arg Leu Asn Val Tyr Thr Thr Ala Ala His Phe Ala
            115                 120                 125
```

```
Glu Phe Ala Gly Glu Glu Ala Ala Glu Ser Trp Lys Glu Ile Val Asn
            130                 135                 140

Leu Leu Tyr Glu Leu Leu Ala Ser Leu Ile Arg Gly Asn Arg Ser Asn
145                 150                 155                 160

Cys Ala Leu Phe Ser Thr Asn Leu Asp Trp Leu Val Ser Lys Leu Asp
                165                 170                 175

Arg Leu Glu Ala Ser Ser Gly Ile Leu Glu Val Leu Tyr Cys Val Leu
            180                 185                 190

Ile Glu Ser Pro Glu Val Leu Asn Ile Ile Gln Glu Asn His Ile Lys
        195                 200                 205

Ser Ile Ile Ser Leu Leu Asp Lys His Gly Arg Asn His Lys Val Leu
    210                 215                 220

Asp Val Leu Cys Ser Leu Cys Val Cys Asn Gly Val Ala Val Arg Ser
225                 230                 235                 240

<210> SEQ ID NO 10
<211> LENGTH: 240
<212> TYPE: PRT
<213> ORGANISM: Sus scrofa

<400> SEQUENCE: 10

Ile Leu His Gln Glu Gly His Met Asp Asp Ala Leu Ser Leu Thr Arg
1               5                   10                  15

Cys Gln Gln Glu Glu Ser Gln Ala Ala Arg Met Ile Tyr Ser Thr Ala
                20                  25                  30

Gly Leu Tyr Asn His Phe Ile Lys Gly Leu Asp Ser Phe Ser Gly Lys
            35                  40                  45

Pro Arg Gly Ser Gly Ala Pro Ala Gly Thr Ala Leu Pro Leu Glu Gly
        50                  55                  60

Val Ile Leu Ser Leu Gln Asp Leu Ile Gly Tyr Phe Glu Pro Pro Ser
65                  70                  75                  80

Glu Glu Leu Gln His Glu Glu Lys Gln Ser Lys Leu Arg Ser Leu Arg
                85                  90                  95

Asn Arg Gln Ser Leu Phe Gln Glu Glu Gly Met Leu Ser Leu Val Leu
                100                 105                 110

Asn Cys Ile Asp Arg Leu Asn Val Tyr Thr Thr Ala Ala His Phe Ala
            115                 120                 125

Glu Phe Ala Gly Glu Glu Ala Ala Glu Ser Trp Lys Glu Ile Val Asn
            130                 135                 140

Leu Leu Tyr Glu Ile Leu Ala Ser Leu Ile Arg Gly Asn Arg Ala Asn
145                 150                 155                 160

Cys Ala Leu Phe Ser Asn Asn Leu Asp Trp Leu Val Ser Lys Leu Asp
                165                 170                 175

Arg Leu Glu Ala Ser Ser Gly Ile Leu Glu Val Leu Tyr Cys Val Leu
            180                 185                 190

Ile Glu Ser Pro Glu Val Leu Asn Ile Ile Gln Glu Asn His Ile Lys
        195                 200                 205

Ser Ile Ile Ser Leu Leu Asp Lys His Gly Arg Asn His Lys Val Leu
    210                 215                 220

Asp Val Leu Cys Ser Leu Cys Val Cys Asn Gly Val Ala Val Arg Ser
225                 230                 235                 240

<210> SEQ ID NO 11
<211> LENGTH: 237
<212> TYPE: PRT
```

<213> ORGANISM: Rana catesbeiana

<400> SEQUENCE: 11

```
Ile Leu His Gln Glu Gly His Met Asp Asp Ala Leu Ser Leu Ser Arg
1               5                   10                  15

Ser Gln Arg Glu Glu Ser Gln Ala Ala Arg Met Ile Tyr Ser Thr Ala
                20                  25                  30

Gly Leu Phe Asn Ile Phe Ile Lys Gly Leu Asp Ser Leu Asn Gly Lys
            35                  40                  45

Asn Lys Pro Ser Lys Pro Ile Ser Leu Pro Leu Asp Met Val Val Leu
50                  55                  60

Thr Leu Gln Asp Leu Ile Gly Tyr Phe Gln His Pro Glu Glu Glu Leu
65                  70                  75                  80

Gln His Glu Glu Lys Gln Thr Lys Leu Arg Ser Leu Lys Asn Arg Gln
                85                  90                  95

Asn Leu Phe Gln Glu Glu Gly Ile Ile Ser Gln Val Leu Asp Cys Ile
            100                 105                 110

Asp Arg Leu Asn Val Tyr Ser Thr Ala Ala His Phe Ala Glu Phe Ala
            115                 120                 125

Gly Glu Glu Ala Ala Glu Ser Trp Lys Glu Ile Val Asn Leu Leu Tyr
130                 135                 140

Glu Leu Leu Ala Ser Leu Ile Arg Gly Asn Arg Ser Asn Cys Ala Leu
145                 150                 155                 160

Phe Ser Asn Asn Leu Asp Trp Val Val Ser Lys Leu Asp Arg Leu Glu
                165                 170                 175

Ala Ser Ser Gly Ile Leu Glu Val Leu Tyr Cys Val Leu Ile Glu Ser
            180                 185                 190

Pro Glu Val Leu Asn Ile Ile Lys Asn His Ile Lys Ser Ile Ile
            195                 200                 205

Ser Leu Leu Asp Lys His Gly Arg Asn His Lys Val Leu Asp Val Leu
            210                 215                 220

Cys Ser Leu Cys Val Cys Asn Gly Val Ala Val Arg Ser
225                 230                 235
```

<210> SEQ ID NO 12
<211> LENGTH: 237
<212> TYPE: PRT
<213> ORGANISM: Makaira nigricans

<400> SEQUENCE: 12

```
Ile Leu His Lys Glu Gly His Met Asp Asp Ala Leu Thr Val Ala Arg
1               5                   10                  15

Ser Gln Thr Glu Glu Ala Gln Ala Ala Arg Met Ile Tyr Ser Thr Thr
                20                  25                  30

Gly Leu Phe Asn Gln Phe Ile Lys Gly Leu Asp Thr Leu Ser Gly Lys
            35                  40                  45

Asn Lys Ser Ala Asn Pro Pro Ser Leu Pro Met Asp Thr Val Val Leu
50                  55                  60

Ser Leu Gln Asp Leu Ile Phe Tyr Phe Arg Pro Gly His Glu Leu
65                  70                  75                  80

Glu His Glu Asp Lys Gln Phe Lys Leu Arg Ser Leu Lys Asn Arg Gln
                85                  90                  95

Asn Leu Phe Gln Glu Glu Gly Met Ile Thr Leu Val Leu Asp Cys Val
            100                 105                 110

Asp Arg Leu Asn Val Tyr Asn Thr Ala Ala His Phe Ser Glu Tyr Ala
```

-continued

```
            115                 120                 125
Gly Glu Glu Ala Ala Glu Ser Trp Lys Glu Ile Val Asn Leu Leu Tyr
    130                 135                 140

Glu Leu Leu Ala Ser Leu Ile Arg Gly Asn Arg Ala Asn Cys Ala Leu
145                 150                 155                 160

Phe Cys Asp Asn Leu Asp Trp Leu Val Ser Lys Leu Asp Arg Leu Glu
                165                 170                 175

Ala Ser Ser Gly Ile Leu Glu Val Leu Tyr Cys Val Leu Ile Glu Ser
            180                 185                 190

Pro Glu Val Leu Asn Ile Ile Gln Glu Asn His Ile Lys Ser Ile Ile
        195                 200                 205

Ser Leu Leu Asp Lys His Gly Arg Asn His Lys Val Leu Asp Val Leu
    210                 215                 220

Cys Ser Leu Cys Val Cys Asn Gly Val Ala Val Arg Ser
225                 230                 235
```

<210> SEQ ID NO 13
<211> LENGTH: 26
<212> TYPE: DNA
<213> ORGANISM: Artificial Sequence
<220> FEATURE:
<223> OTHER INFORMATION: Synthetic

<400> SEQUENCE: 13
ctgcaccagg agggccacat ggacga           26

<210> SEQ ID NO 14
<211> LENGTH: 28
<212> TYPE: DNA
<213> ORGANISM: Artificial Sequence
<220> FEATURE:
<223> OTHER INFORMATION: Synthetic

<400> SEQUENCE: 14
cggtccagtt tgcaccagcc agtccagg         28

<210> SEQ ID NO 15
<211> LENGTH: 24
<212> TYPE: DNA
<213> ORGANISM: Artificial Sequence
<220> FEATURE:
<223> OTHER INFORMATION: Synthetic

<400> SEQUENCE: 15
gacgcgtgtc gctcagccgc tcgc             24

<210> SEQ ID NO 16
<211> LENGTH: 26
<212> TYPE: DNA
<213> ORGANISM: Artificial Sequence
<220> FEATURE:
<223> OTHER INFORMATION: Synthetic

<400> SEQUENCE: 16
ccagcagctc atagaggagg ttgacg           26

<210> SEQ ID NO 17
<211> LENGTH: 14620
<212> TYPE: DNA
<213> ORGANISM: Meleagris gallopavo

<400> SEQUENCE: 17

```
atggctgaag ggggtgaagg aggagaagat gaaatacagt tcctacgaac tgatgacgaa    60
gtagtacttc agtgtgtttc cagtattcac aaagaacaaa ggaagttttg cttggcagct   120
gagggacttg gaaatcgctt gtgcttttg gaaccaacgt cagaagctaa atatgttcct   180
ccagaccttt gcatctgtaa cttttgtcctt gaacagtctc tgtctgtaag agcccttcaa   240
gagatgctga ccaacacagg ggataatgcc agtgaagggg cagctcaagg tggtcacaga   300
actttgctgt atggccatgc tatactactt cgacattcat tcagtgaaat gtatttaact   360
tgcttaacat catcaagatc ccagactgat aaacttgcat ttgatgtggg actacgagaa   420
aatgcagcag gtgaggcatg ctggtggacg atacaccctg cttctaaaca agatcagaa   480 ggagaaaaag ttcgaatagg tgatgatctt atcctggtta gtgtgtcctc tgaaagatac   540
ctgcatctct ccatgtcaaa tggaagtatt caggtggacg cctccttcat gcagacactt   600
tggaatgtac atcctacatg ctcaggaagc aatattacag aaggatatct tcttggtggg   660
catgtagtac gttttttcca tggtcatgat gagtgtttga caattccttc tacagatcag   720
aatgattcac agcagaagaa agtactttat gaaactggag gagcaggtgt tcgagcgaga   780
tctttgtgga gagtagaacc ccttcgaata agttggagcg gaagtaacat cagatgggga   840 cagccttttcc gtcttcgaca tataacaaca ggaatgtact tggctttgaa tgatgatgaa   900
ggtcttgtaa tgttggacag agaaaagtca gacacaacat cttctgcttt ttgtttcaga   960
gcatcaaagg aactaaaaga aaagcaggat tctactctta acgtgacat tgatggaatg  1020 ggagtcccag aaataaaata cggtgattca gtctgttttg ttcaacatgt agccagtgcc  1080
ttatggctga cttataaagc accagatgct aaatcagcac gcttagggct cctgaaaaga  1140
aaggttatat tacaccagga aggtcatatg gatgatggtc taaccttaca aagatgtcaa  1200
catgaagaat cacaggctgc tcgaatcatt cgcaatacta caagcttatt cagccagttt  1260
ataagtggga caacagaac actatcaccc attgccctgc ctgttgagga gatggctcag  1320
actctgcaag acctgatcaa gtacttccag cctcctggag aagacctgga acatgaggat  1380
aagcaaaaca gcttcggtc cctcaaaaac agacaaaacc tattcaaaga tgagggaatg  1440
ctggcactag ttttgaattg catcgatcgt ttaaatgact acaacagtgc agctcatttt  1500
gcagaaattg caagaagaa aaatagtaca gcatggaaag aaattttaaa tctcctttat  1560
gaactgcttg ctgctctcat tcgtggcaac agaaacaatt gtactcagtt ctccagtaac  1620
cttgattggc taataagcaa attggacaga ctggaatctt cctcaggtat tttggaagtg  1680
ttgcactgta tcttgattga aagtccagaa gctttaaatg tgatagctga ggagcatata  1740
aaatctatta tttcactgtt ggacaagcat gggcgcaatt acaaggttct tgatgtgctt  1800
tgctctcttt gtgtgtgtaa tggagttgca gttcgtgcca atcaaaactt gatctgtgac  1860
aatctactgc caagaagaga cttacttttg caaacacgtt tgattaatga tgtgacaagc  1920
ataaggccaa acatatttttt gggtgttgct gagggctctg cacaatacaa gaagtggtac  1980
tttgaattaa taattgatca ggttgatcca ttcttgacgg cagaacccac ccatttacgg  2040
gttgggtggg cttctacttc aggttatgcc cctatcctg gaggtggaga aggatggggt  2100
ggcaatggcg ttggagatga cctatattcc tttggttttg atggccttca tctgtggtct  2160
ggtcgtgtac ccagagctgt ggcatctgtc aatcaacatt tgctgtcatc tgatgatgta  2220
gttagctgct gcttggattt aggtgtgccc agcatttcat tccgcattaa tggtcagcct  2280
gtacaaggaa tgtttgagaa cttctgtact gaagggtttt tcttccctgt tgtaagctta  2340
tcagcaggtg taaaagctcg tttcttactg ggtggacgtc atggagagtt taaatttctg  2400
```

```
cctcctgctg gctatgctcc ctgttatgaa gccttgcttc caaaagaaaa gatgaaattg    2460
gaaccagtga agaatataa gagagattct gatggagtga gagatttgct gggtacgaca     2520
caattcctct cccaagcttc atttatacct tgtcctatag acaccagtca gattgctctt    2580
ccttttcatc ttgaaaagat cagggataaa ctagcagaaa atatccatga actgtgggga   2640
atgaataaaa tagagctggg ctggacatat ggcaagatac gggatgataa taaaaggcat   2700
catccttgtc ttgtggaatt ctcaaagtta cctgagacag agaagaatta taatctacaa   2760
atgtcaacag aaaccctcaa aacgcttttg gcccttggat gtcacattgt tcatgctaat   2820
ccagcagctg aggaagatct taaaaaagtc aagcttccta aaaattatat catgtcaaat   2880
ggttataaac ctgcccctct tgatctttct gaagtgaaat tgttaccttc tcaagaattt   2940
ctagttgaca aactagcaga aatgcacat aatgtctggg caaaagacag aataaagcaa    3000
ggatggacct atggcattca gcaggatctt aagaacaaac gtaatcctcg gctagtgcca   3060
tatgcattac tagatgaacg tactaaaaaa tcaaacagag atagcctccg tgaagctgtt   3120
aggacatttg caggctatgg ttataatatt gagccacctg accaagaaat agctgaccaa   3180
acattggaaa aagtcagcat tgacaagata cgttttttca gagtagaaca gtcttatgca   3240
gtgaagtctg gaaagtggta ttttgaattt gaagctgtaa caggtggaga tatgcgtgtt   3300
ggctgggcca ggccaggctg tcgacctgac attgaactgg gagctgatga ccaagcattt   3360
gtttttgaag gaagcaaagg ccagcgttgg catcaaggca gtgggttttt tggacgaagt   3420
tggcaaccgg gagatgtggt tggatgcatg ataaacttgg atgacaaatc aattatcttt   3480
actctgaatg gagagttgct tataaccagt aaaggttcag aacttgcatt tgctgacttt   3540
ggaatagaaa gtggttttgt tccaatttgc tcactgggtc tagctcagat tggacgtatg   3600
aaccttggaa tggatgccag tacattcaag tattatacca tgtgtggtct tcaagaaggt   3660
tttgaacctt ttgcagtgaa catgaaccga gatgtcgcta tgtggtttag taaacgctta   3720
ccaacatttg ttaatgtgcc aaaaaatcat cctcacatag agatatggag aattgatgga   3780
accattgaga gtccacctcg gttaaaagtt actcacaaaa cacttggtac acaaaacagc   3840
aattctgata tgatatattg tcgtttgagt atgcccattg agttccgttc atcattcaac   3900
tttggcgtgg gtgtggaaaa tgcctcatct gatgctcttc aaaaacgaaa acacagccaa   3960
gaatttcctg cttcttctac cacatatttt tattccttac ggatatttgc tggccaagac   4020
ccatcttctg tctgggttgg ttgggtaaca ccagactatc attttacag tgagaatttt    4080 gacataaaata aaaactgtac agtgacagtt actttaggag atgagagagg cagggttcat   4140
gaaagtgtga agcgcagtaa ttgctatatg gtttggggag gagatataac tgctaattct   4200
cagagatcag gtcgcagtaa tgttgattta gaaattggat gctttgttga cctggctact   4260
ggaatgttgt cattcactgc caatggaaaa gagcttggca cttgttatca ggttgaacca   4320
aacacaaaac ttcttcctgc agcttttgta cagcctacaa gcactaactt aattcagttt   4380
gaacttggta aattaaagaa taccatgccg ttatcagcag caattttaaa agtgaggaa    4440 agaaatcctg ttcctcagtg tcccctcgc cttgatgtgc aaacaattac acctgtttta    4500
tggagtagga tgcctaacag cttctaaaa gtagaaacag agcgcgtgag tgaacgtcat    4560
ggctgggttg tgcagtgttt ggaaccactg cagatgatgg cacttcatat cccagaggag   4620
aacagatgtg tggatatttt ggaactatgt gaacaagaag atttgatgaa gtttcactat   4680
cacactttaa aactttatag ctcagttttgt gctctaggta acactagagt tgcttatgca   4740
```

```
ctttgtagcc atgtagatat atctcagtta ttttacacaa tagataatca gtatttacct    4800
ggactcctac gttctggatt ctatgacttg ctcattagta ttcatttgga ccatgccaag    4860
caagccaagc tcatgatgaa caatgaattt attattccag ttacagagga aactcgaact    4920
attaaattat atcctgatga aacaaagaag catggtttac ccggagtagg gcttagcact    4980
tgtctcaaac caagctttaa ttttctact ccttgcttta ttgtgacctc ggaagaacat     5040
cagacatcca gcccagaaat tccccttgac acacttaaat ccaaagcgat aagtatgctg    5100
acagaggcgg tacagtgcag tggttctcat atacgagatc ctgttggagg acatattgca    5160
ttccagtttg ttcctgttct taaactcata gcaacattgc ttataatggg agtttttgat    5220
gatgatgatg tgaagcaggt gttaatcctc attgatccca atgtctttgg agataacaag    5280
gaagaaacag aagagaggac agagaaggaa gaagttacac aagttgaaga aaaagctgta    5340
gaagctggag aaaaggcagt aaaagaaaca aaaacaccta caagggctt attgcagaca     5400
agattaccag aatctggtaa gcttcagatg tgccacttac tcaattattt ctgtgactgc    5460
gagctgcaac atagagtgga agcgattgta tcatttgcag accactatgt atcaaaactg    5520
caatataatc agaagtacag gtataatgaa ctcatgcaag ccttggacat gtctgctgct    5580
ttgactgcca agaagactaa ggaatttcga tctcctccac aagaacagat taatatgctg    5640
ctgaattttc aactgggaga ggattgtccc tgtccagaag agattcggga tgaactatat    5700
gacttccatg atgatcttct aattcactgt ggtattccac tagaagagga ggaagaggaa    5760
gaggaagatt cctccttgac tggcaagctt cgttcattaa tatacaaaat caaaggtcca    5820
ccaaaaccag aaaaaataga gcccagagaa gaagaagata aatcgcctac tacactgaag    5880
gaactcatat cccaaactat ggtgcgctgg tcccaggaag atcagattca agatccagaa    5940
ttggttcgga ttatgtacac tctgctgcgt aggcaatatg atagcattgg tgagctactt    6000
caagctctga ggaaagcata cactattagt gctggctctg tgaaggatac cattaatctg    6060
cttgctgcac tgggccagat tcgctcactt ctcagtgtaa gaatgggaaa agaagaggaa    6120
ctgctaatga ttaatggatt aggagatatc atgaacaaca aggttttta tcagcatcct      6180
aacttaatga gagtcttggg catgcatgag acagttatgg atgtgatggt gaatgtgctt    6240
ggaggagata aatctcagat cgttttcct aagatggtgg caagctgttg tcgatttctg      6300
tgctacttct gtcgaattag tcgtcaaaac caaaaagcca tgtttgagca tctcagttac    6360
ttactggaaa acagcagcgt tgggttggca tttccttcaa tgagaggttc gacaccactt    6420
gatgttgcag cagcctctgt aatggacaac aatgagcttg cactagcact ggaagaacca    6480
gatcttgata agttgttac ttacctggca ggttggggcc tgcagagatg tccagtgttg      6540
ctagctaaag gatatccaga cattgggtgg aatccaatag agggtgaacg ttacctgtca    6600
ttcctaagat ttgcagtttt tgttaacagt gaaagtgttg aagaaaatgc aagtgttgtt    6660
gtaaagcttc ttattcgacg accagagtgc tttggaccag agcttagagg agaaggagga    6720
aatggattgc tggcagctat gcaagaagct atacggatct cagagaatcc ttctcgtgac    6780
cttccctcac aaggatataa agagaaggt gatgaagagg aggaggagga ggagatcgta      6840
cacatgggca atgcaatcat gtcattttac tctgctctca tagatttact tggacgctgt    6900
gcaccagaaa tgcaccttat tcaaagtgga aaaggtgaag ctattcgaat cagatcaatc    6960
cttcgatctc tagtgccaac tgaagatttg gttgggatta taagtatacc actaaagctg    7020
tcaacagtta acaaagatgg cactgtaaat gagccagaca tgtctgcaaa tttctgtcct    7080
gatcataagg caccaatggt actcttttg gaccgtgtgt atggcattaa ggaccaaagc     7140
```

```
ttcctccttc acctacttga agttggattt ttaccagatt taagagcttc tgcctctctg    7200
gatacagttt ctctaagtac cacagaagca gctcttgcac taaacagata tatttgctca    7260
gctgtgtttc cgttactcaa aagatgtgct cccctctttt ctggaacaga acatcatgcc    7320
tctcttgttg actccatgct tcacacaata tataggttat ccaaaggacg ttcccttaca    7380
aaagcacaac gagacactat tgaagaatgc ctgcttgcta tctgccacca cttacgtccc    7440
tctatgctcc aacagctatt gagaaggcta gttttgatg tgcccttact caatgaatac    7500
tgtaaaatgc cactcaagct tctgacaaat cactatgaac agtgttggaa atattattgt    7560
ctaccttcag gaatgggaag ctatggaatt gcagcagaag atgaattaca tttaactgaa    7620
aaactttttt ggggaatatt tgattccttg tctcataaga agtatgatcc agagctcttt    7680
agaatggcct tgccctgcct aagtgctata gctggggctt tgcctcctga ttatttagat    7740
acacgaatta gatcaacatt ggaaaagcag acctcagtgg atccagaagg aaattttgat    7800
cccaaaccca tcaacacagc aaaccttgta cttcctgaaa agctggagta tattgtcagc    7860
aaatatgctg agcattctca tgataaatgg gcttttgata agactaataa tgggtggaaa    7920
tacggtgttt cactggatga aaatacaaag actcatccat taataagacc tttcaaaact    7980
ttaactgaga aggaaaaaga aatttatcgt tggcctgtga gagaatccct gaaaaccatg    8040
ttggccatgg ggtggagcct cgaaaggacc aaggaagggg cgaaggaat gttacatcag    8100
cgtgaaaatg aaaagctccg cagcatatct cagtctagcc agggaaatgg atatagccca    8160
gcaccacttg atctcactaa cgtggtactt tctaggaaac ttcagggaat ggttgaggta    8220
atggcagaaa actaccataa tatatgggcc aaaaagaaga aatggagtt ggaaagcaaa    8280
ggtggaggca gtcatccttt attggtacct tacgacacat tgacagccaa ggagaaatca    8340
cgggaccgtg aaaaggcaca agagctgttt aaattccttc aagtgaatgg cataatcata    8400
tctcggggtc tgaatgacat ggatttggat gcttcatcca tggaaaagag gtttgccttt    8460
aagtttctga agaaaatttt aaaatatgtt gactctgctc aagagttcat tgcacatttg    8520
gaagccattg ttactagtgg aaaaactgaa aaatccccgc atgaccaaga ataaaaattc    8580
tttgccaaag ttcttttacc attagttgat caatacttta caaatcactg cttgtacttc    8640
ctgtcttctc caacaaaaac actcagtagc agtggatatg catcaaataa ggaaaaggaa    8700
atggtagcaa gcctgttctg caaactagct gctcttgtta gacataggat ctcaattttt    8760
ggtagtgatt ctcaacaat ggtgagctgc ctgcacatct tagctcagtc tctggatact    8820
cgaactgtta tgaaatcagg atctgagcta gttaaagctg gactacgtgc ttttttgaa    8880
aatgcagctg aagatctgga aaaaacttca gaaaatctta aacttggaaa atttacacat    8940
tcacgaacac aaatcaaagg tgtttcacag aacatcaatt atactacagt agcattgcta    9000
cctgtcttga cgtcaatttt tgagcatatt tcacagtatc attttggagt tgatttactt    9060
ctgggtgatg tacaagtttc atgttacaga attctttgta gcctctattc tcttgggact    9120
gggaagaaca tctacgttga aaggcaacgt cctgcacttg gtgaatgctt agcatctttt    9180
gcagcagcca ttccagtagc attccttgaa ccttctctca accactacaa cccattgtct    9240
gtcttcaaca caaaaagtgc aagagaaaga gcaattttag gtatgcctga tacagtagag    9300
gaaatgtgtc cagaaatccc tcagctggat ggactaataa aggaaattaa taatttagca    9360
gagtctggag caaggtatac tgaaatgcct cacgtaattg aggttatctt acccatgctg    9420
tgcaattatt tgtcctactg gtgggaacga gggtctgaga gtgttcctga aagtgctggc    9480
```

```
ccttgctgta cgatgataac atctgagcat ctgagcatca ttctgggaaa tattctgaaa    9540
atcattaaca ccaatctggg aatagatgaa gcatcttgga tgaaaagaat tgcagtttat    9600
gctcaaccta tcatcagcaa agccagacct gatctgctga aaactcactt tattccaaca    9660
ctggagaaat tgaagaagaa agctataaag attgtgatgg aagaggagca actgagagca    9720
gacagtaaaa gtgacactca agaagctgag ctacttattc tcgatgagtt tgctgttctt    9780
tgtagagacc tctatgcctt ctatccaatg ctgatacgtt acgtagacaa caacagagcc    9840
aactggctaa agaaaccaga tgcagattct gatgaactgt ttcgaatggt agctgaagtt    9900
tttatcctgt ggtgcaagtc acataatttc aaaagagaag aacaaaattt tgtcatacag    9960
aatgaaatca acaatttggc attttaaca ggagatacca aaagcaagat gtctaaagcc    10020
atgcaagtaa agtctggagg tcaagatcaa gagagaaaga aatcaaaacg caggggggat    10080
ttgtactcca tacaaacatc cttgattgta gctgcactta aaagatgct tcctattggc    10140 ttgaatatgt gtactccagg agatcaagag ctcatctcat tggctaagac tagatatagc    10200
cataaggaca ctgatgaaga agtcaaagag catatacgta acaatttaca tctgcaggaa    10260
aagtctgatg atccagctgt gaaatggcag ttaaatctat ataaagacat tctgaagagt    10320
gatgagcctc ctgaccctga gaaaaatgtg gaacgtgtgc agaggatatc agctgctctg    10380
tatcatctgg accaggttga acaaccactg agatcaaaga aagctgtttg gcacaaactt    10440
ctgtcaaaac aacgcaaaag agctgttgtt gcttgtttta gaatggcgcc gttatacaac    10500
ttacccaggc accgttctat taacctcttc ctccatggct atcagaacta ttggatagaa    10560
acagaggaat attcatttga ggagaaacta gttcaggatt tggctacgtc tccaaaaaaa    10620
gaggaagaag aagaggaaga tacagagaaa gaacaacctg acccacttca tcagattatc    10680
ctctatttta gtcgcaatgc tctcacagag aggagcaaac tagaagatga tcccttatat    10740
attgcctatg ctgccatgat ggcaaagagc tgtcaggaag aagaagaaga ggaggaggaa    10800
gacaaagaga agacatttga ggagaaagaa atggaaaagc agagaactct ttatcagcaa    10860
gctcgcttac atgatcgtgg agctgctgag atggtccttc agatgatcag tgcaagcaaa    10920
ggtcatacag gacccatggt tgttgaaaca ctaaaacttg gtattgctat tctaaatggt    10980
gggaatacaa tagttcaaca gaaaatgcta gactacttga aggagaaaaa ggatgctgga    11040
ttctttcaaa gtctttctgg tttgatgcag tcctgcagtg ttcttgactt gaatgcgttt    11100
gagagacaaa ataaagcaga aggcctggga atggttactg aagaaggaac tctcatcgta    11160
cgtgagcgtg gtgaaaaagt gttgcagcat gatgaattta ctcgagatct atttagattt    11220
ttacaactgc tctgtgaagg gcataacaat gattttcaaa attatctacg cactcagatg    11280
ggcaacacca caacagtgaa tattatcatt agtacagttg actacctctt gcgtcttcag    11340
gaatcaatca gtgacttcta ttggtactat tcaggaaaag agtttattga tgaatcagga    11400
caacgtaact tctctaaagc tctggctgtc accaaacaaa tattcaattc ccttaccgaa    11460
tatatacagg gaccttgcat cggtaaccaa cagagtctgg ctcatagtag gctgtgggat    11520
gcagttgttg gatttcttca tgtatttgcc aatatgcaga tgaaactttc acaggactct    11580
gctcagattg aactgcttaa ggaactgcta gatctgctaa aggatatggt tgtgatgttg    11640
ttgtcattac ttgaaggtaa cgttgtaaat ggaacaattg gaaaacaaat ggtcgataca    11700
cttgtagaat catctagcaa cgtagaatta atcttgaagt ttttttgacat gtttctcaaa    11760 ttaaaagatt taactaactc ggatgctttc aaggagcatg acccagatgg taagggcatc    11820
atttcaaaga aggatttcca gaagtcaatg gaggctcaaa aacaatatat acaatcagag    11880
```

```
attgaattcc tgttgtcatg tacggaagct gatgaaaatg atatgttcaa ctacattgat    11940
tttgtagaaa gattccatga accagccaaa gatattggct ttaatgtagc agttttgcta    12000
acaaaccttt cagagcatat gcctaatgac tcacgccttc agagcttact tgaacctgca    12060
gaaagtgttc ttaattactt tgaaccatac cttggccgta ttgaaataat gggtggagcc    12120
aagaaaatag aaagagttta ctttgaaatc agtgaatcca gtagaatgca gtgggaaaag    12180
ccacaggtga aggaatccaa aaggcaattc atatttgatg ttgtaaacga aggtggagag    12240
caagaaaaaa tggagctctt cgtgaacttc tgtgaagaca cgatctttga aatgcagtta    12300
gcatcccaaa tctctgagac tgattcagct gagagacctg aggaagagga agaagagcct    12360
tgctacattg tggatatcgg agatgatgag gaagaagaaa agtccctgga atctccttca    12420
gcttttgcaa tggcctgtgc tgcagtcaag aagaacgtcg ccaactttt taaaatggtt    12480 actgtgaaga acctaaggaa acagtacagg aaagtcagaa agatgacagt aaaagagatg    12540
gtgaaagtgt ttttctcttt tttctggatt ctatttgtag gggtgttcca actgtttttt    12600
actatagtat ggggaatttt ccagattctt tggagcaccg tatttggggg tggactggtt    12660
gaaggagcca aaaatattaa agttactaaa atactagggg acatgcctga cccaacgcag    12720
tttggaatcc atgatgatgt cacagaagca gaaaaaactg aaggtgctga gcatggcatt    12780
agagatgaac ttgtgcagtt tgtaaagggt gaaaaggggag aagctgacat aatttcagat    12840 attttttggca ttcctactaa gaaagaaggt ggctcaaaac atggtcatga cgctggactt    12900
ggagatattg cagaaatact tggctctgat atccagtctt ctctggaaaa caatgttcgt    12960
aagaaaaaag gattacagac acctgaaact gcaaagacg ctgaagcaga agaaaagta    13020 gaagctgaga aggctgacat ggaagatggt gagaaacagg ataaagcaaa ggaagaacac    13080
tctgagcagc aggaagaggg aaaaacaaag aaaagaagc gaaggcatgg acaaaaaatt    13140
gagaaacctg tggctgttat ggctaatttc ttcaaagctt tggaaatata tcaaacaaaa    13200
atgcttcact acctggcaag gaacttttat aacttacggt ttcttgctct atttgttgca    13260
tttgccatca actttattct gctatttac aaggtgacag aagagccact tgatgaagtg    13320
gaggaagact ctaatctctg gaactctttt gaagaagagg aagaggagga aggaatggta    13380
ttttttgttt tggaagaaag tacaggttac atggcaccta ctctcagagc actggcagtt    13440
attcatacta tcatctcctt tgtctgtgtg attggatact attgcttaaa ggtccctttg    13500
gttgtattca agagagaaaa ggaggtagct aggaagctgg aatttgatgg attatacata    13560
actgaacaac catctgaaga tgatattaaa ggacagtggg atcgcctggt tataaacaca    13620
ccgtcctttc ctaacaatta ctgggataaa tttgtaaaac gaaaggttat taacaagtat    13680
ggagacttgt acggagcaga gcgtatagca gaacttttgg gtttggacaa aaatgcccttt    13740 gattttagtc cagtggaaga gagcgaacca gaagcggcat ctcttgtatc atggttaagt    13800
tccattgata caaagtacca catttggaag cttggtgttg ttttcactga taattcattt    13860 ttgtattgg cttggtacac aactatgtct atccttggac actacaacaa cttctttttt    13920
gctgctcatc tgctggacat cgctatgggt ttcaagacat tgcgaaccat tttgtcctct    13980
gtaactcaca atggcaaaca gcttgtgctt actgtaggac tcctggctgt agtagtgtat    14040
ctttacactg ttgtggcatt caacttcttc cgcaaaattct acaataaaag tgaagatgaa    14100
gatgaaccag atatgaaatg tgatgacatg atgacgtgtt acctattcca catgtatgtg    14160
ggtgtaagag ctggtggtgg cattggggat gaaattgagg atcctgctgg agacccttat    14220
```

```
gaaatttatc gaattgtctt cgacatcaca ttttcttct tgtcattgt catcctactg    14280 gccattattc aaggtctgat tattgacgct tttggtgaat aagagacca gcaagaacaa   14340 gtgagagaag atatggagac caaatgcttt atttgtggaa ttggcaacga ctattttgac   14400
acaactccac atggctttga acacatact ctgcaggaac acaacttggc aaactacctg    14460
ttcttcttaa tgtacctcat aaacaaggat gagactgagc atactggcca ggagtcattt   14520
gtgtggaaga tgtaccaaga aagatgctgg gatttcttcc cagcaggaga ctgcttccgg   14580
aaacagtatg aggatcaact cggcaatcga attcccgcgg                          14620
```

<210> SEQ ID NO 18
<211> LENGTH: 717
<212> TYPE: DNA
<213> ORGANISM: Meleagris gallopavo

<400> SEQUENCE: 18

```
attctgcacc aggagggcca catggacgac gcgctgtcgc tcagccgctc gcagggcgag     60
gagtcgcagg cggcgcggat gatttacagc acggcggggc tctacgggag cttcatccgg    120
agcctggacg cgctgagctc tcggggccgc ggcggcggtg cggggaacgc ggctctgccc    180
atcgccgccg tcatcctcag cctgcgggat ctgatcgctt atttccgcgc cccgcacacc    240
gagctgcagc acgagcagcg ccagaaccgc ctgcgctccc tgcggcgccg ccaggacctc    300
ttccagcagg aggggatgat ctccctggtg ctgaactgca tcgaccggct gaacgtgtac    360
agcacggccg cgcacttcgc cgagttcgcc ggggaggagg cggcggccgc ctggaaggag    420
atcgtcaacc tcctctatga gctgctggcg tcgctgatcc gggggaaccg aaccaactgc    480
gccctgttct ccaccaacct ggactggctg gtcagcaaac tggaccggct ggaggcgtcg    540
tcagggatcc tggaggtgct ttactgcgtc ctgatcgaga gccccgaggt tctgaacatc    600
atccaggaga accacatcaa gtccatcatc tccctgctgg acaaacacgg ccgcaaccat    660
aaggtcctgg acgtgctctg ctctctgtgt gtctgcaatg ctgtggccgt tcgttcc       717
```

<210> SEQ ID NO 19
<211> LENGTH: 636
<212> TYPE: DNA
<213> ORGANISM: Meleagris gallopavo

<400> SEQUENCE: 19

```
attctgcacc aggagggcca catggacgac gcgctgtcgc tcagccgctc gcagggcgag     60
gagtcgcagg cggcgcggat gatttacagc acggcggggc tctacgggag cttcatccgc    120
ctgcgggatc tgatcgctta tttccgcgcc ccgcacaccg agctgcagca cgagcagcgc    180
cagaaccgcc tgcgctccct gcggcgccgc caggacctct tccagcagga ggggatgatc    240
tccctggtgc tgaactgcat cgaccggctg aacgtgtaca gcacggccgc gcacttcgcc    300
gagttcgccg gggaggaggc ggcggccgcc tggaaggaga tcgtcaacct cctctatgag    360
ctgctggcgt cgctgatccg ggggaaccga accaactgcg ccctgttctc caccaacctg    420
gactggctgg tcagcaaact ggaccggctg gaggcgtcgt cagggatcct ggaggtgctt    480
tactgcgtcc tgatcgagag ccccgaggtt ctgaacatca tccaggagaa ccacatcaag    540
tccatcatct ccctgctgga caaacacggc cgcaaccata aggtcctgga cgtgctctgc    600
tctctgtgtg tctgcaatgc tgtggccgtt cgttcc                              636
```

<210> SEQ ID NO 20
<211> LENGTH: 524

```
<212> TYPE: DNA
<213> ORGANISM: Meleagris gallopavo

<400> SEQUENCE: 20
attctgcacc aggagggcca catggacgac gcgctgtcgc tcagccgctc gcagggcgag      60
gagtcgcagg cggcgcggat gatttacagc acggcggggc tctacgggag cttcatccgg     120
ggatgatctc cctggtgctg aactgcatcg accggctgaa cgtgtacagc acggccgcgc     180
acttcgccga gttcgccggg gaggaggcgg cggccgcctg aaggagatc gtcaacctcc      240
tctatgagct gctggcgtcg ctgatccggg ggaaccgaac caactgcgcc ctgttctcca     300
ccaacctgga ctggctggtc agcaaactgg accggctgga ggcgtcgtca gggatcctgg     360
aggtgcttta ctgcgtcctg atcgagagcc ccgaggttct gaacatcatc caggagaacc     420
acatcaagtc catcatctcc ctgctggaca aacacggccg caaccataag gtcctggacg     480
tgctctgctc tctgtgtgtc tgcaatgctg tggccgttcg ttcc                      524

<210> SEQ ID NO 21
<211> LENGTH: 10129
<212> TYPE: DNA
<213> ORGANISM: Meleagris gallopavo

<400> SEQUENCE: 21
ctgccggcgg tgccgcgcct ggaggaggac gtggtgccgg acgagcggga cgaccccgat      60
gtcatcatga acagcaccac gtactacttc tcggtgcgga tctttgctgg ccaggacccc     120
tcccacgtct gggtgggcag ggtgaccccc gattaccacc agcacgaccc caacttcgac     180
ctgacgcgcg tccgcaccgt caccgtcacc atggggacg acaggggaa cgtgcacgac      240
agcatcagac gcagcagctg ctacatgctg tgggccgggg agttcggctc cgcttccccg     300
cagagccgca gccacagcga cgccgtcatc ggctgcctgg tggacgtggc cacggggctg     360
atgaccttca ccgccaacgg caaggagctc aacaccttct tccaggtgga gcccaacacc     420
aagctgttcc ccgccgtctt cgtgctgccc agcagtcagc acgtggtgca gttcgagctg     480
gggaagctga gaacatcct gccgctgtcg gccgcgctgt tcagcagcga gcgctgcaac     540
ccggagccgc agtgcccgcc ccggctgtgc atccagcgcc tgaccgccgt cacctggagc     600
cggatggcgg ccgaggagct gccgtgagc agcggccggg ccgccgacgg ccgcggctgg     660
gaggtgcgct gttccgaacc gcgcctgatg atggcgctgc acattccgga ggagaacaga     720
tgcatggaca tcatggagct gtgggagcgg caggacctgc tccgcttcca ttggcacacg     780
ctgaagctgt actgcgccgt gtgcgcgctg gcaacacgc gggtggcgca cgcgctgtgc      840
agccacgtgg atccgtcgca gctcctcttc gccatccgca gccgagct gcccggcccc      900
ctccgcgccg gttactacga cctgctgctg gccgtgcacc tggagcaggg cgtccgcgcc     960
cgggcctcca tgagcaccga gttcatcgtc cccatggacg aggcgtccaa acgcatctcc    1020
ctgttccccg ccggcggggg ggcgacgtc aaagtgcccg gccccccgg cgtcgggctc      1080
agcgcctgcc tccgccccg gccgcacttc gccgagccgt gcttcgtgcg gccgcccgac    1140
ggcagggcgc tgctgggtcc ctctatcccg ctgcgggcgc tgggcaggag ggccatcagg    1200
atgctgaggg aggcggtggc gggggggggg ccgcacgccc gggacccgt cggcggcggc    1260
gtggagttcc agctggtgcc ggtgttgaag ttggtgtcgg ctctgctggc cgtcggggcg    1320
ctgcgggacc cggaggtgcg caaggtgctg cggatgatcg aacccagggt gttcggggg     1380
ggcgaggagg aggaggagga ggagagagg aggaggagga ggaaggccgt ggaggccggc    1440
```

```
gaggaggagg aggaggtgga cgaggaggag gaggtagatg aggaggagga cgaggaggag    1500
gaggaggacg ggccggagga agggctgctg cagatgaagt tgccagagtc tgtgaagctg    1560
cagatgtgca acctactgca gttcttctgc gaccaggagc tgcagcaccg cgtggaagcg    1620
atcgtcgcct tctcggagcg ccacgtggag cggctgcagc gcgaccagag gcggcgctac    1680 ggcggctga tggggccgt gacgatgagc gcggctgaga ccgcgaggag aaccagggag       1740
ttccggtccc cccccagga acagatcaac atgctgctgc agtacaaggg ggggcggac      1800 gaggaggact gccccgtgcc ccccgacatc cgcgggagc tgctgcaatt ccacagcgac      1860
ctgctggcgc actgcggcat cgagctgcag ggcgaggagg aggaggagga ggaagacgcg    1920
tcgctgcggc agcggctgct ggccttggtg caacgcgtgg tggggaggca gcagaaggag    1980
gaggaggagg aggaggcgac gtccccagag ccccccgtgc cacgcaccct gcaggagctg    2040
atctcgcaca ccatggttca ctgggctcag gaatccttca tccagagccc cgagctggtt    2100
cgctccatgt tcagcctgct gcaccggcag tacgacgggc tggggagct ggtgcgggcg     2160 ctgcccaagg cttacaccat cagcgcccac tcggtgcccg acaccacggc gctgctcgag    2220
tgcctggggc agatccgctc gctgctcatc gtacagatgg ggcccgagga ggagaacctc    2280
atgatacaga gcatcgggaa catcatgaac aacaaagtct tctaccagca ccccaacctg    2340
atgcgggcgc tggggatgca cgagacggtc atgcaggtga tggtgagcgt gctgggcggc    2400
ggcgagacca aggagatccg cttccccaaa atggtcacca actgctgccg cttcctctgc    2460
tacttctgcc gcatcagccg ccagaaccag cgctccatgt tcgaccacct gggctacctg    2520
ctggagaaca gcagcatcgg cctgggcatg cagggctcca ccccattgga cgtggcggcc    2580
gcttctgtca tcgacaacaa cgagttggca ctggcactga aggagcagga cctggagaag    2640
gtggtgacgt acctggcgag ctgcgggctg cagagctgcc ccatgctgct gtccaagggt    2700
taccccgaca tcggctggaa cccctgcggg gggagcgct acctcgactt cctgcgcttc     2760
gccgtcttcg tcaacggtga gagcgtggag gaaaacgcca acgtggtggt ccggctgctg    2820
atccgacgcc ccgaatgctt cgggccggcg ctgcgcgggg aggggggcag cgggctgctg    2880
gccgccatcg aggacgccat taagatcagc gaggatccgg cacgggacgg ccccaccgtc    2940
aagaaggaga ggaggaggga gatattcggg gcagaggagc cccacgagga gaaccgcgtc    3000
cacctgggca acgccatcat gtccttctac gccgcctcga tcgacctgct gggccgctgc    3060
gcccccgaaa tgcacctgat ccaagcaggg aagggcgaag cgctgcggat ccgcgccatc    3120
ctgcgctccc tggtgccact ggatgacctg gtgggcgtca tcagcctccc cctgcagatc    3180
ccggccttcg ggaaagacgg gaacgtggtg cagccccgca tggctgccag ctttgtgccg    3240
gaccacaagg ctcccatggt gcttttcctg gaccgcgttt acggcatcga gacgcagcag    3300
ttcctgctcc acgtgctgga ggtcggcttc ctgcccgaca tgagaccggc cgcctccctc    3360 gacacggcg cgttcagcac gacgaagatg gcgctggcgc tgaaccgcta cctgtgcgtg     3420
ccggtgttgc cgctcatcac caaatgcgcg ccgctgtttg ccggcacgga gcaccgcgcc    3480
atcatggtgg actccatgct gcacaccatc taccgcctgt cgcgcggccg cgcgctcacc    3540
aaggcgcagc gcgacgccat cgaggagtgc ctgatggctc tgtgccggta catccggccc    3600
tccatgctgc agcacctcct gcgccgcctc gtcttcgacg tccccatcct caacgagttc    3660
gccaagatgc cgctcaagct gctgaccaac cactacgagc gctgctggaa gtattactgc    3720
ctgcccagcg ggtggcccaa ctacggggtc agctccgagg aggagctgca cctgacccgg    3780
aagctcttct ggggcatctt tgagtccctg gctcacaaga agttcgaccc cgagctgtac    3840
```

```
aagctggcca tgccgtgcct ctgcgccatc gcgggcgccc tgccccccga ctacgtggac   3900
gccagctact cctccaagac cgagaagaag gcgtcggtgg acgccgaggg caacttcgac   3960
cccaaacccg tcgagaccct caacgtcatc atccctgaga agttggacgg cttcatcaac   4020
aaatacgccg agttcaccca cgagaagtgg gcgttcgata agatccagaa caactggacc   4080
tacggggaga cggtggacga ggaggccaag acccaccccg tgctgcggcc ctacaagacc   4140
ttctcagaga aggacaagga aatttaccgg tggcccatca aggagtcgct gaaggcgatg   4200
ctggcgtggg agtggatggt ggaaaaggcg cgggagggcg acgaggagaa ggcggagaag   4260
aagaaaacgc ggaagatctc gcagtcggcg caggccacct acgacccag ccatggctac    4320 aacccgcagc ccgtggacct ctcggggtg acgctgtccc gagagctgca ggcgatggcg     4380
gagcagctgg ctgagaacta ccacaacacg tggggccgca agaagaagca ggagctggag   4440
gccaaagggg ggggctccca cccctgctg gtgccctacg acacgctgac ggccaaggag    4500
aaggcgcgcg accgcgagaa ggcgcaggag ctgctcaagt cctgcagct gaacggctac    4560 gccgtcacac gggggctgaa ggacatggag ttggacacgt cttccatcga gaagcgcttc   4620
gcctacggct tcctgcagca gctgctgcgg tggatggaca tctcccagga gttcatcgcc   4680
cacctggagg ctgtggtgag cagcggccgc gtggagaagt cgccccacga acaggagatc   4740
aaattctttg ccaagatcct gctgcccctc atcaaccagt acttccacaa ccactgcctc   4800
tacttcctct ccaccccgc caaagtgctg gcagcggcg ccacgcgtc caacaaggag      4860 aaggagatga tcaccagcct gttctgcaag ctggccgcgc tcgtccgcca ccgcgtcact   4920
ctctttggca ccgacgcgcc ggccgtggtc aactgcctcc acatcctggc acggtcgctg   4980
gacgccagga cggtgatgaa gtccggcccc gagatcgtga aggccgggct gcgctccttc   5040
ttcgagagcg cctcggagga catcgagaag atggtggaga acctgaagct gggcaaggtg   5100
acgcagagcc gcacgcaggt gaagggggtg gcccagaaca tcaactacac cacggtggct   5160
ctgctgcccg tcctcacgtc gctcttcgag cacatcgccc agcaccagtt ggggacgac    5220 gtcatcctgg acgatgtcca ggtctcgtgt taccgcatcc tgtgcagcat ttactccttg   5280
ggcaccacca ggaaccccta cgtggaaagg cagcgcccgg cgctggggga gtgcctggcc   5340
cggctggcgg ccgccatgcc tgtggccttc ctggagccgc ggctcaatga gttcaacccc   5400
tgctccgtct acagcaccaa gtcgccccgc gagcgtgcca accccatct tgggcact      5460 gcagaccccc accccatctt tgggaccca acaccagtcc tggggctgcc gagccacgtg    5520
gaggagatgt gccccgacat cccggacctg gagcgcctga tgaaggacat cgggggctg    5580 gcggagtcgg gcgctcgcta cacgagatg ccccacgtca tcgaggtgac gctgcccatg    5640
ctgtgcaatt atttgccccg ctggtgggag cgcgggccgg acagcagccc caggggccg    5700 tgggccacgg ccgtcaccgg gcagcacctg aacgccctgg ctgggaaaca tcctgcgcat   5760
cgtggtcaac aacctgggca tcgacgaggc gtcctggatg aaacgctggc agtgttcgct   5820
cagcccatcg tcagcaaggc gaagccggag ctgctgcgca cccacttcat ccccacgatg   5880
gagaagctga gaagcgggc agggaaggtg tgtcggagg aggagcagct gcgcatggag     5940
gcgaaggcgg aggccgagga cgccgagctg ctcatccgcg acgagttctc cgtgctctgc   6000
cgcgacctct acgccctgta ccctctgctc atccgctacg tcgacaacag ccgggccaag   6060
tggctgacgg agcccaacgc ggacgcggag gagctgttcc gcatggtggg agaggtcttc   6120
atctactggt ccaaatccca caactttaag cgcgaggagc agaactttgt ggtgcagaat   6180
```

```
gagatcaaca acatgtcctt cctgacggcc gacagcaaga gcaagatggc caagtccgga    6240
gacggccagg gcggtggctc ggagcaggag cgcaccaaga agaagcgccg cggcgaccgt    6300
tactccatcc acacctccct gatcgtggcc accctgaaga agatgctgcc catcggcctc    6360
aacatgtgct cccccaccga ccaggagctc atcagcctgg ccaagagccg ctacgccctg    6420
aaggacacgg atgaagaggt gcaggagtgc ctgaacaaca acctgcacct gcagggcaag    6480
tgtgagaact cgtcggccat gcgctggcag ctggctctgt atcgcgccat ggccggcagg    6540
gctgaggact ctgacagccc agagaaaatc gtgagacgag tgcaggaggt gtcagcagtg    6600
ctgtatcacc tggagcagac ggagcacccc tacaagtcca agaaggcggt gtggcacaaa    6660
ctgctctcca agcagcggcg ccgcgccgtg gtcgcctgtt ccgaatgac gccgctctac     6720 aacctgccca ggcatcgcgc ctgcaatatg ttcctggagg cctacaagct gctgtggttg    6780
gtgacggagg agcatccctt cgaggaccgc atgattgacg acctggcgaa atcaggggag    6840
gaggaggagg aggaggaaga ggagaaggac aagaagccag acccgctgca tcagctcatc    6900
ctgcacttca gccgcacggc gctgaccgag aaaagcaagt tggagaagga tcacctgtac    6960
atggcgtacg cgggtatcat ggccaagagc tgtcacattg aagaagggaa tgaagaggag    7020
aaggaggaga agaaggagga ggaggacccg gaggattcgt ttgaggagaa ggagatggag    7080
aagcagaagc tgctgtacca gcagtcgcgg ctgcacacga ggggagcagc tgagatggtg    7140
ctgcagatga tcagcgcctg caaagggggag cgggggggaga tggtttcctc cacgctgaag    7200
ttggggatct ccatcctcaa cggggggaaac gccgatgtgc agcagaaaat gttggattac    7260
ctgaaggaga aacgtgagat cggattcttc caaagcgtcc aggcgctgat gcagacctgc    7320
agcgtcctgg acctgaacgc ctttgagcgg cagaacaaag cggaggggct ggggatggtg    7380
acggaggagg ggacgatcat cagccgtgag aacggggaga aggtgatgtc ggatgatgag    7440
ttcacgcagg atctgttccg gctgctgcag ctgctgtgcg aggggcacaa caacgacttc    7500
cagaattacc tccgcacgca gacgggcaac accaccacca tcaacatcat catctgcacc    7560
gtggattacc tgctgcgcct gcaggagtcc atcagcgatt tctattggta ttactcgggg    7620
aaggacgtca tcgacgagca gggaaagcgc aacttctcca aggccatggc tgtggccaag    7680
caggtcttca acagcctcac cgagtacatc cagggtccgt gcacggggaa ccagcagagc    7740
ctggctcaca gccgcctgtg ggacgccgtg gtcggattcc tgcacgtctt cgcacacatg    7800
atgaagaagt tggcacagga ctccagccag atcgggctgc tgaaggagct gctggacctg    7860
cagaaggaca tggtggtgat gctgctgtcc ctgctggaag gcaatgtggt gaacgggacg    7920
atcgcacggc aggtggtgga catgccggtg gagtcgtcca gcaacgtcac catgatcctg    7980
aagttcttcg atatgttcct gaagctgcgc gacatcgtgg cctccgacgc cttccgcgat    8040
tacgtgacgg acccgcgggg gctcatctcc aaaaaggact tccagaaggc catggacagc    8100
cagaagcagt acgagccgtc cgaggtgcag ttcctgctct cgtgctcgga gcggacgag    8160 aacgagatga tcgacgtgga ggcgttcgtc gggcgctccc aggagccggc tcgcgacatc    8220
ggcttcaacg tggcggtgct gctgaccaac ctggccgagc acgtccccca cgaccagagg    8280
ctgcgcacct ttttggagca ggccgccagc atcctggagt atttccggcc gtttctgggc    8340
cgcatcgaga tcatgggagc ggcgcggcgc atcgagcgcc tctacttcga gatcagcgcg    8400
gccaacaagg cgcagtggga gatgccccag gaggatggaa aggaggtggt ggaggaaccg    8460
cagaaggagg aggaggaggc ggcggccgaa accgaaaagg ccgatacgga gaatggagag    8520
aagggcgatg ggggcgcaga gggggggtccg gaggtggaga cccccgaaaa gcagcagaag    8580
```

```
gcgtcgcccc cccgggagcg taaagagccc ccccgcccg aaggggcctt cgagttctgg    8640
acggagttgg aggtgcagag ggtgaagttc ctgaactacc tctcccgcaa cttctacaat    8700
ctccgcttcc tggcgctctt cctcgccttc gccatcaact tcatcctcct cttctataag    8760
gtgtcggagc ggccgccggg aatggaggag gcggagttgg aggggtcggg aatggcggcg    8820
gtgttggacg ggatcggaga cttcggggac ggcggggacg gggacggcgg ggacggggag    8880
gaggagccga gcgtggtgta ttactgcctg gaggagagca cgggctacat gcagcccgcc    8940
ctgcgcgccc tggccgtggc tcacaccatc gtggcgttcc tctgcatcat cggctacaac    9000
tgcctcaaga tcccctggt gatctttaag cgggagaagg aggtggcccg cgcctggag    9060 ttctcagggc tgtacatcac tgagcagccg ccggacgacg acgtgaaggg gcagtgggat    9120
cgcctggtcc tgaatgcgca gtccttccct agcaattact gggacaagtt cgtcaagaga    9180
aaggtgctgg agaaatatgg ggacatttat ggccgtgagc gcatcgcgga gctgctgggg    9240
atggagctct ccagcctcga aatcggggca cggggggaga ggaaaccccc ccccgacaac    9300
tccgtgctca cctggatcac cttcatcgat atccgctatc agatctggaa gtttggggtc    9360
atcttcactg ataactcgtt cctgtacctg acgtggtata tgggcatgtc ccttctgggc    9420
cactacaaca acttcttctt cgttgcacac ctcctggaca tcgccatggg ggtgaagacg    9480
ctgcgcacca tcctgtcctc cgtcacccat aatggaagca acctggccat gaccgtgggg    9540
ctgctggctg tcgtcgtgta tctttacacc gtcgtggcct tcaacttctt ccggaaattc    9600
tacaataaga gtgaagatga ggatgagccc gacatgaaat gcgacgacat gatgacgtgc    9660
tacctgttcc atatgtacgt gggggtccgc gccgggggg gcatcgggga tgaaatcgag    9720
gacccggctg gggatgaata cgagctgtac cgcgtggtct tcgacatcac cttcttcttc    9780
ttcgtcatcg tcatcctgct ggccatcatc caaggtctga tcatcgacgc cttcggggag    9840
ctgcgggacc agcaggagca ggtgaaggag gacatggaga caaaatgctt catctgtggc    9900
attggcagcg attactttga cacgacgccc cacggcttcg agacccacac gttggaggag    9960
cacaatttgg caaattacat gttcttcctg atgtatctga tcaataagga tgagacggag    10020
cacacggggc aggagtccta cgtatggaag atgtaccagg agcgctgctg ggatttcttc    10080
cctgccggtg actgcttccg caagcagtac gaggaccagc tgggctgac                10129
```

<210> SEQ ID NO 22
<211> LENGTH: 1056
<212> TYPE: PRT
<213> ORGANISM: Meleagris gallopavo

<400> SEQUENCE: 22

```
Met Gly Asp Gly Gly Glu Gly Asp Val Gln Phe Leu Arg Thr Asp Asp
1               5                   10                  15

Glu Val Val Leu Gln Cys Thr Thr Thr Leu Leu Lys Glu Gln Leu Lys
                20                  25                  30

Leu Cys Leu Ala Ala Glu Gly Phe Gly Asn Arg Pro Cys Phe Leu Glu
            35                  40                  45

Pro Thr Ser Asn Ala Gln Asn Val Pro Pro Asp Leu Ala Val Cys Cys
        50                  55                  60

Phe Val Leu Glu Gln Ser Leu Ser Val Arg Ala Leu Gln Glu Met Leu
65                  70                  75                  80

Ala Asn Cys Ala Glu Ser Gly Arg Glu Ser Ser Gln Gly Gly Gly His
                85                  90                  95
```

```
Arg Thr Leu Leu Tyr Gly His Ala Ile Leu Leu Arg His Ser His Ser
            100                 105                 110

Gly Met Tyr Leu Ser Cys Leu Thr Thr Ser Arg Ser Val Thr Asp Lys
            115                 120                 125

Leu Ala Phe Asp Val Gly Leu Gln Lys Asp Ala Ala Gly Glu Ala Cys
            130                 135                 140

Trp Trp Thr Leu His Pro Ala Ser Lys Gln Arg Ser Glu Gly Glu Lys
145                 150                 155                 160

Val Arg Val Gly Asp Asp Ile Ile Leu Val Ser Val Ser Ser Glu Arg
                165                 170                 175

Tyr Leu His Leu Ser Thr Ala Ser Gly Glu Leu Gln Ala Asp Ala Ser
            180                 185                 190

Phe Met Gln Thr Leu Trp Asn Met Asn Pro Ile Cys Ser Gly Ala Glu
            195                 200                 205

Glu Gly Tyr Val Thr Gly Gly His Val Leu Arg Leu Phe His Gly His
            210                 215                 220

Met Asp Glu Cys Leu Ser Thr Ser Pro Pro Glu Gln Gly Asp Glu Arg
225                 230                 235                 240

Ser Ser Val Val Ser Tyr Glu Gly Gly Ala Val Cys Thr His Ala Arg
                245                 250                 255

Ser Leu Trp Arg Leu Glu Pro Leu Arg Ile Ser Trp Ser Gly Ser His
            260                 265                 270

Leu Arg Trp Gly Gln Pro Phe Arg Val Arg His Val Thr Ser Gly Arg
            275                 280                 285

Tyr Leu Ala Leu Ser Glu Glu Arg Gly Leu Val Val Val Glu Ala Ala
            290                 295                 300

Ala Ala Gly Thr Arg Ala Ala Ala Phe Cys Phe Arg Ala Ser Lys Glu
305                 310                 315                 320

Lys Leu Glu Ala Gly Thr Lys Arg Asp Val Glu Gly Met Gly Pro Pro
                325                 330                 335

Glu Ile Lys Tyr Gly Glu Ser Leu Cys Phe Val Gln His Ala Ala Ser
            340                 345                 350

Gly Leu Trp Leu Thr Tyr Ala Ala Ala Asp Thr Lys Ala Leu Arg Leu
            355                 360                 365

Gly Leu Met Lys Arg Arg Pro Ile Leu His Gln Glu Gly His Met Asp
            370                 375                 380

Asp Ala Leu Ser Leu Ser Arg Ser Gln Gly Glu Glu Ser Gln Ala Ala
385                 390                 395                 400

Arg Met Ile Tyr Ser Thr Ala Gly Leu Tyr Gly Ser Phe Ile Arg Ser
                405                 410                 415

Leu Asp Ala Leu Ser Ser Arg Gly Arg Gly Gly Ala Gly Asn Ala
            420                 425                 430

Ala Leu Pro Ile Ala Ala Val Ile Leu Ser Leu Arg Asp Leu Ile Ala
            435                 440                 445

Tyr Phe Arg Ala Pro His Thr Glu Leu Gln His Glu Gln Arg Gln Asn
            450                 455                 460

Arg Leu Arg Ser Leu Arg Arg Gln Asp Leu Phe Gln Gln Glu Gly
465                 470                 475                 480

Met Ile Ser Leu Val Leu Asn Cys Ile Asp Arg Leu Asn Val Tyr Ser
                485                 490                 495

Thr Ala Ala His Phe Ala Glu Phe Ala Gly Glu Glu Ala Ala Ala Ala
            500                 505                 510

Trp Lys Glu Ile Val Asn Leu Leu Tyr Glu Leu Leu Ala Ser Leu Ile
```

```
            515                 520                 525
Arg Gly Asn Arg Thr Asn Cys Ala Leu Phe Ser Thr Asn Leu Asp Trp
            530                 535                 540
Leu Val Ser Lys Leu Asp Arg Leu Glu Ala Ser Ser Gly Ile Leu Glu
545                 550                 555                 560
Val Leu Tyr Cys Val Leu Ile Glu Ser Pro Glu Val Leu Asn Ile Ile
                    565                 570                 575
Gln Glu Asn His Ile Lys Ser Ile Ile Ser Leu Leu Asp Lys His Gly
                580                 585                 590
Arg Asn His Lys Val Leu Asn Val Leu Cys Ser Leu Cys Val Cys Asn
            595                 600                 605
Ala Val Ala Val Arg Ser Asn Gln Asn Leu Ile Thr Glu Asn Leu Leu
            610                 615                 620
Pro Arg Arg Asp Leu Leu Leu Gln Thr Gly Pro Val Ser Tyr Val Ser
625                 630                 635                 640
Ser Ile Arg Pro Asn Ile Leu Leu Gly Thr His Glu Gly Ser Thr Gln
                    645                 650                 655
Tyr Pro Arg Trp Tyr Phe Glu Val Ala Val Asp His Val Glu Pro Phe
                660                 665                 670
Val Thr Ala Gln Pro Thr His Leu Arg Val Gly Trp Ala Met Ala Glu
            675                 680                 685
Gly Tyr Ser Pro Tyr Pro Gly Gly Gly Glu Gly Trp Gly Ala Tyr Gly
            690                 695                 700
Ala Gly Asp Asp Leu Tyr Ser Phe Ala Phe Asp Gly Leu His Leu Trp
705                 710                 715                 720
Ala Gly Gly Val Pro Arg Ala Ala Pro Ser Pro Gln Gln His Ile Leu
                    725                 730                 735
Ala Pro Gly Asp Val Val Ser Cys Cys Leu Asp Leu Ser Val Pro Thr
                740                 745                 750
Ile Ser Ser Arg Leu Asn Gly Ser Pro Val Leu Gly Met Phe Glu Lys
            755                 760                 765
Phe Asn Arg Asp Ala Leu Phe Ser Pro Val Val Ser Phe Ser Ala Gly
            770                 775                 780
Val Arg Leu Arg Phe Leu Leu Gly Gly Arg His Gly Asp Phe Gln Phe
785                 790                 795                 800
Leu Pro Pro Pro Gly Tyr Ser Pro Cys Ala Glu Ala Leu Leu Pro Arg
                    805                 810                 815
Glu Arg Leu Arg Leu Glu Pro Ile Lys Ala Tyr Arg Gly Asp Gly Pro
                820                 825                 830
Pro Pro His Cys Leu Leu Gly Pro Thr Lys Ala Leu Pro His Thr Ala
                835                 840                 845
Phe Thr Pro Cys Pro Val Asp Thr Ala Gln Ile Val Leu Pro Pro His
            850                 855                 860
Leu Glu Arg Ile Arg Glu Lys Leu Ala Glu Asn Ile His Glu Leu Trp
865                 870                 875                 880
Ala Leu Thr Arg Ile Glu Gln Gly Trp Thr Tyr Gly Pro Ile His Asp
                    885                 890                 895
Asp Ala Glu Gln Leu His Pro Cys Leu Leu Asp Phe His Ser Leu Pro
                900                 905                 910
Glu Pro Glu Arg Asn Tyr Asn Leu Gln Met Ser Gly Glu Thr Leu Lys
            915                 920                 925
Thr Leu Leu Ala Leu Gly Cys His Val Gly Met Ala Asp Glu Lys Ala
            930                 935                 940
```

```
Glu Glu Asn Leu Arg Lys Ile Lys Leu Pro Lys Thr Tyr Thr Met Arg
945                 950                 955                 960

Asn Gly Tyr Lys Pro Ala Pro Leu Asp Leu Ala His Val Arg Leu Thr
                965                 970                 975

Pro Ala Gln Leu Thr Leu Val Asp Arg Leu Ala Glu Asn Ala His Asn
            980                 985                 990

Val Trp Ala Arg Asp Arg Val Gln Gln Gly Arg Thr Tyr Ser Ile Val
        995                 1000                1005

Gln Asp Ile Lys Asn Lys Arg Asn Pro Arg Leu Val Pro Tyr Asn
    1010                1015                1020

Leu Leu Asp Glu Arg Thr Lys Lys Thr Asn Arg Asp Ser Leu Cys
    1025                1030                1035

Glu Ala Val Arg Thr Leu Ile Gly Tyr Gly Tyr Asn Ile Glu Pro
    1040                1045                1050

Pro Asp Gln
    1055

<210> SEQ ID NO 23
<211> LENGTH: 3375
<212> TYPE: PRT
<213> ORGANISM: Meleagris gallopavo

<400> SEQUENCE: 23

Leu Pro Ala Val Pro Arg Leu Glu Glu Asp Val Val Pro Asp Glu Arg
1               5                   10                  15

Asp Asp Pro Asp Val Ile Met Asn Ser Thr Thr Tyr Tyr Phe Ser Val
                20                  25                  30

Arg Ile Phe Ala Gly Gln Asp Pro Ser His Val Trp Val Gly Arg Val
            35                  40                  45

Thr Pro Asp Tyr His Gln His Asp Pro Asn Phe Asp Leu Thr Arg Val
    50                  55                  60

Arg Thr Val Thr Val Thr Met Gly Asp Asp Arg Gly Asn Val His Asp
65                  70                  75                  80

Ser Ile Arg Arg Ser Ser Cys Tyr Met Leu Trp Ala Gly Glu Phe Gly
                85                  90                  95

Ser Ala Ser Pro Gln Ser Arg Ser His Ser Asp Ala Val Ile Gly Cys
            100                 105                 110

Leu Val Asp Val Ala Thr Gly Leu Met Thr Phe Thr Ala Asn Gly Lys
        115                 120                 125

Glu Leu Asn Thr Phe Phe Gln Val Glu Pro Asn Thr Lys Leu Phe Pro
    130                 135                 140

Ala Val Phe Val Leu Pro Ser Ser Gln His Val Val Gln Phe Glu Leu
145                 150                 155                 160

Gly Lys Leu Lys Asn Ile Leu Pro Leu Ser Ala Ala Leu Phe Ser Ser
                165                 170                 175

Glu Arg Cys Asn Pro Glu Pro Gln Cys Pro Pro Arg Leu Cys Ile Gln
            180                 185                 190

Arg Leu Thr Ala Val Thr Trp Ser Arg Met Ala Ala Glu Glu Leu Pro
        195                 200                 205

Val Ser Ser Gly Arg Ala Ala Asp Gly Arg Gly Trp Glu Val Arg Cys
    210                 215                 220

Ser Glu Pro Arg Leu Met Met Ala Leu His Ile Pro Glu Glu Asn Arg
225                 230                 235                 240

Cys Met Asp Ile Met Glu Leu Trp Glu Arg Gln Asp Leu Leu Arg Phe
```

-continued

```
                245                 250                 255
His Trp His Thr Leu Lys Leu Tyr Cys Ala Val Cys Ala Leu Gly Asn
            260                 265                 270

Thr Arg Val Ala His Ala Leu Cys Ser His Val Asp Pro Ser Gln Leu
            275                 280                 285

Leu Phe Ala Ile Arg Ser Pro Glu Leu Pro Gly Pro Leu Arg Ala Gly
            290                 295                 300

Tyr Tyr Asp Leu Leu Leu Ala Val His Leu Glu Gln Gly Val Arg Ala
305                 310                 315                 320

Arg Ala Ser Met Ser Thr Glu Phe Ile Val Pro Met Asp Glu Ala Ser
            325                 330                 335

Lys Arg Ile Ser Leu Phe Pro Ala Gly Gly Gly Asp Val Lys Val
            340                 345                 350

Pro Gly Pro Pro Gly Val Gly Leu Ser Ala Cys Leu Arg Pro Arg Pro
            355                 360                 365

His Phe Ala Glu Pro Cys Phe Val Arg Pro Pro Asp Gly Arg Ala Leu
            370                 375                 380

Leu Gly Pro Ser Ile Pro Leu Arg Ala Leu Gly Arg Arg Ala Ile Arg
385                 390                 395                 400

Met Leu Arg Glu Ala Val Ala Gly Gly Gly Pro His Ala Arg Asp Pro
            405                 410                 415

Val Gly Gly Gly Val Glu Phe Gln Leu Val Pro Val Leu Lys Leu Val
            420                 425                 430

Ser Ala Leu Leu Ala Val Gly Ala Leu Arg Asp Pro Glu Val Arg Lys
            435                 440                 445

Val Leu Arg Met Ile Glu Pro Arg Val Phe Gly Gly Gly Glu Glu Glu
            450                 455                 460

Glu Glu Glu Glu Glu Arg Arg Arg Arg Lys Ala Val Glu Ala Gly
465                 470                 475                 480

Glu Glu Glu Glu Glu Val Asp Glu Glu Glu Val Asp Glu Glu Glu
            485                 490                 495

Asp Glu Glu Glu Glu Asp Gly Pro Glu Glu Gly Leu Leu Gln Met
            500                 505                 510

Lys Leu Pro Glu Ser Val Lys Leu Gln Met Cys Asn Leu Leu Gln Phe
            515                 520                 525

Phe Cys Asp Gln Glu Leu Gln His Arg Val Glu Ala Ile Val Ala Phe
            530                 535                 540

Ser Glu Arg His Val Glu Arg Leu Gln Arg Asp Gln Arg Arg Tyr
545                 550                 555                 560

Gly Arg Leu Met Gly Ala Val Thr Met Ser Ala Ala Glu Thr Ala Arg
            565                 570                 575

Arg Thr Arg Glu Phe Arg Ser Pro Pro Gln Glu Gln Ile Asn Met Leu
            580                 585                 590

Leu Gln Tyr Lys Gly Gly Ala Asp Glu Glu Asp Cys Pro Val Pro Pro
            595                 600                 605

Asp Ile Arg Gly Glu Leu Leu Gln Phe His Ser Asp Leu Leu Ala His
            610                 615                 620

Cys Gly Ile Glu Leu Gln Gly Glu Glu Glu Glu Glu Glu Asp Ala
625                 630                 635                 640

Ser Leu Arg Gln Arg Leu Leu Ala Leu Val Gln Arg Val Val Gly Arg
            645                 650                 655

Gln Gln Lys Glu Glu Glu Glu Glu Ala Thr Ser Pro Glu Pro Pro
            660                 665                 670
```

-continued

Val Pro Arg Thr Leu Gln Glu Leu Ile Ser His Thr Met Val His Trp
        675                 680                 685

Ala Gln Glu Ser Phe Ile Gln Ser Pro Glu Leu Val Arg Ser Met Phe
    690                 695                 700

Ser Leu Leu His Arg Gln Tyr Asp Gly Leu Gly Glu Leu Val Arg Ala
705                 710                 715                 720

Leu Pro Lys Ala Tyr Thr Ile Ser Ala His Ser Val Pro Asp Thr Thr
                725                 730                 735

Ala Leu Leu Glu Cys Leu Gly Gln Ile Arg Ser Leu Leu Ile Val Gln
            740                 745                 750

Met Gly Pro Glu Glu Asn Leu Met Ile Gln Ser Ile Gly Asn Ile
        755                 760                 765

Met Asn Asn Lys Val Phe Tyr Gln His Pro Asn Leu Met Arg Ala Leu
    770                 775                 780

Gly Met His Glu Thr Val Met Gln Val Met Val Ser Val Leu Gly Gly
785                 790                 795                 800

Gly Glu Thr Lys Glu Ile Arg Phe Pro Lys Met Val Thr Asn Cys Cys
                805                 810                 815

Arg Phe Leu Cys Tyr Phe Cys Arg Ile Ser Arg Gln Asn Gln Arg Ser
            820                 825                 830

Met Phe Asp His Leu Gly Tyr Leu Leu Glu Asn Ser Ser Ile Gly Leu
        835                 840                 845

Gly Met Gln Gly Ser Thr Pro Leu Asp Val Ala Ala Ala Ser Val Ile
    850                 855                 860

Asp Asn Asn Glu Leu Ala Leu Ala Leu Lys Glu Gln Asp Leu Glu Lys
865                 870                 875                 880

Val Val Thr Tyr Leu Ala Ser Cys Gly Leu Gln Ser Cys Pro Met Leu
                885                 890                 895

Leu Ser Lys Gly Tyr Pro Asp Ile Gly Trp Asn Pro Cys Gly Gly Glu
            900                 905                 910

Arg Tyr Leu Asp Phe Leu Arg Phe Ala Val Phe Val Asn Gly Glu Ser
        915                 920                 925

Val Glu Glu Asn Ala Asn Val Val Val Arg Leu Leu Ile Arg Arg Pro
    930                 935                 940

Glu Cys Phe Gly Pro Ala Leu Arg Gly Glu Gly Gly Ser Gly Leu Leu
945                 950                 955                 960

Ala Ala Ile Glu Asp Ala Ile Lys Ile Ser Glu Asp Pro Ala Arg Asp
                965                 970                 975

Gly Pro Thr Val Lys Lys Glu Arg Arg Arg Glu Ile Phe Gly Ala Glu
            980                 985                 990

Glu Pro His Glu Glu Asn Arg Val His Leu Gly Asn Ala Ile Met Ser
        995                 1000                1005

Phe Tyr Ala Ala Ser Ile Asp Leu Leu Gly Arg Cys Ala Pro Glu
    1010                1015                1020

Met His Leu Ile Gln Ala Gly Lys Gly Glu Ala Leu Arg Ile Arg
    1025                1030                1035

Ala Ile Leu Arg Ser Leu Val Pro Leu Asp Asp Leu Val Gly Val
    1040                1045                1050

Ile Ser Leu Pro Leu Gln Ile Pro Ala Phe Gly Lys Asp Gly Asn
    1055                1060                1065

Val Val Gln Pro Arg Met Ala Ala Ser Phe Val Pro Asp His Lys
    1070                1075                1080

```
Ala Pro Met Val Leu Phe Leu Asp Arg Val Tyr Gly Ile Glu Thr
1085                1090                1095

Gln Gln Phe Leu Leu His Val Leu Glu Val Gly Phe Leu Pro Asp
1100                1105                1110

Met Arg Pro Ala Ala Ser Leu Asp Thr Ala Ala Phe Ser Thr Thr
1115                1120                1125

Lys Met Ala Leu Ala Leu Asn Arg Tyr Leu Cys Val Pro Val Leu
1130                1135                1140

Pro Leu Ile Thr Lys Cys Ala Pro Leu Phe Ala Gly Thr Glu His
1145                1150                1155

Arg Ala Ile Met Val Asp Ser Met Leu His Thr Ile Tyr Arg Leu
1160                1165                1170

Ser Arg Gly Arg Ala Leu Thr Lys Ala Gln Arg Asp Ala Ile Glu
1175                1180                1185

Glu Cys Leu Met Ala Leu Cys Arg Tyr Ile Arg Pro Ser Met Leu
1190                1195                1200

Gln His Leu Leu Arg Arg Leu Val Phe Asp Val Pro Ile Leu Asn
1205                1210                1215

Glu Phe Ala Lys Met Pro Leu Lys Leu Leu Thr Asn His Tyr Glu
1220                1225                1230

Arg Cys Trp Lys Tyr Tyr Cys Leu Pro Ser Gly Trp Pro Asn Tyr
1235                1240                1245

Gly Val Ser Ser Glu Glu Glu Leu His Leu Thr Arg Lys Leu Phe
1250                1255                1260

Trp Gly Ile Phe Glu Ser Leu Ala His Lys Lys Phe Asp Pro Glu
1265                1270                1275

Leu Tyr Lys Leu Ala Met Pro Cys Leu Cys Ala Ile Ala Gly Ala
1280                1285                1290

Leu Pro Pro Asp Tyr Val Asp Ala Ser Tyr Ser Ser Lys Thr Glu
1295                1300                1305

Lys Lys Ala Ser Val Asp Ala Glu Gly Asn Phe Asp Pro Lys Pro
1310                1315                1320

Val Glu Thr Leu Asn Val Ile Ile Pro Glu Lys Leu Asp Gly Phe
1325                1330                1335

Ile Asn Lys Tyr Ala Glu Phe Thr His Glu Lys Trp Ala Phe Asp
1340                1345                1350

Lys Ile Gln Asn Asn Trp Thr Tyr Gly Glu Thr Val Asp Glu Glu
1355                1360                1365

Ala Lys Thr His Pro Met Leu Arg Pro Tyr Lys Thr Phe Ser Glu
1370                1375                1380

Lys Asp Lys Glu Ile Tyr Arg Trp Pro Ile Lys Glu Ser Leu Lys
1385                1390                1395

Ala Met Leu Ala Trp Glu Trp Met Val Glu Lys Ala Arg Glu Gly
1400                1405                1410

Asp Glu Glu Lys Ala Glu Lys Lys Lys Thr Arg Lys Ile Ser Gln
1415                1420                1425

Ser Ala Gln Ala Thr Tyr Asp Pro Ser His Gly Tyr Asn Pro Gln
1430                1435                1440

Pro Val Asp Leu Ser Gly Val Thr Leu Ser Arg Glu Leu Gln Ala
1445                1450                1455

Met Ala Glu Gln Leu Ala Glu Asn Tyr His Asn Thr Trp Gly Arg
1460                1465                1470

Lys Lys Lys Gln Glu Leu Glu Ala Lys Gly Gly Gly Ser His Pro
```

-continued

```
                1475                1480                1485

Leu Leu Val Pro Tyr Asp Thr Leu Thr Ala Lys Glu Lys Ala Arg
    1490                1495                1500

Asp Arg Glu Lys Ala Gln Glu Leu Leu Lys Phe Leu Gln Leu Asn
    1505                1510                1515

Gly Tyr Ala Val Thr Arg Gly Leu Lys Asp Met Glu Leu Asp Thr
    1520                1525                1530

Ser Ser Ile Glu Lys Arg Phe Ala Tyr Gly Phe Leu Gln Gln Leu
    1535                1540                1545

Leu Arg Trp Met Asp Ile Ser Gln Glu Phe Ile Ala His Leu Glu
    1550                1555                1560

Ala Val Val Ser Ser Gly Arg Val Glu Lys Ser Pro His Glu Gln
    1565                1570                1575

Glu Ile Lys Phe Phe Ala Lys Ile Leu Leu Pro Leu Ile Asn Gln
    1580                1585                1590

Tyr Phe His Asn His Cys Leu Tyr Phe Leu Ser Thr Pro Ala Lys
    1595                1600                1605

Val Leu Gly Ser Gly Gly His Ala Ser Asn Lys Glu Lys Glu Met
    1610                1615                1620

Ile Thr Ser Leu Phe Cys Lys Leu Ala Ala Leu Val Arg His Arg
    1625                1630                1635

Val Thr Leu Phe Gly Thr Asp Ala Pro Ala Val Val Asn Cys Leu
    1640                1645                1650

His Ile Leu Ala Arg Ser Leu Asp Ala Arg Thr Val Met Lys Ser
    1655                1660                1665

Gly Pro Glu Ile Val Lys Ala Gly Leu Arg Ser Phe Phe Glu Ser
    1670                1675                1680

Ala Ser Glu Asp Ile Glu Lys Met Val Glu Asn Leu Lys Leu Gly
    1685                1690                1695

Lys Val Thr Gln Ser Arg Thr Gln Val Lys Gly Val Ala Gln Asn
    1700                1705                1710

Ile Asn Tyr Thr Thr Val Ala Leu Leu Pro Val Leu Thr Ser Leu
    1715                1720                1725

Phe Glu His Ile Ala Gln His Gln Phe Gly Asp Asp Val Ile Leu
    1730                1735                1740

Asp Asp Val Gln Val Ser Cys Tyr Arg Ile Leu Cys Ser Ile Tyr
    1745                1750                1755

Ser Leu Gly Thr Thr Arg Asn Pro Tyr Val Glu Arg Gln Arg Pro
    1760                1765                1770

Ala Leu Gly Glu Cys Leu Ala Arg Leu Ala Ala Ala Met Pro Val
    1775                1780                1785

Ala Phe Leu Glu Pro Arg Leu Asn Glu Phe Asn Pro Cys Ser Val
    1790                1795                1800

Tyr Ser Thr Lys Ser Pro Arg Glu Arg Ala Asn Pro His Leu Trp
    1805                1810                1815

Gly Thr Ala Asp Pro His Pro Ile Phe Gly Thr Pro Thr Pro Val
    1820                1825                1830

Leu Gly Leu Pro Ser His Val Glu Glu Met Cys Pro Asp Ile Pro
    1835                1840                1845

Asp Leu Glu Arg Leu Met Lys Asp Ile Gly Gly Leu Ala Glu Ser
    1850                1855                1860

Gly Ala Arg Tyr Thr Glu Met Pro His Val Ile Glu Val Thr Leu
    1865                1870                1875
```

```
Pro Met Leu Cys Asn Tyr Leu Pro Arg Trp Trp Glu Arg Gly Pro
    1880                1885                1890

Asp Ser Ser Pro Gln Gly Pro Trp Ala Thr Ala Val Thr Gly Gln
    1895                1900                1905

His Leu Asn Ala Leu Ala Gly Lys His Pro Ala His Arg Gly Gln
    1910                1915                1920

Gln Pro Gly His Arg Arg Gly Val Leu Asp Glu Thr Leu Ala Val
    1925                1930                1935

Phe Ala Gln Pro Ile Val Ser Lys Ala Lys Pro Glu Leu Leu Arg
    1940                1945                1950

Thr His Phe Ile Pro Thr Met Glu Lys Leu Lys Arg Ala Gly
    1955                1960                1965

Lys Val Val Ser Glu Glu Gln Leu Arg Met Glu Ala Lys Ala
    1970                1975                1980

Glu Ala Glu Asp Ala Glu Leu Leu Ile Arg Asp Glu Phe Ser Val
    1985                1990                1995

Leu Cys Arg Asp Leu Tyr Ala Leu Tyr Pro Leu Leu Ile Arg Tyr
    2000                2005                2010

Val Asp Asn Ser Arg Ala Lys Trp Leu Thr Glu Pro Asn Ala Asp
    2015                2020                2025

Ala Glu Glu Leu Phe Arg Met Val Gly Glu Val Phe Ile Tyr Trp
    2030                2035                2040

Ser Lys Ser His Asn Phe Lys Arg Glu Glu Gln Asn Phe Val Val
    2045                2050                2055

Gln Asn Glu Ile Asn Asn Met Ser Phe Leu Thr Ala Asp Ser Lys
    2060                2065                2070

Ser Lys Met Ala Lys Ser Gly Asp Gly Gln Gly Gly Ser Glu
    2075                2080                2085

Gln Glu Arg Thr Lys Lys Lys Arg Arg Gly Asp Arg Tyr Ser Ile
    2090                2095                2100

His Thr Ser Leu Ile Val Ala Thr Leu Lys Lys Met Leu Pro Ile
    2105                2110                2115

Gly Leu Asn Met Cys Ser Pro Thr Asp Gln Glu Leu Ile Ser Leu
    2120                2125                2130

Ala Lys Ser Arg Tyr Ala Leu Lys Asp Thr Asp Glu Glu Val Gln
    2135                2140                2145

Glu Cys Leu Asn Asn Asn Leu His Leu Gln Gly Lys Cys Glu Asn
    2150                2155                2160

Ser Ser Ala Met Arg Trp Gln Leu Ala Leu Tyr Arg Ala Met Ala
    2165                2170                2175

Gly Arg Ala Glu Asp Ser Asp Ser Pro Glu Lys Ile Val Arg Arg
    2180                2185                2190

Val Gln Glu Val Ser Ala Val Leu Tyr His Leu Glu Gln Thr Glu
    2195                2200                2205

His Pro Tyr Lys Ser Lys Lys Ala Val Trp His Lys Leu Leu Ser
    2210                2215                2220

Lys Gln Arg Arg Arg Ala Val Val Ala Cys Phe Arg Met Thr Pro
    2225                2230                2235

Leu Tyr Asn Leu Pro Arg His Arg Ala Cys Asn Met Phe Leu Glu
    2240                2245                2250

Ala Tyr Lys Leu Leu Trp Leu Val Thr Glu Glu His Pro Phe Glu
    2255                2260                2265
```

-continued

```
Asp Arg Met Ile Asp Asp Leu Ala Lys Ser Gly Glu Glu Glu Glu
    2270                2275                2280
Glu Glu Glu Glu Glu Lys Asp Lys Lys Pro Asp Pro Leu His Gln
    2285                2290                2295
Leu Ile Leu His Phe Ser Arg Thr Ala Leu Thr Glu Lys Ser Lys
    2300                2305                2310
Leu Glu Lys Asp His Leu Tyr Met Ala Tyr Ala Gly Ile Met Ala
    2315                2320                2325
Lys Ser Cys His Ile Glu Glu Gly Asn Glu Glu Glu Lys Glu Glu
    2330                2335                2340
Lys Lys Glu Glu Glu Asp Pro Glu Asp Ser Phe Glu Glu Lys Glu
    2345                2350                2355
Met Glu Lys Gln Lys Leu Leu Tyr Gln Gln Ser Arg Leu His Thr
    2360                2365                2370
Arg Gly Ala Ala Glu Met Val Leu Gln Met Ile Ser Ala Cys Lys
    2375                2380                2385
Gly Glu Arg Gly Glu Met Val Ser Ser Thr Leu Lys Leu Gly Ile
    2390                2395                2400
Ser Ile Leu Asn Gly Gly Asn Ala Asp Val Gln Gln Lys Met Leu
    2405                2410                2415
Asp Tyr Leu Lys Glu Lys Arg Glu Ile Gly Phe Phe Gln Ser Val
    2420                2425                2430
Gln Ala Leu Met Gln Thr Cys Ser Val Leu Asp Leu Asn Ala Phe
    2435                2440                2445
Glu Arg Gln Asn Lys Ala Glu Gly Leu Gly Met Val Thr Glu Glu
    2450                2455                2460
Gly Thr Ile Ile Ser Arg Glu Asn Gly Glu Lys Val Met Ser Asp
    2465                2470                2475
Asp Glu Phe Thr Gln Asp Leu Phe Arg Leu Leu Gln Leu Leu Cys
    2480                2485                2490
Glu Gly His Asn Asn Asp Phe Gln Asn Tyr Leu Arg Thr Gln Thr
    2495                2500                2505
Gly Asn Thr Thr Thr Ile Asn Ile Ile Ile Cys Thr Val Asp Tyr
    2510                2515                2520
Leu Leu Arg Leu Gln Glu Ser Ile Ser Asp Phe Tyr Trp Tyr Tyr
    2525                2530                2535
Ser Gly Lys Asp Val Ile Asp Glu Gln Gly Lys Arg Asn Phe Ser
    2540                2545                2550
Lys Ala Met Ala Val Ala Lys Gln Val Phe Asn Ser Leu Thr Glu
    2555                2560                2565
Tyr Ile Gln Gly Pro Cys Thr Gly Asn Gln Gln Ser Leu Ala His
    2570                2575                2580
Ser Arg Leu Trp Asp Ala Val Val Gly Phe Leu His Val Phe Ala
    2585                2590                2595
His Met Met Lys Lys Leu Ala Gln Asp Ser Ser Gln Ile Gly Leu
    2600                2605                2610
Leu Lys Glu Leu Leu Asp Leu Gln Lys Asp Met Val Val Met Leu
    2615                2620                2625
Leu Ser Leu Leu Glu Gly Asn Val Val Asn Gly Thr Ile Ala Arg
    2630                2635                2640
Gln Val Val Asp Met Pro Val Glu Ser Ser Ser Asn Val Thr Met
    2645                2650                2655
Ile Leu Lys Phe Phe Asp Met Phe Leu Lys Leu Arg Asp Ile Val
```

-continued

```
                2660                2665                2670
Ala Ser Asp Ala Phe Arg Asp Tyr Val Thr Asp Pro Arg Gly Leu
    2675                2680                2685
Ile Ser Lys Lys Asp Phe Gln Lys Ala Met Asp Ser Gln Lys Gln
    2690                2695                2700
Tyr Glu Pro Ser Glu Val Gln Phe Leu Leu Ser Cys Ser Glu Ala
    2705                2710                2715
Asp Glu Asn Glu Met Ile Asp Val Glu Ala Phe Val Gly Arg Ser
    2720                2725                2730
Gln Glu Pro Ala Arg Asp Ile Gly Phe Asn Val Ala Val Leu Leu
    2735                2740                2745
Thr Asn Leu Ala Glu His Val Pro His Asp Gln Arg Leu Arg Thr
    2750                2755                2760
Phe Leu Glu Gln Ala Ala Ser Ile Leu Glu Tyr Phe Arg Pro Phe
    2765                2770                2775
Leu Gly Arg Ile Glu Ile Met Gly Ala Ala Arg Arg Ile Glu Arg
    2780                2785                2790
Leu Tyr Phe Glu Ile Ser Ala Ala Asn Lys Ala Gln Trp Glu Met
    2795                2800                2805
Pro Gln Glu Asp Gly Lys Glu Val Val Glu Pro Gln Lys Glu
    2810                2815                2820
Glu Glu Glu Ala Ala Ala Glu Thr Glu Lys Ala Asp Thr Glu Asn
    2825                2830                2835
Gly Glu Lys Gly Asp Gly Gly Ala Glu Gly Gly Pro Glu Val Glu
    2840                2845                2850
Thr Pro Glu Lys Gln Gln Lys Ala Ser Pro Pro Arg Glu Arg Lys
    2855                2860                2865
Glu Pro Pro Pro Pro Glu Gly Ala Phe Glu Phe Trp Thr Glu Leu
    2870                2875                2880
Glu Val Gln Arg Val Lys Phe Leu Asn Tyr Leu Ser Arg Asn Phe
    2885                2890                2895
Tyr Asn Leu Arg Phe Leu Ala Leu Phe Leu Ala Phe Ala Ile Asn
    2900                2905                2910
Phe Ile Leu Leu Phe Tyr Lys Val Ser Glu Arg Pro Pro Gly Met
    2915                2920                2925
Glu Glu Ala Glu Leu Glu Gly Ser Gly Met Ala Ala Val Leu Asp
    2930                2935                2940
Gly Ile Gly Asp Phe Gly Asp Gly Gly Asp Gly Gly Gly Asp
    2945                2950                2955
Gly Glu Glu Glu Pro Ser Val Val Tyr Tyr Cys Leu Glu Glu Ser
    2960                2965                2970
Thr Gly Tyr Met Gln Pro Ala Leu Arg Ala Leu Ala Val Ala His
    2975                2980                2985
Thr Ile Val Ala Phe Leu Cys Ile Ile Gly Tyr Asn Cys Leu Lys
    2990                2995                3000
Ile Pro Leu Val Ile Phe Lys Arg Glu Lys Glu Val Ala Arg Arg
    3005                3010                3015
Leu Glu Phe Ser Gly Leu Tyr Ile Thr Glu Gln Pro Pro Asp Asp
    3020                3025                3030
Asp Val Lys Gly Gln Trp Asp Arg Leu Val Leu Asn Ala Gln Ser
    3035                3040                3045
Phe Pro Ser Asn Tyr Trp Asp Lys Phe Val Lys Arg Lys Val Leu
    3050                3055                3060
```

```
Glu Lys Tyr Gly Asp Ile Tyr Gly Arg Glu Arg Ile Ala Glu Leu
    3065                3070                3075

Leu Gly Met Glu Leu Ser Ser Leu Glu Ile Gly Ala Arg Gly Glu
    3080                3085                3090

Arg Lys Pro Pro Pro Asp Asn Ser Val Leu Thr Trp Ile Thr Phe
    3095                3100                3105

Ile Asp Ile Arg Tyr Gln Ile Trp Lys Phe Gly Val Ile Phe Thr
    3110                3115                3120

Asp Asn Ser Phe Leu Tyr Leu Thr Trp Tyr Met Gly Met Ser Leu
    3125                3130                3135

Leu Gly His Tyr Asn Asn Phe Phe Phe Val Ala His Leu Leu Asp
    3140                3145                3150

Ile Ala Met Gly Val Lys Thr Leu Arg Thr Ile Leu Ser Ser Val
    3155                3160                3165

Thr His Asn Gly Ser Asn Leu Ala Met Thr Val Gly Leu Leu Ala
    3170                3175                3180

Val Val Val Tyr Leu Tyr Thr Val Val Ala Phe Asn Phe Phe Arg
    3185                3190                3195

Lys Phe Tyr Asn Lys Ser Glu Asp Glu Asp Glu Pro Asp Met Lys
    3200                3205                3210

Cys Asp Asp Met Met Thr Cys Tyr Leu Phe His Met Tyr Val Gly
    3215                3220                3225

Val Arg Ala Gly Gly Gly Ile Gly Asp Glu Ile Glu Asp Pro Ala
    3230                3235                3240

Gly Asp Glu Tyr Glu Leu Tyr Arg Val Val Phe Asp Ile Thr Phe
    3245                3250                3255

Phe Phe Phe Val Ile Val Ile Leu Leu Ala Ile Ile Gln Gly Leu
    3260                3265                3270

Ile Ile Asp Ala Phe Gly Glu Leu Arg Asp Gln Gln Glu Gln Val
    3275                3280                3285

Lys Glu Asp Met Glu Thr Lys Cys Phe Ile Cys Gly Ile Gly Ser
    3290                3295                3300

Asp Tyr Phe Asp Thr Thr Pro His Gly Phe Glu Thr His Thr Leu
    3305                3310                3315

Glu Glu His Asn Leu Ala Asn Tyr Met Phe Phe Leu Met Tyr Leu
    3320                3325                3330

Ile Asn Lys Asp Glu Thr Glu His Thr Gly Gln Glu Ser Tyr Val
    3335                3340                3345

Trp Lys Met Tyr Gln Glu Arg Cys Trp Asp Phe Phe Pro Ala Gly
    3350                3355                3360

Asp Cys Phe Arg Lys Gln Tyr Glu Asp Gln Leu Gly
    3365                3370                3375

<210> SEQ ID NO 24
<211> LENGTH: 4868
<212> TYPE: PRT
<213> ORGANISM: Meleagris gallopavo

<400> SEQUENCE: 24

Met Ala Glu Gly Gly Glu Gly Gly Glu Asp Glu Ile Gln Phe Leu Arg
1               5                   10                  15

Thr Asp Asp Glu Val Val Leu Gln Cys Val Ser Ser Ile His Lys Glu
                20                  25                  30

Gln Arg Lys Phe Cys Leu Ala Ala Glu Gly Leu Gly Asn Arg Leu Cys
```

-continued

```
                35                  40                  45
Phe Leu Glu Pro Thr Ser Glu Ala Lys Tyr Val Pro Pro Asp Leu Cys
 50                  55                  60

Ile Cys Asn Phe Val Leu Glu Gln Ser Leu Ser Val Arg Ala Leu Gln
 65                  70                  75                  80

Glu Met Leu Thr Asn Thr Gly Asp Asn Ala Ser Glu Gly Ala Ala Gln
                 85                  90                  95

Gly Gly His Arg Thr Leu Leu Tyr Gly His Ala Ile Leu Leu Arg His
                100                 105                 110

Ser Phe Ser Glu Met Tyr Leu Thr Cys Leu Thr Ser Ser Arg Ser Gln
                115                 120                 125

Thr Asp Lys Leu Ala Phe Asp Val Gly Leu Arg Glu Asn Ala Ala Gly
130                 135                 140

Glu Ala Cys Trp Trp Thr Ile His Pro Ala Ser Lys Gln Arg Ser Glu
145                 150                 155                 160

Gly Glu Lys Val Arg Ile Gly Asp Asp Leu Ile Leu Val Ser Val Ser
                165                 170                 175

Ser Glu Arg Tyr Leu His Leu Ser Met Ser Asn Gly Ser Ile Gln Val
                180                 185                 190

Asp Ala Ser Phe Met Gln Thr Leu Trp Asn Val His Pro Thr Cys Ser
                195                 200                 205

Gly Ser Asn Ile Thr Glu Gly Tyr Leu Leu Gly Gly His Val Val Arg
                210                 215                 220

Phe Phe His Gly His Asp Glu Cys Leu Thr Ile Pro Ser Thr Asp Gln
225                 230                 235                 240

Asn Asp Ser Gln Gln Lys Lys Val Leu Tyr Glu Thr Gly Gly Ala Gly
                245                 250                 255

Val Arg Ala Arg Ser Leu Trp Arg Val Glu Pro Leu Arg Ile Ser Trp
                260                 265                 270

Ser Gly Ser Asn Ile Arg Trp Gly Gln Pro Phe Arg Leu Arg His Ile
                275                 280                 285

Thr Thr Gly Met Tyr Leu Ala Leu Asn Asp Asp Glu Gly Leu Val Met
290                 295                 300

Leu Asp Arg Glu Lys Ser Asp Thr Thr Ser Ser Ala Phe Cys Phe Arg
305                 310                 315                 320

Ala Ser Lys Glu Leu Lys Glu Lys Gln Asp Ser Thr Leu Lys Arg Asp
                325                 330                 335

Ile Asp Gly Met Gly Val Pro Glu Ile Lys Tyr Gly Asp Ser Val Cys
                340                 345                 350

Phe Val Gln His Val Ala Ser Ala Leu Trp Leu Thr Tyr Lys Ala Pro
                355                 360                 365

Asp Ala Lys Ser Ala Arg Leu Gly Leu Leu Lys Arg Lys Val Ile Leu
370                 375                 380

His Gln Glu Gly His Met Asp Asp Gly Leu Thr Leu Gln Arg Cys Gln
385                 390                 395                 400

His Glu Glu Ser Gln Ala Ala Arg Ile Ile Arg Asn Thr Thr Ser Leu
                405                 410                 415

Phe Ser Gln Phe Ile Ser Gly Asn Asn Arg Thr Leu Ser Pro Ile Ala
                420                 425                 430

Leu Pro Val Glu Glu Met Ala Gln Thr Leu Gln Asp Leu Ile Lys Tyr
                435                 440                 445

Phe Gln Pro Pro Gly Glu Asp Leu Glu His Glu Asp Lys Gln Asn Lys
450                 455                 460
```

```
Leu Arg Ser Leu Lys Asn Arg Gln Asn Leu Phe Lys Asp Glu Gly Met
465                 470                 475                 480

Leu Ala Leu Val Leu Asn Cys Ile Asp Arg Leu Asn Asp Tyr Asn Ser
            485                 490                 495

Ala Ala His Phe Ala Glu Ile Ala Arg Glu Glu Asn Ser Thr Ala Trp
        500                 505                 510

Lys Glu Ile Leu Asn Leu Leu Tyr Glu Leu Leu Ala Ala Leu Ile Arg
            515                 520                 525

Gly Asn Arg Asn Asn Cys Thr Gln Phe Ser Ser Asn Leu Asp Trp Leu
530                 535                 540

Ile Ser Lys Leu Asp Arg Leu Glu Ser Ser Ser Gly Ile Leu Glu Val
545                 550                 555                 560

Leu His Cys Ile Leu Ile Glu Ser Pro Glu Ala Leu Asn Val Ile Ala
            565                 570                 575

Glu Glu His Ile Lys Ser Ile Ile Ser Leu Leu Asp Lys His Gly Arg
            580                 585                 590

Asn Tyr Lys Val Leu Asp Val Leu Cys Ser Leu Cys Val Cys Asn Gly
        595                 600                 605

Val Ala Val Arg Ala Asn Gln Asn Leu Ile Cys Asp Asn Leu Leu Pro
610                 615                 620

Arg Arg Asp Leu Leu Gln Thr Arg Leu Ile Asn Asp Val Thr Ser
625                 630                 635                 640

Ile Arg Pro Asn Ile Phe Leu Gly Val Ala Glu Gly Ser Ala Gln Tyr
            645                 650                 655

Lys Lys Trp Tyr Phe Glu Leu Ile Ile Asp Gln Val Asp Pro Phe Leu
            660                 665                 670

Thr Ala Glu Pro Thr His Leu Arg Val Gly Trp Ala Ser Thr Ser Gly
        675                 680                 685

Tyr Ala Pro Tyr Pro Gly Gly Gly Glu Gly Trp Gly Gly Asn Gly Val
        690                 695                 700

Gly Asp Asp Leu Tyr Ser Phe Gly Phe Asp Gly Leu His Leu Trp Ser
705                 710                 715                 720

Gly Arg Val Pro Arg Ala Val Ala Ser Val Asn Gln His Leu Leu Ser
            725                 730                 735

Ser Asp Asp Val Ser Cys Cys Leu Asp Leu Gly Val Pro Ser Ile
            740                 745                 750

Ser Phe Arg Ile Asn Gly Gln Pro Val Gln Gly Met Phe Glu Asn Phe
        755                 760                 765

Cys Thr Glu Gly Phe Phe Pro Val Val Ser Leu Ser Ala Gly Val
    770                 775                 780

Lys Ala Arg Phe Leu Leu Gly Gly Arg His Gly Glu Phe Lys Phe Leu
785                 790                 795                 800

Pro Pro Ala Gly Tyr Ala Pro Cys Tyr Glu Ala Leu Leu Pro Lys Glu
            805                 810                 815

Lys Met Lys Leu Glu Pro Val Lys Glu Tyr Lys Arg Asp Ser Asp Gly
        820                 825                 830

Val Arg Asp Leu Leu Gly Thr Thr Gln Phe Leu Ser Gln Ala Ser Phe
835                 840                 845

Ile Pro Cys Pro Ile Asp Thr Ser Gln Ile Ala Leu Pro Phe His Leu
        850                 855                 860

Glu Lys Ile Arg Asp Lys Leu Ala Glu Asn Ile His Glu Leu Trp Gly
865                 870                 875                 880
```

-continued

Met Asn Lys Ile Glu Leu Gly Trp Thr Tyr Gly Lys Ile Arg Asp Asp
            885                 890                 895

Asn Lys Arg His His Pro Cys Leu Val Glu Phe Ser Lys Leu Pro Glu
            900                 905                 910

Thr Glu Lys Asn Tyr Asn Leu Gln Met Ser Thr Glu Thr Leu Lys Thr
            915                 920                 925

Leu Leu Ala Leu Gly Cys His Ile Val His Ala Asn Pro Ala Ala Glu
930                 935                 940

Glu Asp Leu Lys Lys Val Lys Leu Pro Lys Asn Tyr Ile Met Ser Asn
945                 950                 955                 960

Gly Tyr Lys Pro Ala Pro Leu Asp Leu Ser Glu Val Lys Leu Leu Pro
                965                 970                 975

Ser Gln Glu Phe Leu Val Asp Lys Leu Ala Glu Asn Ala His Asn Val
                980                 985                 990

Trp Ala Lys Asp Arg Ile Lys Gln Gly Trp Thr Tyr Gly Ile Gln Gln
            995                 1000                1005

Asp Leu Lys Asn Lys Arg Asn Pro Arg Leu Val Pro Tyr Ala Leu
        1010                1015                1020

Leu Asp Glu Arg Thr Lys Lys Ser Asn Arg Asp Ser Leu Arg Glu
        1025                1030                1035

Ala Val Arg Thr Phe Ala Gly Tyr Gly Tyr Asn Ile Glu Pro Pro
        1040                1045                1050

Asp Gln Glu Ile Ala Asp Gln Thr Leu Glu Lys Val Ser Ile Asp
        1055                1060                1065

Lys Ile Arg Phe Phe Arg Val Glu Gln Ser Tyr Ala Val Lys Ser
        1070                1075                1080

Gly Lys Trp Tyr Phe Glu Phe Glu Ala Val Thr Gly Gly Asp Met
        1085                1090                1095

Arg Val Gly Trp Ala Arg Pro Gly Cys Arg Pro Asp Ile Glu Leu
        1100                1105                1110

Gly Ala Asp Asp Gln Ala Phe Val Phe Glu Gly Ser Lys Gly Gln
        1115                1120                1125

Arg Trp His Gln Gly Ser Gly Phe Phe Gly Arg Ser Trp Gln Pro
        1130                1135                1140

Gly Asp Val Val Gly Cys Met Ile Asn Leu Asp Asp Lys Ser Ile
        1145                1150                1155

Ile Phe Thr Leu Asn Gly Glu Leu Leu Ile Thr Ser Lys Gly Ser
        1160                1165                1170

Glu Leu Ala Phe Ala Asp Phe Gly Ile Glu Ser Gly Phe Val Pro
        1175                1180                1185

Ile Cys Ser Leu Gly Leu Ala Gln Ile Gly Arg Met Asn Leu Gly
        1190                1195                1200

Met Asp Ala Ser Thr Phe Lys Tyr Tyr Thr Met Cys Gly Leu Gln
        1205                1210                1215

Glu Gly Phe Glu Pro Phe Ala Val Asn Met Asn Arg Asp Val Ala
        1220                1225                1230

Met Trp Phe Ser Lys Arg Leu Pro Thr Phe Val Asn Val Pro Lys
        1235                1240                1245

Asn His Pro His Ile Glu Ile Trp Arg Ile Asp Gly Thr Ile Glu
        1250                1255                1260

Ser Pro Pro Arg Leu Lys Val Thr His Lys Thr Leu Gly Thr Gln
        1265                1270                1275

Asn Ser Asn Ser Asp Met Ile Tyr Cys Arg Leu Ser Met Pro Ile

-continued

```
              1280                1285                1290

Glu Phe Arg Ser Ser Phe Asn Phe Gly Val Gly Val Glu Asn Ala
    1295                1300                1305

Ser Ser Asp Ala Leu Gln Lys Arg Lys His Ser Gln Glu Phe Pro
    1310                1315                1320

Ala Ser Ser Thr Thr Tyr Phe Tyr Ser Leu Arg Ile Phe Ala Gly
    1325                1330                1335

Gln Asp Pro Ser Ser Val Trp Val Gly Trp Val Thr Pro Asp Tyr
    1340                1345                1350

His Phe Tyr Ser Glu Asn Phe Asp Ile Asn Lys Asn Cys Thr Val
    1355                1360                1365

Thr Val Thr Leu Gly Asp Glu Arg Gly Arg Val His Glu Ser Val
    1370                1375                1380

Lys Arg Ser Asn Cys Tyr Met Val Trp Gly Gly Asp Ile Thr Ala
    1385                1390                1395

Asn Ser Gln Arg Ser Gly Arg Ser Asn Val Asp Leu Glu Ile Gly
    1400                1405                1410

Cys Phe Val Asp Leu Ala Thr Gly Met Leu Ser Phe Thr Ala Asn
    1415                1420                1425

Gly Lys Glu Leu Gly Thr Cys Tyr Gln Val Glu Pro Asn Thr Lys
    1430                1435                1440

Leu Leu Pro Ala Ala Phe Val Gln Pro Thr Ser Thr Asn Leu Ile
    1445                1450                1455

Gln Phe Glu Leu Gly Lys Leu Lys Asn Thr Met Pro Leu Ser Ala
    1460                1465                1470

Ala Ile Phe Lys Ser Glu Glu Arg Asn Pro Val Pro Gln Cys Pro
    1475                1480                1485

Pro Arg Leu Asp Val Gln Thr Ile Thr Pro Val Leu Trp Ser Arg
    1490                1495                1500

Met Pro Asn Ser Phe Leu Lys Val Glu Thr Glu Arg Val Ser Glu
    1505                1510                1515

Arg His Gly Trp Val Val Gln Cys Leu Glu Pro Leu Gln Met Met
    1520                1525                1530

Ala Leu His Ile Pro Glu Glu Asn Arg Cys Val Asp Ile Leu Glu
    1535                1540                1545

Leu Cys Glu Gln Glu Asp Leu Met Lys Phe His Tyr His Thr Leu
    1550                1555                1560

Lys Leu Tyr Ser Ser Val Cys Ala Leu Gly Asn Thr Arg Val Ala
    1565                1570                1575

Tyr Ala Leu Cys Ser His Val Asp Ile Ser Gln Leu Phe Tyr Thr
    1580                1585                1590

Ile Asp Asn Gln Tyr Leu Pro Gly Leu Leu Arg Ser Gly Phe Tyr
    1595                1600                1605

Asp Leu Leu Ile Ser Ile His Leu Asp His Ala Lys Gln Ala Lys
    1610                1615                1620

Leu Met Met Asn Asn Glu Phe Ile Ile Pro Val Thr Glu Glu Thr
    1625                1630                1635

Arg Thr Ile Lys Leu Tyr Pro Asp Glu Thr Lys Lys His Gly Leu
    1640                1645                1650

Pro Gly Val Gly Leu Ser Thr Cys Leu Lys Pro Ser Phe Asn Phe
    1655                1660                1665

Ser Thr Pro Cys Phe Ile Val Thr Ser Glu Glu His Gln Thr Ser
    1670                1675                1680
```

-continued

```
Ser Pro Glu Ile Pro Leu Asp Thr Leu Lys Ser Lys Ala Ile Ser
    1685                1690                1695

Met Leu Thr Glu Ala Val Gln Cys Ser Gly Ser His Ile Arg Asp
    1700                1705                1710

Pro Val Gly Gly His Ile Ala Phe Gln Phe Val Pro Val Leu Lys
    1715                1720                1725

Leu Ile Ala Thr Leu Leu Ile Met Gly Val Phe Asp Asp Asp
    1730                1735                1740

Val Lys Gln Val Leu Ile Leu Ile Asp Pro Asn Val Phe Gly Asp
    1745                1750                1755

Asn Lys Glu Glu Thr Glu Glu Arg Thr Glu Lys Glu Glu Val Thr
    1760                1765                1770

Gln Val Glu Glu Lys Ala Val Glu Ala Gly Glu Lys Ala Val Lys
    1775                1780                1785

Glu Thr Lys Thr Pro Thr Lys Gly Leu Leu Gln Thr Arg Leu Pro
    1790                1795                1800

Glu Ser Gly Lys Leu Gln Met Cys His Leu Leu Asn Tyr Phe Cys
    1805                1810                1815

Asp Cys Glu Leu Gln His Arg Val Glu Ala Ile Val Ser Phe Ala
    1820                1825                1830

Asp His Tyr Val Ser Lys Leu Gln Tyr Asn Gln Lys Tyr Arg Tyr
    1835                1840                1845

Asn Glu Leu Met Gln Ala Leu Asp Met Ser Ala Ala Leu Thr Ala
    1850                1855                1860

Lys Lys Thr Lys Glu Phe Arg Ser Pro Pro Gln Glu Gln Ile Asn
    1865                1870                1875

Met Leu Leu Asn Phe Gln Leu Gly Glu Asp Cys Pro Cys Pro Glu
    1880                1885                1890

Glu Ile Arg Asp Glu Leu Tyr Asp Phe His Asp Asp Leu Leu Ile
    1895                1900                1905

His Cys Gly Ile Pro Leu Glu Glu Glu Glu Glu Glu Glu Glu Asp
    1910                1915                1920

Ser Ser Leu Thr Gly Lys Leu Arg Ser Leu Ile Tyr Lys Ile Lys
    1925                1930                1935

Gly Pro Pro Lys Pro Glu Lys Ile Glu Pro Arg Glu Glu Glu Asp
    1940                1945                1950

Lys Ser Pro Thr Thr Leu Lys Glu Leu Ile Ser Gln Thr Met Val
    1955                1960                1965

Arg Trp Ser Gln Glu Asp Gln Ile Gln Asp Pro Glu Leu Val Arg
    1970                1975                1980

Ile Met Tyr Thr Leu Leu Arg Arg Gln Tyr Asp Ser Ile Gly Glu
    1985                1990                1995

Leu Leu Gln Ala Leu Arg Lys Ala Tyr Thr Ile Ser Ala Gly Ser
    2000                2005                2010

Val Lys Asp Thr Ile Asn Leu Leu Ala Ala Leu Gly Gln Ile Arg
    2015                2020                2025

Ser Leu Leu Ser Val Arg Met Gly Lys Glu Glu Glu Leu Leu Met
    2030                2035                2040

Ile Asn Gly Leu Gly Asp Ile Met Asn Asn Lys Val Phe Tyr Gln
    2045                2050                2055

His Pro Asn Leu Met Arg Val Leu Gly Met His Glu Thr Val Met
    2060                2065                2070
```

-continued

```
Asp Val Met Val Asn Val Leu Gly Gly Asp Lys Ser Gln Ile Val
2075                2080                2085

Phe Pro Lys Met Val Ala Ser Cys Cys Arg Phe Leu Cys Tyr Phe
2090                2095                2100

Cys Arg Ile Ser Arg Gln Asn Gln Lys Ala Met Phe Glu His Leu
2105                2110                2115

Ser Tyr Leu Leu Glu Asn Ser Ser Val Gly Leu Ala Phe Pro Ser
2120                2125                2130

Met Arg Gly Ser Thr Pro Leu Asp Val Ala Ala Ala Ser Val Met
2135                2140                2145

Asp Asn Asn Glu Leu Ala Leu Ala Leu Glu Glu Pro Asp Leu Asp
2150                2155                2160

Lys Val Val Thr Tyr Leu Ala Gly Trp Gly Leu Gln Arg Cys Pro
2165                2170                2175

Val Leu Leu Ala Lys Gly Tyr Pro Asp Ile Gly Trp Asn Pro Ile
2180                2185                2190

Glu Gly Glu Arg Tyr Leu Ser Phe Leu Arg Phe Ala Val Phe Val
2195                2200                2205

Asn Ser Glu Ser Val Glu Glu Asn Ala Ser Val Val Val Lys Leu
2210                2215                2220

Leu Ile Arg Arg Pro Glu Cys Phe Gly Pro Glu Leu Arg Gly Glu
2225                2230                2235

Gly Gly Asn Gly Leu Leu Ala Ala Met Gln Glu Ala Ile Arg Ile
2240                2245                2250

Ser Glu Asn Pro Ser Arg Asp Leu Pro Ser Gln Gly Tyr Lys Arg
2255                2260                2265

Glu Gly Asp Glu Glu Glu Glu Glu Glu Ile Val His Met Gly
2270                2275                2280

Asn Ala Ile Met Ser Phe Tyr Ser Ala Leu Ile Asp Leu Leu Gly
2285                2290                2295

Arg Cys Ala Pro Glu Met His Leu Ile Gln Ser Gly Lys Gly Glu
2300                2305                2310

Ala Ile Arg Ile Arg Ser Ile Leu Arg Ser Leu Val Pro Thr Glu
2315                2320                2325

Asp Leu Val Gly Ile Ile Ser Ile Pro Leu Lys Leu Ser Thr Val
2330                2335                2340

Asn Lys Asp Gly Thr Val Asn Glu Pro Asp Met Ser Ala Asn Phe
2345                2350                2355

Cys Pro Asp His Lys Ala Pro Met Val Leu Phe Leu Asp Arg Val
2360                2365                2370

Tyr Gly Ile Lys Asp Gln Ser Phe Leu Leu His Leu Leu Glu Val
2375                2380                2385

Gly Phe Leu Pro Asp Leu Arg Ala Ser Ala Ser Leu Asp Thr Val
2390                2395                2400

Ser Leu Ser Thr Thr Glu Ala Ala Leu Ala Leu Asn Arg Tyr Ile
2405                2410                2415

Cys Ser Ala Val Phe Pro Leu Leu Lys Arg Cys Ala Pro Leu Phe
2420                2425                2430

Ser Gly Thr Glu His His Ala Ser Leu Val Asp Ser Met Leu His
2435                2440                2445

Thr Ile Tyr Arg Leu Ser Lys Gly Arg Ser Leu Thr Lys Ala Gln
2450                2455                2460

Arg Asp Thr Ile Glu Glu Cys Leu Leu Ala Ile Cys His His Leu
```

```
                2465                2470                2475
Arg Pro Ser Met Leu Gln Gln Leu Leu Arg Arg Leu Val Phe Asp
        2480                2485                2490
Val Pro Leu Leu Asn Glu Tyr Cys Lys Met Pro Leu Lys Leu Leu
        2495                2500                2505
Thr Asn His Tyr Glu Gln Cys Trp Lys Tyr Tyr Cys Leu Pro Ser
        2510                2515                2520
Gly Met Gly Ser Tyr Gly Ile Ala Ala Glu Asp Glu Leu His Leu
        2525                2530                2535
Thr Glu Lys Leu Phe Trp Gly Ile Phe Asp Ser Leu Ser His Lys
        2540                2545                2550
Lys Tyr Asp Pro Glu Leu Phe Arg Met Ala Leu Pro Cys Leu Ser
        2555                2560                2565
Ala Ile Ala Gly Ala Leu Pro Pro Asp Tyr Leu Asp Thr Arg Ile
        2570                2575                2580
Arg Ser Thr Leu Glu Lys Gln Thr Ser Val Asp Pro Glu Gly Asn
        2585                2590                2595
Phe Asp Pro Lys Pro Ile Asn Thr Ala Asn Leu Val Leu Pro Glu
        2600                2605                2610
Lys Leu Glu Tyr Ile Val Ser Lys Tyr Ala Glu His Ser His Asp
        2615                2620                2625
Lys Trp Ala Phe Asp Lys Thr Asn Asn Gly Trp Lys Tyr Gly Val
        2630                2635                2640
Ser Leu Asp Glu Asn Thr Lys Thr His Pro Leu Ile Arg Pro Phe
        2645                2650                2655
Lys Thr Leu Thr Glu Lys Glu Lys Glu Ile Tyr Arg Trp Pro Val
        2660                2665                2670
Arg Glu Ser Leu Lys Thr Met Leu Ala Met Gly Trp Ser Leu Glu
        2675                2680                2685
Arg Thr Lys Glu Gly Gly Glu Gly Met Leu His Gln Arg Glu Asn
        2690                2695                2700
Glu Lys Leu Arg Ser Ile Ser Gln Ser Ser Gln Gly Asn Gly Tyr
        2705                2710                2715
Ser Pro Ala Pro Leu Asp Leu Thr Asn Val Val Leu Ser Arg Glu
        2720                2725                2730
Leu Gln Gly Met Val Glu Val Met Ala Glu Asn Tyr His Asn Ile
        2735                2740                2745
Trp Ala Lys Lys Lys Met Glu Leu Glu Ser Lys Gly Gly Gly
        2750                2755                2760
Ser His Pro Leu Leu Val Pro Tyr Asp Thr Leu Thr Ala Lys Glu
        2765                2770                2775
Lys Ser Arg Asp Arg Glu Lys Ala Gln Glu Leu Phe Lys Phe Leu
        2780                2785                2790
Gln Val Asn Gly Ile Ile Ile Ser Arg Gly Leu Asn Asp Met Asp
        2795                2800                2805
Leu Asp Ala Ser Ser Met Glu Lys Arg Phe Ala Phe Lys Phe Leu
        2810                2815                2820
Lys Lys Ile Leu Lys Tyr Val Asp Ser Ala Gln Glu Phe Ile Ala
        2825                2830                2835
His Leu Glu Ala Ile Val Thr Ser Gly Lys Thr Glu Lys Ser Pro
        2840                2845                2850
His Asp Gln Glu Ile Lys Phe Phe Ala Lys Val Leu Leu Pro Leu
        2855                2860                2865
```

-continued

```
Val Asp Gln Tyr Phe Thr Asn His Cys Leu Tyr Phe Leu Ser Ser
    2870                2875                2880

Pro Thr Lys Thr Leu Ser Ser Ser Gly Tyr Ala Ser Asn Lys Glu
    2885                2890                2895

Lys Glu Met Val Ala Ser Leu Phe Cys Lys Leu Ala Ala Leu Val
    2900                2905                2910

Arg His Arg Ile Ser Ile Phe Gly Ser Asp Ser Thr Thr Met Val
    2915                2920                2925

Ser Cys Leu His Ile Leu Ala Gln Ser Leu Asp Thr Arg Thr Val
    2930                2935                2940

Met Lys Ser Gly Ser Glu Leu Val Lys Ala Gly Leu Arg Ala Phe
    2945                2950                2955

Phe Glu Asn Ala Ala Glu Asp Leu Glu Lys Thr Ser Glu Asn Leu
    2960                2965                2970

Lys Leu Gly Lys Phe Thr His Ser Arg Thr Gln Ile Lys Gly Val
    2975                2980                2985

Ser Gln Asn Ile Asn Tyr Thr Thr Val Ala Leu Leu Pro Val Leu
    2990                2995                3000

Thr Ser Ile Phe Glu His Ile Ser Gln Tyr His Phe Gly Val Asp
    3005                3010                3015

Leu Leu Leu Gly Asp Val Gln Val Ser Cys Tyr Arg Ile Leu Cys
    3020                3025                3030

Ser Leu Tyr Ser Leu Gly Thr Gly Lys Asn Ile Tyr Val Glu Arg
    3035                3040                3045

Gln Arg Pro Ala Leu Gly Glu Cys Leu Ala Ser Phe Ala Ala Ala
    3050                3055                3060

Ile Pro Val Ala Phe Leu Glu Pro Ser Leu Asn His Tyr Asn Pro
    3065                3070                3075

Leu Ser Val Phe Asn Thr Lys Ser Ala Arg Glu Arg Ala Ile Leu
    3080                3085                3090

Gly Met Pro Asp Thr Val Glu Glu Met Cys Pro Glu Ile Pro Gln
    3095                3100                3105

Leu Asp Gly Leu Ile Lys Glu Ile Asn Asn Leu Ala Glu Ser Gly
    3110                3115                3120

Ala Arg Tyr Thr Glu Met Pro His Val Ile Glu Val Ile Leu Pro
    3125                3130                3135

Met Leu Cys Asn Tyr Leu Ser Tyr Trp Trp Glu Arg Gly Ser Glu
    3140                3145                3150

Ser Val Pro Glu Ser Ala Gly Pro Cys Cys Thr Met Ile Thr Ser
    3155                3160                3165

Glu His Leu Ser Ile Ile Leu Gly Asn Ile Leu Lys Ile Ile Asn
    3170                3175                3180

Thr Asn Leu Gly Ile Asp Glu Ala Ser Trp Met Lys Arg Ile Ala
    3185                3190                3195

Val Tyr Ala Gln Pro Ile Ile Ser Lys Ala Arg Pro Asp Leu Leu
    3200                3205                3210

Lys Thr His Phe Ile Pro Thr Leu Glu Lys Leu Lys Lys Lys Ala
    3215                3220                3225

Ile Lys Ile Val Met Glu Glu Glu Gln Leu Arg Ala Asp Ser Lys
    3230                3235                3240

Ser Asp Thr Gln Glu Ala Glu Leu Leu Ile Leu Asp Glu Phe Ala
    3245                3250                3255
```

```
Val Leu Cys Arg Asp Leu Tyr Ala Phe Tyr Pro Met Leu Ile Arg
3260                3265                3270

Tyr Val Asp Asn Asn Arg Ala Asn Trp Leu Lys Lys Pro Asp Ala
3275                3280                3285

Asp Ser Asp Glu Leu Phe Arg Met Val Ala Glu Val Phe Ile Leu
3290                3295                3300

Trp Cys Lys Ser His Asn Phe Lys Arg Glu Glu Gln Asn Phe Val
3305                3310                3315

Ile Gln Asn Glu Ile Asn Asn Leu Ala Phe Leu Thr Gly Asp Thr
3320                3325                3330

Lys Ser Lys Met Ser Lys Ala Met Gln Val Lys Ser Gly Gly Gln
3335                3340                3345

Asp Gln Glu Arg Lys Lys Ser Lys Arg Gly Asp Leu Tyr Ser
3350                3355                3360

Ile Gln Thr Ser Leu Ile Val Ala Ala Leu Lys Lys Met Leu Pro
3365                3370                3375

Ile Gly Leu Asn Met Cys Thr Pro Gly Asp Gln Glu Leu Ile Ser
3380                3385                3390

Leu Ala Lys Thr Arg Tyr Ser His Lys Asp Thr Asp Glu Glu Val
3395                3400                3405

Lys Glu His Ile Arg Asn Asn Leu His Leu Gln Glu Lys Ser Asp
3410                3415                3420

Asp Pro Ala Val Lys Trp Gln Leu Asn Leu Tyr Lys Asp Ile Leu
3425                3430                3435

Lys Ser Asp Glu Pro Pro Asp Pro Glu Lys Asn Val Glu Arg Val
3440                3445                3450

Gln Arg Ile Ser Ala Ala Leu Tyr His Leu Asp Gln Val Glu Gln
3455                3460                3465

Pro Leu Arg Ser Lys Lys Ala Val Trp His Lys Leu Leu Ser Lys
3470                3475                3480

Gln Arg Lys Arg Ala Val Val Ala Cys Phe Arg Met Ala Pro Leu
3485                3490                3495

Tyr Asn Leu Pro Arg His Arg Ser Ile Asn Leu Phe Leu His Gly
3500                3505                3510

Tyr Gln Asn Tyr Trp Ile Glu Thr Glu Glu Tyr Ser Phe Glu Glu
3515                3520                3525

Lys Leu Val Gln Asp Leu Ala Thr Ser Pro Lys Lys Glu Glu Glu
3530                3535                3540

Glu Glu Glu Asp Thr Glu Lys Glu Gln Pro Asp Pro Leu His Gln
3545                3550                3555

Ile Ile Leu Tyr Phe Ser Arg Asn Ala Leu Thr Glu Arg Ser Lys
3560                3565                3570

Leu Glu Asp Asp Pro Leu Tyr Ile Ala Tyr Ala Ala Met Met Ala
3575                3580                3585

Lys Ser Cys Gln Glu Glu Glu Glu Glu Glu Asp Lys Glu
3590                3595                3600

Lys Thr Phe Glu Glu Lys Glu Met Glu Lys Gln Arg Thr Leu Tyr
3605                3610                3615

Gln Gln Ala Arg Leu His Asp Arg Gly Ala Ala Glu Met Val Leu
3620                3625                3630

Gln Met Ile Ser Ala Ser Lys Gly His Thr Gly Pro Met Val Val
3635                3640                3645

Glu Thr Leu Lys Leu Gly Ile Ala Ile Leu Asn Gly Gly Asn Thr
```

-continued

```
                 3650                3655                3660
Ile Val Gln Gln Lys Met Leu Asp Tyr Leu Lys Glu Lys Lys Asp
        3665                3670                3675
Ala Gly Phe Phe Gln Ser Leu Ser Gly Leu Met Gln Ser Cys Ser
        3680                3685                3690
Val Leu Asp Leu Asn Ala Phe Glu Arg Gln Asn Lys Ala Glu Gly
        3695                3700                3705
Leu Gly Met Val Thr Glu Glu Gly Thr Leu Ile Val Arg Glu Arg
        3710                3715                3720
Gly Glu Lys Val Leu Gln His Asp Glu Phe Thr Arg Asp Leu Phe
        3725                3730                3735
Arg Phe Leu Gln Leu Leu Cys Glu Gly His Asn Asn Asp Phe Gln
        3740                3745                3750
Asn Tyr Leu Arg Thr Gln Met Gly Asn Thr Thr Thr Val Asn Ile
        3755                3760                3765
Ile Ile Ser Thr Val Asp Tyr Leu Leu Arg Leu Gln Glu Ser Ile
        3770                3775                3780
Ser Asp Phe Tyr Trp Tyr Tyr Ser Gly Lys Glu Phe Ile Asp Glu
        3785                3790                3795
Ser Gly Gln Arg Asn Phe Ser Lys Ala Leu Ala Val Thr Lys Gln
        3800                3805                3810
Ile Phe Asn Ser Leu Thr Glu Tyr Ile Gln Gly Pro Cys Ile Gly
        3815                3820                3825
Asn Gln Gln Ser Leu Ala His Ser Arg Leu Trp Asp Ala Val Val
        3830                3835                3840
Gly Phe Leu His Val Phe Ala Asn Met Gln Met Lys Leu Ser Gln
        3845                3850                3855
Asp Ser Ala Gln Ile Glu Leu Leu Lys Glu Leu Leu Asp Leu Leu
        3860                3865                3870
Lys Asp Met Val Val Met Leu Leu Ser Leu Leu Glu Gly Asn Val
        3875                3880                3885
Val Asn Gly Thr Ile Gly Lys Gln Met Val Asp Thr Leu Val Glu
        3890                3895                3900
Ser Ser Ser Asn Val Glu Leu Ile Leu Lys Phe Phe Asp Met Phe
        3905                3910                3915
Leu Lys Leu Lys Asp Leu Thr Asn Ser Asp Ala Phe Lys Glu His
        3920                3925                3930
Asp Pro Asp Gly Lys Gly Ile Ile Ser Lys Lys Asp Phe Gln Lys
        3935                3940                3945
Ser Met Glu Ala Gln Lys Gln Tyr Ile Gln Ser Glu Ile Glu Phe
        3950                3955                3960
Leu Leu Ser Cys Thr Glu Ala Asp Glu Asn Asp Met Phe Asn Tyr
        3965                3970                3975
Ile Asp Phe Val Glu Arg Phe His Glu Pro Ala Lys Asp Ile Gly
        3980                3985                3990
Phe Asn Val Ala Val Leu Leu Thr Asn Leu Ser Glu His Met Pro
        3995                4000                4005
Asn Asp Ser Arg Leu Gln Ser Leu Leu Glu Pro Ala Glu Ser Val
        4010                4015                4020
Leu Asn Tyr Phe Glu Pro Tyr Leu Gly Arg Ile Glu Ile Met Gly
        4025                4030                4035
Gly Ala Lys Lys Ile Glu Arg Val Tyr Phe Glu Ile Ser Glu Ser
        4040                4045                4050
```

```
Ser Arg Met Gln Trp Glu Lys Pro Gln Val Lys Glu  Ser Lys Arg
    4055            4060            4065

Gln Phe Ile Phe Asp Val Val Asn Glu Gly Gly Glu  Gln Glu Lys
    4070            4075            4080

Met Glu Leu Phe Val Asn Phe Cys Glu Asp Thr Ile  Phe Glu Met
    4085            4090            4095

Gln Leu Ala Ser Gln Ile Ser Glu Thr Asp Ser Ala  Glu Arg Pro
    4100            4105            4110

Glu Glu Glu Glu Glu Glu Pro Cys Tyr Ile Val Asp  Ile Gly Asp
    4115            4120            4125

Asp Glu Glu Glu Glu Lys Ser Leu Glu Ser Pro Ser  Ala Phe Ala
    4130            4135            4140

Met Ala Cys Ala Ala Val Lys Lys Asn Val Ala Asn  Phe Phe Lys
    4145            4150            4155

Met Val Thr Val Lys Asn Leu Arg Lys Gln Tyr Arg  Lys Val Arg
    4160            4165            4170

Lys Met Thr Val Lys Glu Met Val Lys Val Phe Phe  Ser Phe Phe
    4175            4180            4185

Trp Ile Leu Phe Val Gly Val Phe Gln Leu Phe Phe  Thr Ile Val
    4190            4195            4200

Trp Gly Ile Phe Gln Ile Leu Trp Ser Thr Val Phe  Gly Gly Gly
    4205            4210            4215

Leu Val Glu Gly Ala Lys Asn Ile Lys Val Thr Lys  Ile Leu Gly
    4220            4225            4230

Asp Met Pro Asp Pro Thr Gln Phe Gly Ile His Asp  Asp Val Thr
    4235            4240            4245

Glu Ala Glu Lys Thr Glu Gly Ala Glu His Gly Ile  Arg Asp Glu
    4250            4255            4260

Leu Val Gln Phe Val Lys Gly Glu Lys Gly Glu Ala  Asp Ile Ile
    4265            4270            4275

Ser Asp Ile Phe Gly Ile Pro Thr Lys Lys Glu Gly  Gly Ser Lys
    4280            4285            4290

His Gly His Asp Ala Gly Leu Gly Asp Ile Ala Glu  Ile Leu Gly
    4295            4300            4305

Ser Asp Ile Gln Ser Ser Leu Glu Asn Asn Val Arg  Lys Lys Lys
    4310            4315            4320

Gly Leu Gln Thr Pro Glu Thr Ala Lys Asp Ala Glu  Ala Glu Arg
    4325            4330            4335

Lys Val Glu Ala Glu Lys Ala Asp Met Glu Asp Gly  Glu Lys Gln
    4340            4345            4350

Asp Lys Ala Lys Glu Glu His Ser Glu Gln Gln Glu  Glu Gly Lys
    4355            4360            4365

Thr Lys Lys Lys Lys Arg Arg His Gly Gln Lys Ile  Glu Lys Pro
    4370            4375            4380

Val Ala Val Met Ala Asn Phe Phe Lys Ala Leu Glu  Ile Tyr Gln
    4385            4390            4395

Thr Lys Met Leu His Tyr Leu Ala Arg Asn Phe Tyr  Asn Leu Arg
    4400            4405            4410

Phe Leu Ala Leu Phe Val Ala Phe Ala Ile Asn Phe  Ile Leu Leu
    4415            4420            4425

Phe Tyr Lys Val Thr Glu Glu Pro Leu Asp Glu Val  Glu Glu Asp
    4430            4435            4440
```

-continued

```
Ser Asn Leu Trp Asn Ser Phe Glu Glu Glu Glu Glu Glu Gly
4445                4450                4455

Met Val Phe Phe Val Leu Glu Glu Ser Thr Gly Tyr Met Ala Pro
4460                4465                4470

Thr Leu Arg Ala Leu Ala Val Ile His Thr Ile Ile Ser Phe Val
4475                4480                4485

Cys Val Ile Gly Tyr Tyr Cys Leu Lys Val Pro Leu Val Val Phe
4490                4495                4500

Lys Arg Glu Lys Glu Val Ala Arg Lys Leu Glu Phe Asp Gly Leu
4505                4510                4515

Tyr Ile Thr Glu Gln Pro Ser Glu Asp Asp Ile Lys Gly Gln Trp
4520                4525                4530

Asp Arg Leu Val Ile Asn Thr Pro Ser Phe Pro Asn Asn Tyr Trp
4535                4540                4545

Asp Lys Phe Val Lys Arg Lys Val Ile Asn Lys Tyr Gly Asp Leu
4550                4555                4560

Tyr Gly Ala Glu Arg Ile Ala Glu Leu Leu Gly Leu Asp Lys Asn
4565                4570                4575

Ala Leu Asp Phe Ser Pro Val Glu Glu Ser Glu Pro Glu Ala Ala
4580                4585                4590

Ser Leu Val Ser Trp Leu Ser Ser Ile Asp Thr Lys Tyr His Ile
4595                4600                4605

Trp Lys Leu Gly Val Val Phe Thr Asp Asn Ser Phe Leu Tyr Leu
4610                4615                4620

Ala Trp Tyr Thr Thr Met Ser Ile Leu Gly His Tyr Asn Asn Phe
4625                4630                4635

Phe Phe Ala Ala His Leu Leu Asp Ile Ala Met Gly Phe Lys Thr
4640                4645                4650

Leu Arg Thr Ile Leu Ser Ser Val Thr His Asn Gly Lys Gln Leu
4655                4660                4665

Val Leu Thr Val Gly Leu Leu Ala Val Val Tyr Leu Tyr Thr
4670                4675                4680

Val Val Ala Phe Asn Phe Phe Arg Lys Phe Tyr Asn Lys Ser Glu
4685                4690                4695

Asp Glu Asp Glu Pro Asp Met Lys Cys Asp Asp Met Met Thr Cys
4700                4705                4710

Tyr Leu Phe His Met Tyr Val Gly Val Arg Ala Gly Gly Gly Ile
4715                4720                4725

Gly Asp Glu Ile Glu Asp Pro Ala Gly Asp Pro Tyr Glu Ile Tyr
4730                4735                4740

Arg Ile Val Phe Asp Ile Thr Phe Phe Phe Phe Val Ile Val Ile
4745                4750                4755

Leu Leu Ala Ile Ile Gln Gly Leu Ile Ile Asp Ala Phe Gly Glu
4760                4765                4770

Leu Arg Asp Gln Gln Glu Gln Val Arg Glu Asp Met Glu Thr Lys
4775                4780                4785

Cys Phe Ile Cys Gly Ile Gly Asn Asp Tyr Phe Asp Thr Thr Pro
4790                4795                4800

His Gly Phe Glu Thr His Thr Leu Gln Glu His Asn Leu Ala Asn
4805                4810                4815

Tyr Leu Phe Phe Leu Met Tyr Leu Ile Asn Lys Asp Glu Thr Glu
4820                4825                4830

His Thr Gly Gln Glu Ser Phe Val Trp Lys Met Tyr Gln Glu Arg
```

```
                4835                4840                4845
Cys Trp Asp Phe Phe Pro Ala Gly Asp Cys Phe Arg Lys Gln Tyr
    4850                4855                4860

Glu Asp Gln Leu Gly
    4865
```

<210> SEQ ID NO 25
<211> LENGTH: 239
<212> TYPE: PRT
<213> ORGANISM: Meleagris gallopavo

<400> SEQUENCE: 25

```
Ile Leu His Gln Glu Gly His Met Asp Asp Ala Leu Ser Leu Ser Arg
1               5                   10                  15

Ser Gln Gly Glu Glu Ser Gln Ala Ala Arg Met Ile Tyr Ser Thr Ala
            20                  25                  30

Gly Leu Tyr Gly Ser Phe Ile Arg Ser Leu Asp Ala Leu Ser Ser Arg
        35                  40                  45

Gly Arg Gly Gly Gly Ala Gly Asn Ala Ala Leu Pro Ile Ala Ala Val
    50                  55                  60

Ile Leu Ser Leu Arg Asp Leu Ile Ala Tyr Phe Arg Ala Pro His Thr
65                  70                  75                  80

Glu Leu Gln His Glu Gln Arg Gln Asn Arg Leu Arg Ser Leu Arg Arg
                85                  90                  95

Arg Gln Asp Leu Phe Gln Gln Glu Gly Met Ile Ser Leu Val Leu Asn
            100                 105                 110

Cys Ile Asp Arg Leu Asn Val Tyr Ser Thr Ala Ala His Phe Ala Glu
        115                 120                 125

Phe Ala Gly Glu Glu Ala Ala Ala Ala Trp Lys Glu Ile Val Asn Leu
    130                 135                 140

Leu Tyr Glu Leu Leu Ala Ser Leu Ile Arg Gly Asn Arg Thr Asn Cys
145                 150                 155                 160

Ala Leu Phe Ser Thr Asn Leu Asp Trp Leu Val Ser Lys Leu Asp Arg
                165                 170                 175

Leu Glu Ala Ser Ser Gly Ile Leu Glu Val Leu Tyr Cys Val Leu Ile
            180                 185                 190

Glu Ser Pro Glu Val Leu Asn Ile Ile Gln Glu Asn His Ile Lys Ser
        195                 200                 205

Ile Ile Ser Leu Leu Asp Lys His Gly Arg Asn His Lys Val Leu Asp
    210                 215                 220

Val Leu Cys Ser Leu Cys Val Cys Asn Ala Val Ala Val Arg Ser
225                 230                 235
```

<210> SEQ ID NO 26
<211> LENGTH: 212
<212> TYPE: PRT
<213> ORGANISM: Meleagris gallopavo

<400> SEQUENCE: 26

```
Ile Leu His Gln Glu Gly His Met Asp Asp Ala Leu Ser Leu Ser Arg
1               5                   10                  15

Ser Gln Gly Glu Glu Ser Gln Ala Ala Arg Met Ile Tyr Ser Thr Ala
            20                  25                  30

Gly Leu Tyr Gly Ser Phe Ile Arg Leu Arg Asp Leu Ile Ala Tyr Phe
        35                  40                  45

Arg Ala Pro His Thr Glu Leu Gln His Glu Gln Arg Gln Asn Arg Leu
```

-continued

```
                50                  55                  60
Arg Ser Leu Arg Arg Gln Asp Leu Phe Gln Gln Glu Gly Met Ile
65                  70                  75                  80

Ser Leu Val Leu Asn Cys Ile Asp Arg Leu Asn Val Tyr Ser Thr Ala
                85                  90                  95

Ala His Phe Ala Glu Phe Ala Gly Glu Glu Ala Ala Ala Trp Lys
                100                 105                 110

Glu Ile Val Asn Leu Leu Tyr Glu Leu Leu Ala Ser Leu Ile Arg Gly
                115                 120                 125

Asn Arg Thr Asn Cys Ala Leu Phe Ser Thr Asn Leu Asp Trp Leu Val
                130                 135                 140

Ser Lys Leu Asp Arg Leu Glu Ala Ser Ser Gly Ile Leu Glu Val Leu
145                 150                 155                 160

Tyr Cys Val Leu Ile Glu Ser Pro Glu Val Leu Asn Ile Ile Gln Glu
                165                 170                 175

Asn His Ile Lys Ser Ile Ser Leu Leu Asp Lys His Gly Arg Asn
                180                 185                 190

His Lys Val Leu Asp Val Leu Cys Ser Leu Cys Val Cys Asn Ala Val
                195                 200                 205

Ala Val Arg Ser
    210
```

<210> SEQ ID NO 27
<211> LENGTH: 168
<212> TYPE: PRT
<213> ORGANISM: Meleagris gallopavo

<400> SEQUENCE: 27

```
Ile Leu His Gln Glu Gly His Met Asp Asp Ala Leu Ser Leu Ser Arg
1               5                   10                  15

Ser Gln Gly Glu Glu Ser Gln Ala Ala Arg Met Ile Tyr Ser Thr Ala
                20                  25                  30

Gly Leu Tyr Gly Ser Phe Ile Arg Gly Ser Pro Trp Cys Thr Ala Ser
                35                  40                  45

Thr Gly Thr Cys Thr Ala Arg Pro Arg Thr Ser Pro Ser Ser Pro Gly
                50                  55                  60

Arg Arg Arg Arg Pro Pro Gly Arg Arg Ser Ser Thr Ser Ser Met Ser
65                  70                  75                  80

Cys Trp Arg Arg Ser Gly Gly Thr Glu Pro Thr Ala Pro Cys Ser Pro
                85                  90                  95

Pro Thr Trp Thr Gly Trp Ser Ala Asn Trp Thr Gly Trp Arg Arg Arg
                100                 105                 110

Gln Gly Ser Trp Arg Cys Phe Thr Ala Ser Ser Arg Ala Pro Arg Phe
                115                 120                 125

Thr Ser Ser Arg Arg Thr Thr Ser Ser Pro Ser Ser Pro Cys Trp Thr
130                 135                 140

Asn Thr Ala Ala Thr Ile Arg Ser Trp Thr Cys Ser Ala Leu Cys Val
145                 150                 155                 160

Ser Ala Met Leu Trp Pro Phe Val
                165
```

GENETIC TEST FOR PSE-SUSCEPTIBLE TURKEYS

This application for patent under 35 U.S.C. § 111(a) claims priority to Provisional Application Ser. No. 60/540,490 filed on Jan. 30, 2004 under 35 U.S.C. § 111(b).

FIELD OF THE INVENTION

This invention relates to methods and compounds for the improvement of turkey meat and turkey populations, but not limited to, a genetic screen to select for turkeys that produce a better quality of meat characterized by a higher postmortem pH and better water holding capacity.

BACKGROUND

The breeding of food animals for certain qualities desired by breeders, farmers and consumers can have the unintentional side effect of selecting for less desirable characteristics. For example, by breeding for animals that produce large amounts of meat quickly, breeders have also selected for animals that may have meat qualities that consumers find less than desirable. Both turkey and pork meat can have what is termed pale, soft and exudative (PSE) meat. PSE meat is characterized by an abnormally light color, a flaccid consistency and poor water holding capacity. These characteristics make the meat hard to process in packing facilities and consumers find meat with these characteristics less than desirable. It is estimated that the problem of PSE meat costs the poultry industry alone millions of dollars a year.

Presently, the poultry industry deals with the problem of PSE turkey meat in ineffective ways. For example, some people in the field have suggested alternative meat processing or transportation schemes to improve the qualities of PSE turkey meat (Alvarado, C. Z., A. R. Sams, "The Role of Carcass Chilling Rate in the Development of Pale, Exudative Turkey Pectoralis" *Poultry Science* 81:1365-1370, 2002; Owens, C. M. and A. R. Sams, "The Influence of Transportation on Turkey Meat Quality" *Poultry Science* 79:1204-1207, 2000). These suggestions have had only marginal impact on relieving the problem. At least one method of testing for turkeys prone to developing PSE meat has been proposed (Wheeler, et al., "A Halothane Test to Detect Turkeys Prone to Developing Pale, Soft and Exudative Meat" *Poultry Science* 78:1634-1638, 1999). However, the test did not identify PSE turkeys consistently. Others have proposed treating PSE meat after slaughter to make it more appealing to the consumer (U.S. Pat. No. 5,928,689 to Mikowski, et al.; U.S. Pat. No. 6,020,012 to Kauffman, et al.) However, even when these methods are successful, the quality of the treated PSE meat is still substandard as compared to non-PSE meat.

What is needed is an effective method by which turkeys that produce a better quality of meat can be identified and selected before farmers undergo the expense of raising the turkeys to maturity or using them used for breeding purposes.

SUMMARY OF THE INVENTION

This invention relates to methods and compounds for the improvement of turkey meat and turkey populations including, but not limited to, a genetic screen to select for turkeys that produce a better quality of meat characterized by a higher postmortem pH and a better water holding capacity. In one embodiment, selective breeding is contemplated for turkeys having a genotype that is associated with better meat quality.

In one embodiment, the present invention contemplates a method for the identification of turkeys that produce a better quality of meat when compared to PSE meat.

In one embodiment of the present invention, turkeys that are homozygous for αRYR-II have superior meat quality as compared to turkeys that are homozygous for αRYR-I or turkeys that are heterozygous for αRYR-II and αRYR-I. In this regard, in another embodiment, the present invention contemplates genetic screens for turkeys to identify turkeys that are homozygous for αRYR-II and αRYR-I or heterozygous.

One embodiment of the present invention comprises three novel variants of the αRYR alleles. The variants are referred to as W, AS-81 and AS-193. Additionally, an embodiment of the present invention comprises two αRYR alleles found by investigating turkey αRYR genomic DNA in the region corresponding to the transcript variants. In another embodiment, each of these alleles may be expressed as any of the three variants. Yet another embodiment of the present invention comprises characterization of the heterogeneity of turkey αRYR transcript variants, the two αRYR alleles, and the relationship of the expression pattern of the transcript variants to the two alleles. Still yet another embodiment of the present invention comprises a correlation of meat quality and traits with the turkey genotypes.

In one embodiment, the present invention contemplates a method of genotyping turkeys, comprising: a) providing nucleic acid samples from a plurality of turkeys; and b) genotyping said samples under conditions such that turkeys homozygous for TαRYRII are identified. In another embodiment, the present invention contemplates the method, wherein said genotyping comprises nucleic acid amplification. In yet another embodiment, the present invention contemplates the method, wherein said amplification comprises PCR utilizing a forward primer and a reverse primer. In still yet another embodiment, the present invention contemplates the method, wherein the sequence of said forward primer is set forth in SEQ ID NO:13. In still yet another embodiment, the present invention contemplates the method, wherein the sequence of said reverse primer is set forth in SEQ ID NO:14. In still yet another embodiment, the present invention contemplates the method, wherein said nucleic acid samples are obtained from muscle tissue. In still yet another embodiment, the present invention contemplates the method, wherein said muscle tissue is turkey breast muscle. In still yet another embodiment, the present invention contemplates the method, wherein said samples are taken from slaughtered turkeys. In still yet another embodiment, the present invention contemplates the method, wherein said samples are taken from live turkeys. In still yet another embodiment, the present invention contemplates the method, wherein said live turkeys identified as homozygous for TαRYRII are used for breeding. In still yet another embodiment, the present invention contemplates the method, wherein said live turkeys are young turkeys. In still yet another embodiment, the present invention contemplates the method, wherein said live young turkeys identified as homozygous for TαRYRII are subsequently grown to maturity. In still yet another embodiment, the present invention contemplates the method, wherein said live turkeys are mature turkeys. In still yet another embodiment, the present invention contemplates the method, wherein said live mature turkeys identified as homozygous for TαRYRII are slaughtered for commercial meat production.

In one embodiment, the present invention contemplates a method of selecting turkeys for meat production based on genotyping, comprising: a) providing nucleic acid samples from a plurality of live turkeys; b) genotyping said samples under conditions such that turkeys are identified that are i) homozygous for TαRYRII, ii) homozygous for TαRYRI, iii) heterozygous for TαRYRII, and iv) heterozygous for TαRYRI; and c) selecting said live turkeys identified as homozygous for TαRYRII for meat production. In another embodiment, the present invention contemplates the method of claim 15, wherein said genotyping comprises nucleic acid amplification. In yet another embodiment, the present invention contemplates the method, wherein said amplification comprises PCR utilizing a forward primer and a reverse primer. In still yet another embodiment, the present invention contemplates the method, wherein the sequence of said forward primer is set forth in SEQ ID NO:13. In still yet another embodiment, the present invention contemplates the method, wherein the sequence of said reverse primer is set forth in SEQ ID NO:14. In still yet another embodiment, the present invention contemplates the method, wherein said nucleic acid samples are obtained from muscle tissue. In still yet another embodiment, the present invention contemplates the method, wherein said muscle tissue is turkey breast muscle. In still yet another embodiment, the present invention contemplates the method, wherein said selecting for meat production comprises slaughtering said selected turkeys. In still yet another embodiment, the present invention contemplates the method, wherein said selecting for meat production comprises utilizing said turkeys identified as homozygous for TαRYRII for breeding. In still yet another embodiment, the present invention contemplates the method, wherein said live turkeys are young turkeys. In still yet another embodiment, the present invention contemplates the method, wherein said selecting for meat production comprises growing said turkeys identified as homozygous for TαRYRII to maturity. In still yet another embodiment, the present invention contemplates the method, wherein said turkeys identified as homozygous for TαRYRI are not used for meat production. In still yet another embodiment, the present invention contemplates the method, wherein said genotyping is performed with an assay selected from a group consisting of Southern blotting, Northern blotting, and nucleic acid sequencing.

In one embodiment, the present invention contemplates a method of identifying turkeys expressing protein encoded by TαRYRII, comprising: a) providing samples from a plurality of turkeys; and b) testing said samples under conditions such that turkeys expressing protein encoded by TαRYRII are identified. In another embodiment, the present invention contemplates the method, wherein said testing is performed with an assay selected from a group consisting of Western blotting, immunohistochemistry, and amino acid sequencing.

In one embodiment, the present invention contemplates a kit for genotyping turkeys, comprising primers capable of amplifying nucleic acid such that turkeys homozygous for TαRYRII can be identified. In another embodiment, the present invention contemplates the kit, wherein said kit comprises a forward PCR primer and a reverse PCR primer. In yet another embodiment, the present invention contemplates the kit, wherein the sequence of said forward primer is set forth in SEQ ID NO:13. In still yet another embodiment, the present invention contemplates the kit, wherein the sequence of said reverse primer is set forth in SEQ ID NO:14.

The present invention further provides a method for screening compounds for the ability to alter turkey RYR activity, comprising: providing: a first polypeptide sequence comprising at least a portion of turkey RYR; ii) a second polypeptide sequence comprising at least a portion of a protein known to interact with turkey RYR; and iii) one or more test compounds; combining in any order, the first polypeptide sequence comprising at least a portion of turkey RYR, the second polypeptide sequence comprising at least a portion of a protein known to interact with turkey RYR, and one or more test compounds under conditions such that the first polypeptide sequence, the second polypeptide sequence, and the test compound interact; and detecting the presence or absence of an interaction between the polypeptide sequence comprising at least a portion of turkey RYR and the polypeptide sequence comprising at least a portion of a protein known to interact with turkey RYR. In some embodiments, the first polypeptide sequence is selected from the group consisting of SEQ ID NOS: 5, 6 and 7. In some embodiments, the second polypeptide comprises DHPR.

The present invention also provides a method of identifying turkeys showing fewer symptoms of PSE meat production comprising: providing nucleic acid from an animal, wherein the nucleic acid comprises a turkey RYR allele and detecting a mutation in the nucleic acid, wherein the mutation results in a reduction in PSE meat symptoms. In some embodiments, the mutation is in the turkey RYR allele. In some embodiments, the mutation is a nucleotide residue insertion or deletion. In some embodiments, the detecting step is accomplished by hybridization analysis (e.g., Southern blotting and Northern blotting).

In yet other embodiments, the present invention provides a kit for determining if a subject is homozygous for the αRYR-II allele comprising: at least one reagent that specifically detects if a turkey is homozygous for the αRYR-II allele; and instructions for determining that the subject is homozygous for the αRYR-II allele.

The present invention also provides a purified polypeptide (or portion thereof) selected from the group consisting of SEQ ID NOS: 5, 6 and 7.

In one embodiment, the present invention contemplates a method of screening for turkeys homozygous for TαRYRII, comprising: a) providing, i) a sample from a subject and, ii) an assay for the detection of TαRYRI; b) testing said sample for the presence of TαRYRI. In another embodiment, the present invention contemplates that the method additionally comprises: a) an assay for the detection of TαRYRII and; b) testing for said sample for the presence of TαRYRII. In yet another embodiment, the present invention contemplates non-limiting examples of the assay that used for the detection of presence of TαRYRI and TαRYRII. For example, the assay can be selected from Western blotting, Southern blotting, Northern blotting, immunoassays, PCR, nucleotide sequencing, amino acid sequencing and yeast two-hybrid screening. In yet another embodiment, the present invention contemplates that the sample used in the assay comprises a nucleotide sequence encoding at least a portion of the TαRYRI protein and said nucleotide sequence is amplified before said assay.

In one embodiment, the present invention contemplates a method for detection of a polynucleotide encoding protein in a biological sample comprising the steps of: a) providing: i) a sample comprising a first polynucleotide from a subject and, ii) a second polynucleotide sequence selected from the group consisting of polynucleotide sequences encoding at least a portion of SEQ ID NO: 5, 6 or 7; b) combining said first and second nucleotides to form a hybridization complex; and c) detecting said hybridization complex. In another embodiment, the present invention contemplates that the assay is selected from a group consisting of Southern blotting, Northern blotting, PCR and nucleotide sequencing.

In one embodiment, the present invention contemplates a method for screening compounds for the ability to alter TαRYRI activity, comprising: a) providing: i) a first polypeptide sequence comprising at least a portion of TαRYRI; ii) a second polypeptide sequence comprising at least a portion of a protein known to interact with TαRYRI; and iii) one or more test compounds; b) combining in any order, said first polypeptide sequence comprising at least a portion of TαRYRI, said second polypeptide sequence comprising at least a portion of a protein known to interact with TαRYRI, and said one or more test compounds under conditions such that said first polypeptide sequence, said second polypeptide sequence, and said test compound interact; and c) detecting the presence or absence of an interaction between said polypeptide sequence comprising at least a portion of TαRYRI and said polypeptide sequence comprising at least a portion of a protein known to interact with TαRYRI. In another embodiment, the present invention contemplates that first polypeptide sequence is selected from the group consisting of SEQ ID NOS: 5, 6 and 7. in yet another embodiment, the present invention contemplates that the second polypeptide comprises DHPR.

In one embodiment, the present invention contemplates a compound comprising a purified polypeptide or portion thereof selected from the group consisting of SEQ ID NOs: 5, 6 and 7. In another embodiment, the present invention contemplates that the purified polypeptide encoded by SEQ ID NOS 5, 6 and 7 encodes allele αRYRI or αRYRII.

DEFINITIONS

The terms "protein," "peptide" and "polypeptide" refer to compounds comprising amino acids joined via peptide bonds and are used interchangeably. A "protein," "peptide" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide," "peptide" or "protein" are not meant to limit the amino acid sequence to the complete, native amino acid sequence associated with the recited protein molecule. Furthermore, an "amino acid sequence" can be deduced from the nucleic acid sequence encoding the protein. Detecting amino acids sequences encoded by the turkey RYR gene or portions thereof is contemplated by one embodiment of the present invention.

The term "portion" when used in reference to a protein (as in "a portion of a given protein") refers to fragments of that protein. The fragments may range in size from four amino acid residues to the entire amino sequence minus one amino acid. The term "potion" when used in reference to a nucleic acid (as in "a portion of a given nucleic acid") refers to fragments of that nucleic acid. The fragments may range in size from ten bases to the entire nucleic acid sequence minus one base.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences includes those obtained from the same or from different species of organisms.

In one embodiment of the present invention it is contemplated that exogenous genes expressing the protein encoded by the αRYRII allele will be used to produce transgenic animals. The expressed exogenous proteins may be part of a fusion protein. The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80% sequence identity, preferably at least 90% sequence identity, more preferably at least 95% sequence identity or more (e.g., 99% sequence identity). Preferably, residue positions which are not identical differ by conservative amino acid substitutions.

In one embodiment of the present invention it is contemplated that varients of the αRYR gene (i.e., w, as-81 and as-193) may be used for, e.g., transfections. The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, preferably less than 5% and still more preferably less than 2% changes (whether substitutions, deletions, and so on).

The term "domain" when used in reference to a polypeptide refers to a subsection of the polypeptide which possesses a unique structural and/or functional characteristic; typically, this characteristic is similar across diverse polypeptides. The subsection typically comprises contiguous amino acids, although it may also comprise amino acids which act in concert or which are in close proximity due to folding or other configurations.

In one embodiment of the present invention contemplates several genes (e.g., αRYR and βRYR). The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene.

In one embodiment of the present invention it is contemplated that the genes of the present invention comprise introns and exons. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

In particular, the term "TαRYR gene" refers to a full-length TαRYR nucleotide sequence (e.g., FIG. 6). However, it is also intended that the term encompass fragments of TαRYR, as well as other domains with the full-length nucleotide sequence. Furthermore, the terms "TαRYR nucleotide sequence" or "TαRYR polynucleotide sequence" encompass DNA, cDNA, and RNA (e.g., mRNA) sequences. Further still, the term TαRYR is synonymous with "Turkey αRYR" and refers to both TαRYRI and TαRYRII unless specified otherwise.

In one embodiment of the present invention, it is contemplated that the nucleic acids encoding the RYR peptides may be expressed in organisms or cells that are not derived from turkeys. The term "heterologous," when used in reference to a gene, refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise, e.g., plant or animal gene sequences that comprise cDNA forms of a plant or animal gene; the cDNA sequences may be expressed in either a sense (to produce mRNA) or anti-sense orientation (to produce an anti-sense RNA transcript that is complementary to the mRNA transcript). Heterologous genes are distinguished from endogenous genes in that the heterologous gene sequences are typically joined to nucleotide sequences comprising regulatory elements such as promoters that are not found naturally associated with the gene for the protein encoded by the heterologous gene or with gene sequences in the chromosome, or are associated with portions of the chromosome not found in nature (e.g., genes expressed in loci where the gene is not normally expressed). In the present invention, it is contemplated that the nucleotide sequence that encodes TαRYR (FIG. 6) and portions thereof may comprise a heterologous gene. For example, the TαRYR sequence may be joined to promoter specific for muscle tissues. Examples of such promoters include, but are not limited to the ankyrin 1 muscle promoter, the desmin gene promoter, the actin promoter and the myosin promoter.

In one embodiment of the present invention, it is contemplated that a portion of the RYR nucleic acid sequence (i.e., a "nucleic acid sequence of interest") may be used. The term "nucleotide sequence of interest" or "nucleic acid sequence of interest" refers to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

The term "structural" when used in reference to a gene or to a nucleotide or nucleic acid sequence refers to a gene or a nucleotide or nucleic acid sequence whose ultimate expression product is a protein (such as an enzyme or a structural protein), an rRNA, an sRNA, a tRNA, etc.

The terms "oligonucleotide" or "polynucleotide" or "nucleotide" or "nucleic acid" refer to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof. The terms "an oligonucleotide having a nucleotide sequence encoding a gene" or "a nucleic acid sequence encoding" a specified polypeptide refer to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

In one embodiment of the present invention, it is contmeplated that recombinant techniques are used with the nucleic acid sequences of the present invention. The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The following terms are used to describe the sequence relationships between two or more polynucleotides: "reference sequence," "sequence identity," "percentage of sequence identity" and "substantial identity." A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20% or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci.* (U.S.A.) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95% sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

The term "substantially homologous" when used in reference to a double-stranded nucleic acid sequence such as a cDNA or genomic clone refers to any probe that can hybridize to either or both strands of the double-stranded nucleic acid sequence under conditions of low to high stringency as described above.

The term "substantially homologous" when used in reference to a single-stranded nucleic acid sequence refers to any probe that can hybridize (i.e., it is the complement of) the single-stranded nucleic acid sequence under conditions of low to high stringency as described above.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% G+C)$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

In one embodiment of the present invention, it is contemplated that assays will be used for genotyping with, for example, labeled probes. In this regard, complementary sequences will hybridize to each other. Hybridization may occur at different stringencies. The term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$(H$_2$O and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$(H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0×SSPE, 1.0% SDS at 42° C. when a probe of about 500 nucleotides in length is employed.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$(H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is often the gene which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identifiable since they have altered characteristics when compared to the wild-type gene or gene product. In the present invention, FIG. 6 comprises one allele of the wild-type gene.

Thus, the terms "variant" and "mutant" when used in reference to a nucleotide sequence refer to an nucleic acid sequence that differs by one or more nucleotides from another, usually related nucleotide acid sequence. A "variation" is a difference between two different nucleotide sequences; typically, one sequence is a reference sequence. In the present invention, W, AS-81 and AS-193 are example of variants of the RYR gene.

The term "polymorphic locus" refers to a genetic locus present in a population that shows variation between members of the population (i.e., the most common allele has a frequency of less than 0.95). Thus, "polymorphism" refers to the existence of a character in two or more variant forms in a population. A "single nucleotide polymorphism" (or SNP) refers a genetic locus of a single base which may be occupied by one of at least two different nucleotides. In contrast, a "monomorphic locus" refers to a genetic locus at which little or no variations are seen between members of the population (generally taken to be a locus at which the most common allele exceeds a frequency of 0.95 in the gene pool of the population).

A "frameshift mutation" refers to a mutation in a nucleotide sequence, usually resulting from insertion or deletion of a single nucleotide (or two or four nucleotides) which results in a change in the correct reading frame of a structural DNA sequence encoding a protein. The altered reading frame usually results in the translated amino-acid sequence being changed or truncated. The AS-193 variant of the present invention is believed to have a frameshift mutation that produces a premature stop codon after amino acid 416.

A "splice mutation" refers to any mutation that affects gene expression by affecting correct RNA splicing. Splicing mutation may be due to mutations at intron-exon boundaries which alter splice sites. The W, AS-81 and AS-193 variants of the present invention are believed to be the result of splice mutations.

The term "detection assay" refers to an assay for detecting the presence or absence of a sequence or a variant nucleic acid sequence (e.g., mutation or polymorphism in a given allele of a particular gene, as e.g., TαRYR gene [FIG. 6]), or for detecting the presence or absence of a particular protein (e.g., TβRYR [SEQ ID NO: 5]) or the structure or activity or effect of a particular protein (e.g., a binding assay or activity assay) or for detecting the presence or absence of a variant of a particular protein.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

In one embodiment of the present invention, it is contemplated that the nucleotide sequences of the present invention may be "amplified". "Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out. Examples of amplification include, but are not limited to, PCR and the INVADER® assay (Third Wave Technologies, Madison Wis.).

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian, et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlain, et al., Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridizaiton with the target sequences and not hybridization with non-target sequences (H. A. Erlich (ed.), PCR Technology, Stockton Press [1989]).

The term "amplifiable nucleic acid" refers to nucleic acids that may be amplified by any amplification method. It is contemplated that "amplifiable nucleic acid" will usually comprise "sample template." Examples of amplification include, but are not limited to, PCR and the INVADER® assay (Third Wave Technologies, Madison Wis.).

Allele specific nucleic acid sequences may also be identified by hybridizaiton with crosslinkable oligonucleotide probes as disclosed in U.S. Pat. No. 5,652,096 to G. D. Cimino, which is herein incorporated by reference.

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

In one embodiment of the present invention, it is contemplated that primers will be used for the amplification of nucleic acid sequences. Examples of such primers are SEQ ID NOS: 13, 14, 15 an 16. The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

In one embodiment of the present invention, it is contemplated that turkeys will be identified for being homozygous for the αRYRII allele via PCR amplification. The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

One embodiment of the present invention contemplates reverse-transcription of turkey RYR mRNA. The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

The term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and into protein, through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination," "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

In one embodiment of the present invention, it is contemplated that the genes and alleles of the present invention may comprise promoters regulator elements and enhancer elements. Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987). In the present invention, it is contemplated that, for example, the TαRYR gene may be joined to promoter specific for muscle tissues of skeletal tissues. Examples of such promoters include, but are not limited to the ankyrin 1 muscle promoter, the desmin gene promoter, the actin promoter and the myosin promoter. Additionally, it is contemplated that the TαRYR gene may be joined to a constitutive promoter or an inducible promoter (both defined below) or to a promoter specific for other cell or tissue types (defined below) (e.g., promoters specific for muscle or skin).

The terms "promoter element," "promoter," or "promoter sequence" refer to a DNA sequence that is located at the 5' end (i.e. precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer, and is typically between about 500 bp and 4 kb in length, and is preferably about 1 to 1.5 kb in length.

Promoters may be tissue specific or cell specific. Examples of promoters specific for muscle tissues are given above. The term "tissue specific" as it applies to a promoter refers to a promoter that is capable of directing selective expression of a nucleotide sequence of interest to a specific type of tissue (e.g., muscle) in the relative absence of expression of the same nucleotide sequence of interest in a different type of tissue (e.g., bone). Tissue specificity of a promoter may be evaluated by, for example, operably linking a reporter gene to the promoter sequence to generate a reporter construct, introducing the reporter construct into the genome of an organism such that the reporter construct is integrated into every tissue of the resulting transgenic organism, and detecting the expression of the reporter gene (e.g., detecting mRNA, protein, or the activity of a protein encoded by the reporter gene) in different tissues of the transgenic organism. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or inducible. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue.

In contrast, an "inducible" promoter is one which is capable of directing a level of transcription of an operably linked nucleic acid sequence in the presence of a stimulus (e.g., heat shock, chemicals, light, etc.) which is different from the level of transcription of the operably linked nucleic acid sequence in the absence of the stimulus.

The term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, etc.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species).

The term "naturally linked" or "naturally located" when used in reference to the relative positions of nucleic acid sequences means that the nucleic acid sequences exist in nature in the relative positions.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual*, 2nd ed., Cold Spring Harbor Laboratory Press, New York [1989] pp. 16.7-16.8). An example of a commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook, supra, at 16.6-16.7).

The term "vector" refers to nucleic acid molecules that transfer DNA segment(s) from one cell to another. The term "vehicle" is sometimes used interchangeably with "vector." In one embodiment, vectors comprising the sequences and portions of sequences of the present invention are contemplated.

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

In one embodiment of the present invention, it is contemplated that the sequences of the present invention (and portions thereof) may be used in in transfection protocols. The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The terms "infecting" and "infection" when used with a bacterium refer to co-incubation of a target biological sample, (e.g., cell, tissue, etc.) with the bacterium under conditions such that nucleic acid sequences contained within the bacterium are introduced into one or more cells of the target biological sample.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are incorporated herein by reference), and are commercially available (e.g., the helium gas-driven microprojectile accelerator (PDS-1000/He, BioRad).

The term "transgene" refers to a foreign gene (e.g., αRYR and βRYR) that is placed into an organism by the process of transfection. The term "foreign gene" refers to any nucleic acid (e.g., gene sequence) that is introduced into the genome of an organism by experimental manipulations and may include gene sequences found in that organism so long as the introduced gene does not reside in the same location as does the naturally-occurring gene.

The term "transgenic" when used in reference to a host cell or an organism refers to a host cell or an organism that contains at least one heterologous or foreign gene in the host cell or in one or more of cells of the organism.

The term "host cell" refers to any cell capable of replicating and/or transcribing and/or translating a heterologous gene. Thus, a "host cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal. In the present invention, it is contemplated that host cells are, for example, myoblasts, and myocytes.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotrasferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos. 6,074,859; 5,976, 796; 5,674,713; and 5,618,682; all of which are incorporated herein by reference), green fluorescent protein (e.g., Gen-Bank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

In one embodiment, the present invention contemplates the overexpressionog the turkey RYR genes. The term "overexpression" refers to the production of a gene product in transgenic organisms that exceeds levels of production in normal or non-transformed organisms. The term "cosuppression" refers to the expression of a foreign gene which has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

In one embodiment, the present invention contemplates a method of geneotyping turkeys comprising: a) providing nucleic acid samples from a plurality of turkeys; and b) genotyping said samples under conditions such that turkeys homozygous for TaRYRII are identified by, for example, Southern blotting, Northern blotting and nucleic acid sequencing. The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. [1989] *Molecular Cloning: A Laboratory Manual*, Cold Spring Harbor Press, NY, pp 9.31-9.58). Genotyping may be performed via Southern blotting. This may be performed by testing for the hybridization of a complementary test sequence (i.e., a probe for αRYRI or αRYRII) to the subject DNA.

The term "Northern blot analysis" and "Northern blot" and "northern" refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. [1989] supra, pp 7.39-7.52). Genotyping may be performed via Northern blotting. This may be performed by testing for the hybridization of a complementary test sequence (i.e., a probe for αRYRI or αRYRII) to the subject RNA.

In one embodiment, the present invention contemplates a method of geneotyping turkeys comprising: a) providing nucleic acid samples from a plurality of turkeys; and b) genotyping said samples under conditions such that turkeys homozygous for TaRYRII are identified by, for example, Western blotting and peptide sequencing. The terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies. Genotyping may be performed via Western blotting. This may be performed by testing for the recognition of a probe (i.e., an antibody for αRYRI or αRYRII) to the subject peptides.

The term "antigenic determinant" refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

In one embodiment, the present invention contemplates isolated transcripts. The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

In one embodiment, the present invention contemplates purified nucleic acid and amino acid sequences. The term "purified" refers to molecules, either nucleic or amino acid sequences, that are removed from their natural environment, isolated or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

One embodiment of the present invention contemplates that nucleic acids, peptides, vectors, antibodies, etc, of the present invention may comprise part of a composition. The term "composition comprising" a given polynucleotide sequence or polypeptide refers broadly to any composition containing the given polynucleotide sequence or polypeptide. The composition may comprise an aqueous solution. Compositions comprising polynucleotide sequences encoding TαRYR (e.g., SEQ ID NOS:5, 6 and 7) or fragments thereof may be employed as hybridization probes. In this case, the TαRYR encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

As used herein, the term "response," when used in reference to an assay, refers to the generation of a detectable signal (e.g., accumulation of reporter protein, increase in ion concentration, accumulation of a detectable chemical product).

The term "sample" is used in its broadest sense. In one sense it can refer to a cell or tissue. In another sense, it is meant to include a specimen or culture obtained from any source and encompass fluids, solids and tissues. Environmental samples include environmental material such as surface matter, soil, water, and industrial samples. These examples are not to be construed as limiting the sample types applicable to the present invention.

One embodiment of the present invention contemplates the genotyping of turkeys. "Genotyping" shall be defined as determining the genetic constitution of an organism or cell, as distinct from its expressed features or phenotype. Genotyping need not include the determination of all genetic constituents of a cell or organism. Indeed, only one genetic marker need be determined (e.g., αRYR) to identify the genotype of a cell or organism as an embodiment of the present invention.

"Slaughter" and "slaughtered" shall be defined as the killing of animals for food or research purposes or for the practice of certain health control measures.

"Used for breeding" shall be defined as the controlled mating of animals (e.g., turkeys) for the purpose of, for example, acquiring offspring of a certain genotype or phenotype. For example, the selected turkeys identified as homozygous for αRYRII are bred with other turkeys selected as homozygous for αRYRII. "Young turkeys" shall be defined as turkeys that are not fully grown or matured. The National Turkey Federation defines a young turkey as a hen under about 15 pounds and less than about 14 weeks of age. A young Tom turkey is defined as being under about 32 pounds and less than 18 weeks of age. A "mature" turkey is a turkey at about or over these weights and ages.

"Commercial meat production" shall be defined as the growing of turkeys for slaughter for food and encompasses the growing of young turkeys (of a particular genotype) to maturity before slaughter as well as the slaughtering of young turkeys.

"Selecting turkeys" shall be defined as, for example, the identification of a turkey or group of turkeys that share, e.g., a similar or identical genotype for at least one gene. The turkeys may be (but need not be) separated from other turkeys not sharing the genotype selected for. Turkeys may also be selected based on phenotype or an(other) characteristic(s).

"Immunohistochemistry" shall be defined as, for example, the histochemical localization of immunoreactive substances using labelled antibodies as reagents

BRIEF DESCRIPTION OF THE DRAWINGS

FIG. 1 shows the alignment of turkey αRYR amino acid sequence with published skeletal muscle RYR isoforms. Amino acid residues of turkey αRYR (SEQ ID NO:5) (TαRYR; see, FIG. 6) from 376-615 were compared to human RYR1 (HRYR1; accession no. AAA60294), pig RYR1 (PRYR1; accession no. I46646), bullfrog αRYR (BFr-αRYR; accession no. BAA04646) and fish αRYR (FαRYR; accession no. AAB58117). TαRYR-AS81 (SEQ ID NO:6) shows the 27 amino acid residue deletion of turkey αRYR caused by an 81-bp deletion in the cDNA sequence. TαRYR-AS193 (SEQ ID NO:7) show the amino acid sequence translated from αRYR cDNA sequence with the 193-bp deletion. Deletions in the amino acid sequence are indicated by dots and the dash is added to adjust the alignment. The underlined amino acid residues are the point mutation found in human MH (Jurkat-Rott, et al., 2000). The asterisk indicates a stop codon.

FIG. 4 shows locations and sequences of the alternative splice junctions. The nucleotide and amino acid sequence of turkey αRYR around the splice junctions are shown. The exon sequences are shown in the boxes and the intron sequences are in italics. Tilted lines represent alternative splicing found in this study. The three conserved sequence elements for the splicing acceptor site in exon 13, including the special "a" residue, the polypyrimidine tract (tcct) and the terminal cag at the 3' end of the splicing site are shown in bold.

FIG. 6 shows the nucleic acid (SEQ ID NOS:8 and 21) and amino acid (SEQ ID NOS:22 and 21) sequences of turkey αRYR.

FIG. 7 shows the nucleic acid (SEQ ID NO:17) and amino acid (SEQ ID NO:24) sequences of turkey βRYR.

FIG. 8 shows the nucleic acid and amino acid sequences of the W (SEQ ID NOS: 18 and 25), AS-81 (SEQ ID NOS: 19 and 26) and AS-193 (SEQ ID NOS: 20 and 27) variants.

GENERAL DESCRIPTION OF THE INVENTION

Figure 2:
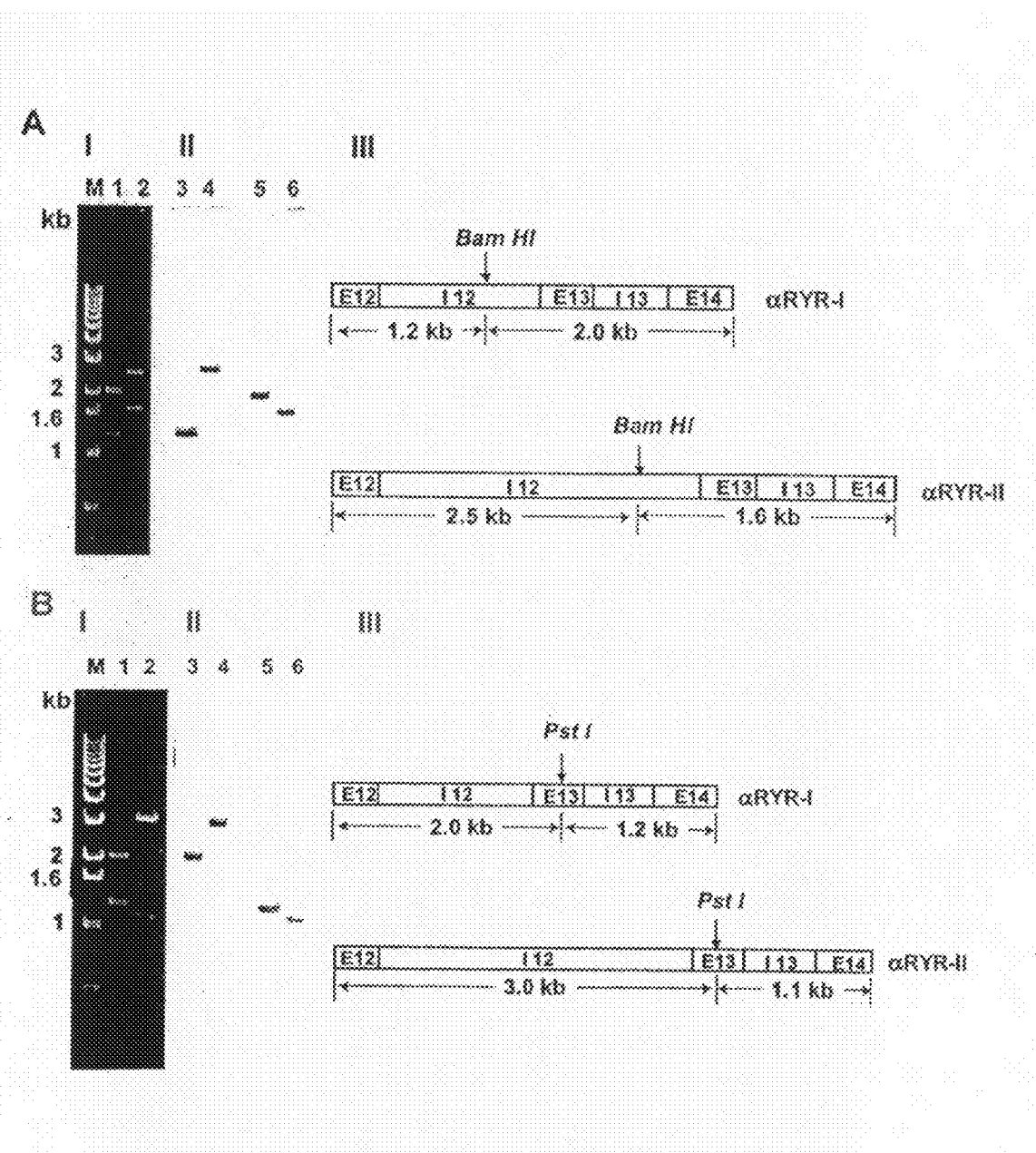
FIG. 2 shows partial restriction endonuclease maps of turkey αRYR alleles derived from restriction digests with Bam HI (A) and PstI (B). 1) the digested fragments of αRYR-I (lane 1) and αRYR-II (lane 2) were analyzed by electrophoresis on a 0.9% agarose gel. II) The digested fragments were transferred to nylon membrane and probed either with E12 (lanes 3 and 4) or E14 probes (lanes 5 and 6) in the Southern Hybrid analysis. Probe E12 carried the last 92 bp of exon 12 and probe E14 carried the last 111 bp of exon 14. III) Partial restriction endonuclease maps of fragments of each allele. M: 1 kb DNA ladder.

The skeletal muscle ryanodine receptor (RYRI), a homotetrameric $Ca^{2+}$ channel protein with a subunit molecular mass of 565 kDa, is localized to the terminal cisternae of the sarcoplasmic reticulum (SR) (Lai, et al., 1988). The large N-terminal domains of each RYR subunit combine to form the "foot" structure which protrudes from the SR and binds to the dihydropyridine receptor (DHPR) embedded in the T-tubule membrane. During skeletal muscle excitation-contraction coupling, depolarization of the sarcolemma/T-tubule membrane system leads to a conformational change in the DHPR which is transmitted to RYR1, causing the channel to open and release $Ca^{2+}$ from the SR (Catterall, 1991).

Malignant hyperthermia (MH) is an inherited autosomal dominant disorder of skeletal muscle $Ca^{2+}$ regulation characterized by hypermetablism and accelerated glycogenolysis resulting in excess heat and lactate production. More that twenty missense mutations and one amino acid deletion in RYRI have been associated with human MH (Jurket-Rott, et al., 2000; Sambuughin, et al., 2001). MH-associated mutations in RYR1 mainly cluster in two regions: mutation hot spot 1 (amino acid residues 35-615) and hot spot 2 (residues 2162-2458). One mutation in human MH, Arg$^{614}$Cys, is homologous with the porcine MH mutation (Fujii, et al., 1991). The major concerns with porcine MH are death from stress and inferior meat quality known as pale, soft, exudative (PSE) meat. PSE meat is characterized by an abnormally light color, a flaccid consistency and poor water holding capacity.

The incidence of MH and PSE meat in the pork industry may have increased as an inadvertent result of genetic selection for muscularity and leanness (Fujii, et al., 1991). Turkey processing industry has reported an increased incidence of PSE turkey meat. The concern has been raised in the growth-selected commercial turkey line (Toelle, et al., 1991). The contemporary turkey breeding industry has, likewise, intensively selected birds for rapid growth and muscularity leading to an increased incidence of meat quality problems including PSE meat. The postmortem biochemical changes which lead to development of PSE turkey are very similar to those observed in PSE pork. These include increased rates of postmortem pH decline, ATP depletion and glycolysis (Pietrzak, et al., 1997). These similarities prompted us to hypothesize that one or more mutations exist in the turkey RYR which alter the rate of postmortem glycolysis and thus account for the observed increase in product quality defects.

In contrast to mammalian skeletal muscle, avian skeletal muscle comprises two RYR isoforms: αRYR (homologous to mammalian RYR1) and βRYR (homologous to mammalian RYR3), which are expressed in approximately equal abundance (Airey, et al., 1993; Ottini, et al., 1996). The presence of numerous mutations in the N-terminal region of human RYR1, together with the existence of the porcine MH mutation in the region prompted us to screen for mutations in the corresponding region of turkey αRYR. Upon cloning and sequencing turkey αRYR cDNA homologous to human RYR1 amino acid residues 376 to 615, we found three different αRYR cDNA transcript variants. One embodiment of the present invention comprises these three novel variants. Additionally, an embodiment of the resent invention comprises two αRYR alleles found by investigating turkey αRYR genomic DNA in the region corresponding to the transcript variants. Yet another embodiment of the present invention comprises characterization of the heterogeneity of turkey αRYR transcript variants, the two αRYR alleles, and the relationship of the expression pattern of the transcript variants to the two alleles. Still yet another embodiment of the present invention comprises a correlation of meat quality and traits with the turkey genotypes.

DETAILED DESCRIPTION OF THE INVENTION

In certain embodiments, the present invention relates to methods to screen for turkeys homozygous for the αRYR-II allele and, therefore, show a higher postmortem muscle pH and better water holding capacity. Embodiments of the present invention also relate to the screening of compounds and methods that, for example, may alter or reduce the occurrence of turkeys displaying symptoms of PSE meat. One such example of a method would be selective breeding of turkeys homozygous for the αRYR-II allele.

I. Turkey RYR Polynucleotides

As described above, variants of the turkey TαRYR peptide have been discovered. Accordingly, the present invention provides nucleic acids encoding these variant turkey TαRYR genes and homologs (e.g., mutations and polymorphisms (e.g., SEQ ID NOs: 6 and 7). In some embodiments, the present invention provide polynucleotide sequences that are capable of hybridizing to nucleotide sequences that encode the peptides SEQ ID NOs: 5, 6 and 7 under conditions of low to high stringency as long as the polynucleotide sequence capable of hybridizing encodes a protein that retains a biological activity of the naturally occurring TαRYR. In some embodiments, the protein that retains a biological activity of naturally occurring TαRYR is 70% homologous to wild-type TαRYR (i.e. SEQ ID NO:5), preferably 80% homologous to wild-type TαRYR, more preferably 90% homologous to wild-type TαRYR, and most preferably 95% homologous to wild-type TαRYR. In preferred embodiments, hybridization conditions are based on the melting temperature ($T_m$) of the nucleic acid binding complex and confer a defined "stringency" as explained above (See e.g., Wahl, et al., Meth. Enzymol., 152:399-407 [1987], incorporated herein by reference).

In other embodiments of the present invention, alleles of TαRYR are provided. In preferred embodiments, alleles result from a polymorphism or mutation, (i.e., a change in the nucleic acid sequence) and generally produce altered mRNAs or polypeptides whose structure or function may or may not be altered. Any given gene may have none, one or many allelic forms. Common mutational changes which give rise to alleles are generally ascribed to deletions, additions or substitutions of nucleic acids. Each of these types of changes may occur alone, or in combination with the others, and at the rate of one or more times in a given sequence. Examples of the alleles of the present invention include TαRYRI and TαRYRII.

In still other embodiments of the present invention, the nucleotide sequences of the present invention may be engineered in order to alter an TαRYR coding sequence for a variety of reasons, including but not limited to, alterations which modify the cloning, processing and/or expression of the gene product. For example, mutations may be introduced using techniques that are well known in the art (e.g., site-directed mutagenesis to insert new restriction sites, to alter glycosylation patterns, to change codon preference, etc.).

In some embodiments of the present invention, the polynucleotide sequence of TαRYR may be extended utilizing the nucleotide sequences by various methods known in the art to detect upstream sequences such as promoters and regulatory elements. For example, it is contemplated that restriction-site polymerase chain reaction (PCR) will find use in the present invention. This is a direct method which uses universal primers to retrieve unknown sequence adjacent to a known locus (Gobinda et al., PCR Methods Applic., 2:318-22 [1993]). First, genomic DNA is amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR can be used to amplify or extend sequences using divergent primers based on a known region (Triglia et al., Nucleic Acids Res., 16:8186 [1988]). The primers may be designed using Oligo 4.0 (National Biosciences Inc, Plymouth Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template. In still other embodiments, walking PCR is utilized. Walking PCR is a method for targeted gene walking that permits retrieval of unknown sequence (Parker et al., Nucleic Acids Res., 19:3055-60 [1991]). The PROMOTERFINDER® kit (Clontech) uses PCR, nested primers and special libraries to "walk in" genomic DNA. This process avoids the need to screen libraries and is useful in finding intron/exon junctions.

Preferred libraries for screening for full length cDNAs include mammalian libraries that have been size-selected to include larger cDNAs. Also, random primed libraries are preferred, in that they will contain more sequences which contain the 5' and upstream gene regions. A randomly primed library may be particularly useful in case where an oligo d(T) library does not yield full-length cDNA. Genomic mammalian libraries are useful for obtaining introns and extending 5' sequence.

In other embodiments of the present invention, variants of the disclosed TαRYR sequences are provided. In preferred embodiments, variants result from polymorphisms or mutations, (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that it is possible to modify the structure of a peptide having a function (e.g., TαRYR function) for such purposes as, for example, increasing binding affinity of the TαRYR for it's substrate. Such modified peptides are considered functional equivalents of peptides having an activity of TαRYR as defined herein. A modified peptide can be produced in which the nucleotide sequence encoding the polypeptide has been altered, such as by substitution, deletion, or addition. In particularly preferred embodiments, these modifications do not significantly reduce the synthetic activity of the modified TαRYR. In other words, construct "X" can be evaluated in order to determine whether it is a member of the genus of modified or variant TαRYR's of the present invention as defined functionally, rather than structurally.

Moreover, as described above, variant forms of TαRYR are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of TαRYR disclosed herein containing conservative replacements.

Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17-21, 2nd ed, WH Freeman and Co., 1981). Whether a change in the amino acid sequence of a peptide results in a functional homolog can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants, described in more detail below. In still other embodiments of the present invention, the nucleotide sequences of the present invention may be engineered in order to alter a TαRYR coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.).

II. Turkey RYR Polypeptides

In other embodiments, the present invention provides Turkey αRYR (TαRYR) polynucleotide sequences that encode TαRYR polypeptide sequences. TαRYR (e.g., SEQ ID NOs: 5, 6 and 7) are described in FIG. 1. Other embodiments of the present invention provide fragments, fusion proteins or functional equivalents of these TαRYR proteins. In still other embodiments of the present invention, nucleic acid sequences corresponding to TαRYR variants, homologs, and mutants may be used to generate recombinant DNA molecules that direct the expression of the TαRYR variants, homologs and mutants in appropriate host cells. In some embodiments of the present invention, the polypeptide may be a naturally purified product, in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

In one embodiment of the present invention, due to the inherent degeneracy of the genetic code, DNA sequences other than the polynucleotide sequences that encode SEQ ID NOS: 5, 6 and 7 which encode substantially the same or a functionally equivalent amino acid sequence, may be used to clone and express TαRYR. In general, such polynucleotide sequences hybridize to the sequences that encode SEQ ID NOS: 5, 6 and 7 under conditions of high to medium stringency as described above. As will be understood by those of skill in the art, it may be advantageous to produce TαRYR-encoding nucleotide sequences possessing non-naturally occurring codons. Therefore, in some preferred embodiments, codons preferred by a particular prokaryotic or eukaryotic host (Murray, et al., Nucl. Acids Res., 17 [1989]) are selected, for example, to increase the rate of Turkey RYR expression or to produce recombinant RNA transcripts having desirable properties, such as a longer half-life, than transcripts produced from naturally occurring sequence.

1. Vectors for Production of Turkey αRYR

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above (e.g., nucleotide sequences that encode SEQ ID NOS: 5, 6 and 7). In some embodiments of the present invention, the constructs comprise a vector, such as a plasmid or viral vector, into which a sequence of the invention has been inserted, in a forward or reverse orientation. In still other embodiments, the heterologous structural sequence (e.g., nucleotide sequences that encode SEQ ID NOS: 5, 6 and 7) is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, pSVL (Pharmacia). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the $E.\ coli$ lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in $E.\ coli$).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

2. Host Cells for Production of Turkey αRYR

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis,* and various species within the genera *Pseudomonas, Streptomyces,* and *Staphylococcus,* as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, [1986]). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

3. Purification of Turkey αRYR

The present invention also provides methods for recovering and purifying Turkey RYR from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein refolding steps can be used as necessary, in completing configuration of the mature protein. In still other embodiments of the present invention, high performance liquid chromatography (HPLC) can be employed for final purification steps.

The present invention further provides polynucleotides having the coding sequence (e.g., polynucleotides encoding the peptide sequences SEQ ID NOs: 5, 6 and 7) fused in frame to a marker sequence which allows for purification of the polypeptide of the present invention. A non-limiting example of a marker sequence is a hexahistidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host (e.g., COS-7 cells) is used. The HA tag corresponds to an epitope derived from the influenza hemagglutinin protein (Wilson et al., Cell, 37:767 [1984]).

4. Truncation Mutants of Turkey αRYR

In addition, the present invention provides fragments of TαRYR (i.e., truncation mutants, e.g., SEQ ID NOS: 6 and 7). In some embodiments of the present invention, when expression of a portion of the Turkey RYR protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat, et al., J. Bacteriol., 169:751-757 [1987]) and *Salmonella typhimurium* and its in vitro activity has been demonstrated on recombinant proteins (Miller et al., Proc. Natl. Acad. Sci. USA 84:2718-1722 [1990]). Therefore, removal of an N-terminal methionine, if desired, can be achieved either in vivo by expressing such recombinant polypeptides in a host which produces MAP (e.g., *E. coli* or CM89 or *S. cerevisiae*), or in vitro by use of purified MAP.

5. Fusion Proteins Containing Turkey αRYR

The present invention also provides fusion proteins incorporating all or part of TαRYR. Accordingly, in some embodiments of the present invention, the coding sequences for the polypeptide can be incorporated as a part of a fusion gene including a nucleotide sequence encoding a different polypeptide. It is contemplated that this type of expression system will find use under conditions where it is desirable to produce an immunogenic fragment of a TαRYR protein. In some embodiments of the present invention, the VP6 capsid protein of rotavirus is used as an immunologic carrier protein for portions of the TαRYR polypeptide, either in the monomeric form or in the form of a viral particle. In other embodiments of the present invention, the nucleic acid sequences corresponding to the portion of TαRYR against which antibodies are to be raised can be incorporated into a fusion gene construct which includes coding sequences for a late vaccinia virus structural protein to produce a set of recombinant viruses expressing fusion proteins comprising a portion of TαRYR as part of the virion. It has been demonstrated with the use of immunogenic fusion proteins utilizing the hepatitis B surface antigen fusion proteins that recombinant hepatitis B virions can be utilized in this role as well. Similarly, in other embodiments of the present invention, chimeric constructs coding for fusion proteins containing a portion of TαRYR and the poliovirus capsid protein are created to enhance immunogenicity of the set of polypeptide antigens (See e.g., EP Publication No. 025949; and Evans, et al., Nature 339:385 [1989]; Huang, et al., J. Virol., 62:3855 [1988]; and Schlienger, et al., J. Virol., 66:2 [1992]).

In still other embodiments of the present invention, the multiple antigen peptide system for peptide-based immunization can be utilized. In this system, a desired portion of TαRYR is obtained directly from organo-chemical synthesis of the peptide onto an oligomeric branching lysine core (see e.g., Posnett, et al., J. Biol. Chem., 263:1719 [1988]; and Nardelli, et al., J. Immunol., 148:914 [1992]). In other embodiments of the present invention, antigenic determinants of the TαRYR proteins can also be expressed and presented by bacterial cells.

In addition to utilizing fusion proteins to enhance immunogenicity, it is widely appreciated that fusion proteins can also facilitate the expression of proteins, such as the TαRYR proteins of the present invention (e.g., SEQ ID NOS: 5, 6 and 7). Accordingly, in some embodiments of the present invention, TαRYR can be generated as a glutathione-S-transferase (i.e., GST fusion protein). It is contemplated that such GST fusion proteins will enable easy purification of TαRYR, such as by the use of glutathione-derivatized matrices (See, e.g., Ausabel et al. (eds.), Current Protocols in Molecular Biology, John Wiley & Sons, NY [1991]). In another embodiment of the present invention, a fusion gene coding for a purification leader sequence, such as a poly-(His)/enterokinase cleavage site sequence at the N-terminus of the desired portion of Turkey RYR, can allow purification of the expressed Turkey RYR fusion protein by affinity chromatography using a $Ni^{2+}$ metal resin. In still another embodiment of the present invention, the purification leader sequence can then be subsequently removed by treatment with enterokinase (See e.g., Hochuli, et al., J. Chromatogr., 411:177 [1987]; and Janknecht, et al., Proc. Natl. Acad. Sci. USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments can be carried out using anchor primers which give rise to complementary overhangs between two consecutive gene fragments which can subsequently be annealed to generate a chimeric gene sequence (See e.g., Current Protocols in Molecular Biology, supra).

6. Variants of Turkey αRYR

Still other embodiments of the present invention provide mutant or variant forms of TαRYR (i.e., muteins). It is possible to modify the structure of a peptide having an activity of TαRYR for such purposes as enhancing therapeutic or prophylactic efficacy, or stability (e.g., ex vivo shelf life, and/or resistance to proteolytic degradation in vivo). Such modified peptides are considered functional equivalents of peptides having an activity of the subject TαRYR proteins as defined herein. A modified peptide can be produced in which the amino acid sequence has been altered, such as by amino acid substitution, deletion, or addition.

Moreover, as described above, variant forms (e.g., mutants or polymorphic sequences) of the subject TαRYR proteins are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present TαRYR proteins, as well as truncation mutants, and is especially useful for identifying potential variant sequences (i.e., mutants or polymorphic sequences). The purpose of screening such combinatorial libraries is to generate, for example, novel TαRYR variants which can act as either agonists or antagonists, or alternatively, possess novel activities all together.

Therefore, in some embodiments of the present invention, TαRYR variants are engineered by the present method to promote, for example, a higher pH in harvested turkey meat. In other embodiments of the present invention, combinatorially-derived homologs are generated which have a selective potency relative to a naturally occurring TαRYR. Such proteins, when expressed from recombinant DNA constructs, can be used, for example, in gene therapy protocols or in the generation of transgenic animals.

Still other embodiments of the present invention provide TαRYR variants which have intracellular half-lives dramatically different than the corresponding wild-type protein. For example, the altered protein can be rendered either more stable or less stable to proteolytic degradation or other cellular process which result in destruction of, or otherwise inactivate, TαRYR. Such variants, and the genes which encode them, can be utilized to alter the location of TαRYR expression by modulating the half-life of the protein. For instance, a short half-life can give rise to more transient TαRYR biological effects and, when part of an inducible expression system, can allow tighter control of TαRYR levels within the cell. As above, such proteins, and particularly their recombinant nucleic acid constructs, can be used in gene therapy protocols.

In still other embodiments of the present invention, TαRYR variants are generated by the combinatorial approach to act as antagonists, in that they are able to interfere with the ability of the corresponding wild-type protein to regulate cell function.

In some embodiments of the combinatorial mutagenesis approach of the present invention, the amino acid sequences for a population of TαRYR variants or other related proteins are aligned, preferably to promote the highest homology possible. Such a population of variants can include, for example, TαRYR homologs from one or more strain or TαRYR variants from the same strain but which differ due to mutation. Amino acids which appear at each position of the aligned sequences are selected to create a degenerate set of combinatorial sequences.

In a preferred embodiment of the present invention, the combinatorial TαRYR library is produced by way of a degenerate library of genes encoding a library of polypeptides which each include at least a portion of potential TαRYR protein sequences. For example, a mixture of synthetic oligonucleotides can be enzymatically ligated into gene sequences such that the degenerate set of potential TαRYR sequences are expressible as individual polypeptides, or alternatively, as a set of larger fusion proteins (e.g., for phage display) containing the set of TαRYR sequences therein.

There are many ways by which the library of potential TαRYR homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential TαRYR sequences. The synthesis of degenerate oligonucleotides is well known in the art (See e.g., Narang, Tetrahedron Lett., 39:3 9 [1983]; Itakura, et al., Recombinant DNA, in Walton (ed.), *Proceedings of the 3rd Cleveland Symposium on Macromolecules*, Elsevier, Amsterdam, pp 273-289 [1981]; Itakura, et al., Annu. Rev. Biochem., 53:323 [1984]; Itakura et al., Science 198:1056 [1984]; Ike, et al., Nucl. Acid Res., 11:477 [1983]). Such techniques have been employed in the directed evolution of other proteins (See e.g., Scott, et al., Science 249:386-390 [1980]; Roberts, et al., Proc. Natl. Acad. Sci. USA 89:2429-2433 [1992]; Devlin, et al., Science 249: 404-406 [1990]; Cwirla, et al., Proc. Natl. Acad. Sci. USA 87: 6378-6382 [1990]; as well as U.S. Pat. Nos. 5,223,409, 5,198,346, and 5,096,815, each of which is incorporated herein by reference).

It is contemplated that the TαRYR nucleic acids (e.g., FIG. 6 and fragments and variants thereof) can be utilized as starting nucleic acids for directed evolution. These techniques can be utilized to develop TαRYR variants having desirable properties such as, for example, promoting increased postmortem muscle pH. Such variants could then be used, e.g., for the generation of transgenic animals In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458-67 [1996]; Leung, et al., Technique, 1:11-15 [1989]; Eckert and Kunkel, PCR Methods Appl., 1:17-24 [1991]; Caldwell and Joyce, PCR Methods Appl., 2:28-33 (1992); and Zhao and Arnold, Nuc. Acids. Res., 25:1307-08 [1997]). After mutagenesis, the resulting clones are selected for desirable activity (e.g., screened for Turkey RYR activity). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith, Nature, 370:324-25 [1994]; U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences.

Multiple cycles of selection and shuffling have led to the functional enhancement of several enzymes (Stemmer, Nature, 370:398-91 [1994]; Stemmer, Proc. Natl. Acad. Sci. USA, 91, 10747-51 [1994]; Crameri, et al., Nat. Biotech., 14:315-19 [1996]; Zhang, et al., Proc. Natl. Acad. Sci. USA, 94:4504-09 [1997]; and Crameri, et al., Nat. Biotech., 15:436-38 [1997]). Variants produced by directed evolution can be screened for TαRYR activity (in vitro) or for the affect on the production of PSE meat (in vivo).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of TαRYR homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

7. Chemical Synthesis of TαRYR

In an alternate embodiment of the invention, the coding sequence of TαRYR is synthesized, whole or in part, using chemical methods well known in the art (See e.g., Caruthers, et al., Nucl. Acids Res. Symp. Ser., 7:215-233 [1980]; Crea and Horn, Nucl. Acids Res., 9:2331 [1980]; Matteucci and Caruthers, Tetrahedron Lett., 21:719 [1980]; and Chow and Kempe, Nucl. Acids Res., 9:2807-2817 [1981]). In other embodiments of the present invention, the protein itself is produced using chemical methods to synthesize either an entire TαRYR amino acid sequence or a portion thereof. For example, peptides can be synthesized by solid phase techniques, cleaved from the resin, and purified by preparative high performance liquid chromatography (See e.g., Creighton, *Proteins Structures And Molecular Principles*, W H Freeman and Co, New York N.Y. [1983]). In other embodiments of the present invention, the composition of the synthetic peptides is confirmed by amino acid analysis or sequencing (See e.g., Creighton, supra).

Direct peptide synthesis can be performed using various solid-phase techniques (Roberge, et al., Science 269:202-204 [1995]) and automated synthesis may be achieved, for example, using ABI 431A Peptide Synthesizer (Perkin Elmer) in accordance with the instructions provided by the manufacturer. Additionally, the amino acid sequence of TαRYR, or any part thereof, may be altered during direct synthesis and/or combined using chemical methods with other sequences to produce a variant polypeptide.

III. Detection of TαRYR Alleles

In some embodiments, the present invention includes alleles of TαRYR that, when expressed homozygously, descrease symptoms of PSE meat (e.g., including, but not limited to, nucleotide sequences that encode SEQ ID NOs: 5, 6 and 7). Analysis of naturally occurring turkey TαRYR alleles revealed that turkeys with decreased susceptibility for the production of meat having symptoms of PSE meat are homozygous for TαRYRII.

The present invention is not limited to a particular mechanism of action. Indeed, an understanding of the mechanism of action is not necessary to practice the present invention. Nevertheless, it is contemplated that turkeys homozygous for TαRYRII have altered transport of metabolites from the sarcoplasmic reticulum that alter, for example, postmortem muscle pH.

Accordingly, in one embodiment, the present invention provides methods for determining whether a turkey has decreased susceptablility for the production of meat having higher postmortem pH and better water holding capacity by determining whether the turkey is homozygous for the TαRYRII allele.

A number of methods are available for analysis of variant (e.g., mutant or polymorphic) nucleic acid sequences and presence of particular alleles of a gene. Assays for detections variants and alleles (e.g., polymorphisms or mutations) fall into several categories, including, but not limited to direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following assays are useful in the present invention.

1. Direct Sequencing Assays

In some embodiments of the present invention, variant sequences are detected using a direct sequencing technique. In these assays, DNA samples are first isolated from a subject using any suitable method. In some embodiments, the region of interest is cloned into a suitable vector and amplified by growth in a host cell (e.g., a bacteria). In other embodiments, DNA in the region of interest is amplified using PCR.

Following amplification, DNA in the region of interest (e.g., the region containing the SNP or mutation of interest) is sequenced using any suitable method, including but not limited to manual sequencing using radioactive marker nucleotides, or automated sequencing. The results of the sequencing are displayed using any suitable method. The sequence is examined and the presence or absence of a given SNP or mutation is determined.

2. PCR Assay

In some embodiments of the present invention, variant sequences are detected using a PCR-based assay. In some embodiments, the PCR assay comprises the use of oligonucleotide primers that hybridize only to the variant or wild type allele of TαRYR (e.g., to the region of polymorphism or mutation). Both sets of primers are used to amplify a sample of DNA. If only the mutant primers result in a PCR product, then the patient has the mutant TαRYR allele or an allelic homolog. For example, if only the TαRYRII primers result in a PCR product, then the turkey is homozygous for the TαRYRII allele.

3. Fragment Length Polymorphism Assays

In some embodiments of the present invention, variant sequences and alleles are detected using a fragment length polymorphism assay. In a fragment length polymorphism assay, a unique DNA banding pattern based on cleaving the DNA at a series of positions is generated using an enzyme (e.g., a restriction enzyme or a CLEAVASE I [Third Wave Technologies, Madison, Wis.] enzyme). DNA fragments from a sample containing a SNP or a mutation will have a different banding pattern than wild type.

a. RFLP Assay

In some embodiments of the present invention, variant sequences or alleles are detected using a restriction fragment length polymorphism assay (RFLP). The region of interest is first isolated using PCR. The PCR products are then cleaved with restriction enzymes known to give a unique length fragment for a given polymorphism. The restriction-enzyme digested PCR products are separated by agarose gel electrophoresis and visualized by ethidium bromide staining. The length of the fragments is compared to molecular weight markers and fragments generated from wild-type and mutant controls.

b. CFLP Assay

In other embodiments, variant sequences are detected using a CLEAVASE fragment length polymorphism assay (CFLP; Third Wave Technologies, Madison, Wis.; See e.g., U.S. Pat. Nos. 5,843,654; 5,843,669; 5,719,208; and 5,888,780; each of which is herein incorporated by reference). This assay is based on the observation that when single strands of DNA fold on themselves, they assume higher order structures that are highly individual to the precise sequence of the DNA molecule. These secondary structures involve partially duplexed regions of DNA such that single stranded regions are juxtaposed with double stranded DNA hairpins. The CLEAVASE I enzyme, is a structure-specific, thermostable nuclease that recognizes and cleaves the junctions between these single-stranded and double-stranded regions.

The region of interest is first isolated, for example, using PCR. Then, DNA strands are separated by heating. Next, the reactions are cooled to allow intrastrand secondary structure to form. The PCR products are then treated with the CLEAVASE I enzyme to generate a series of fragments that are unique to a given SNP or mutation. The CLEAVASE enzyme treated PCR products are separated and detected (e.g., by agarose gel electrophoresis) and visualized (e.g., by ethidium bromide staining). The length of the fragments is compared to molecular weight markers and fragments generated from allelic controls.

4. Hybridization Assays

In preferred embodiments of the present invention, variant sequences are detected a hybridization assay. In a hybridization assay, the presence of absence of a given SNP or mutation is determined based on the ability of the DNA from the sample to hybridize to a complementary DNA molecule (e.g., a oligonucleotide probe). A variety of hybridization assays using a variety of technologies for hybridization and detection are available. A description of a selection of assays is provided below.

a. Direct Detection of Hybridization

In some embodiments, hybridization of a probe to the sequence of interest (e.g., a SNP or mutation) is detected directly by visualizing a bound probe (e.g., a Northern or Southern assay; See e.g., Ausabel et al. (eds.), Current Protocols in Molecular Biology, John Wiley & Sons, NY [1991]). In a these assays, genomic DNA (Southern) or RNA (Northern) is isolated from a subject. The DNA or RNA is then cleaved with a series of restriction enzymes that cleave infrequently in the genome and not near any of the markers being assayed. The DNA or RNA is then separated (e.g., on an agarose gel) and transferred to a membrane. A labelled (e.g., by incorporating a radionucleotide) probe or probes specific for the SNP or mutation being detected is allowed to contact the membrane under a condition or low, medium, or high stringency conditions. Unbound probe is removed and the presence of binding is detected by visualizing the labelled probe.

b. Detection of Hybridization Using "DNA Chip" Assays

In some embodiments of the present invention, variant sequences are detected using a DNA chip hybridization assay. In this assay, a series of oligonucleotide probes are affixed to a solid support. The oligonucleotide probes are designed to be unique to a given SNP or mutation. The DNA sample of interest is contacted with the DNA "chip" and hybridization is detected.

In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

The nucleic acid to be analyzed is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (Nanogen, San Diego, Calif.) is utilized (See e.g., U.S. Pat. Nos. 6,017,696; 6,068,818; and 6,051,380; each of which are herein incorporated by reference). Through the use of microelectronics, Nanogen's technology enables the active movement and concentration of charged molecules to and from designated test sites on its semiconductor microchip. DNA capture probes unique to a given SNP or mutation are electronically placed at, or "addressed" to, specific sites on the microchip. Since DNA has a strong negative charge, it can be electronically moved to an area of positive charge.

First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample is then analyzed for the presence of target DNA molecules by determining which of the DNA capture probes hybridize, with complementary DNA in the test sample (e.g., a PCR amplified gene of interest). An electronic charge is also used to move and concentrate target molecules to one or more test sites on the microchip. The electronic concentration of sample DNA at each test site promotes rapid hybridization of sample DNA with complementary capture probes (hybridization may occur in minutes). To remove any unbound or nonspecifically bound DNA from each site, the polarity or charge of the site is reversed to negative, thereby forcing any unbound or nonspecifically bound DNA back into solution away from the capture probes. A laser-based fluorescence scanner is used to detect binding, In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and then removing them by spinning.

DNA probes unique for the SNP or mutation of interest are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given SNP or mutation. Batches of beads are combined to form a pool specific to the array. To perform an assay, the BEAD ARRAY is contacted with a prepared subject sample (e.g., DNA). Hybridization is detected using any suitable method.

c. Enzymatic Detection of Hybridization

In some embodiments of the present invention, genomic profiles are generated using a assay that detects hybridization by enzymatic cleavage of specific structures (INVADER assay, Third Wave Technologies; See e.g., U.S. Pat. Nos. 5,846,717; 6,090,543; 6,001,567; 5,985,557; and 5,994,069; each of which is herein incorporated by reference). The INVADER assay detects specific DNA and RNA sequences by using structure-specific enzymes to cleave a complex formed by the hybridization of overlapping oligonucleotide probes. Elevated temperature and an excess of one of the probes enable multiple probes to be cleaved for each target sequence present without temperature cycling. These cleaved probes then direct cleavage of a second labeled probe. The secondary probe oligonucleotide can be 5'-end labeled with fluorescein that is quenched by an internal dye. Upon cleavage, the de-quenched fluorescein labeled product may be detected using a standard fluorescence plate reader.

The INVADER assay detects specific mutations and SNPs in unamplified genomic DNA. The isolated DNA sample is contacted with the first probe specific either for a SNP/mutation or wild type sequence and allowed to hybridize. Then a secondary probe, specific to the first probe, and containing the fluorescein label, is hybridized and the enzyme is added. Binding is detected by using a fluorescent plate reader and comparing the signal of the test sample to known positive and negative controls.

In some embodiments, hybridization of a bound probe is detected using a TaqMan assay (PE Biosystems, Foster City, Calif; See e.g., U.S. Pat. Nos. 5,962,233 and 5,538,848, each of which is herein incorporated by reference). The assay is performed during a PCR reaction. The TaqMan assay exploits the 5'-3' exonuclease activity of the AMPLITAQ GOLD DNA polymerase. A probe, specific for a given allele or mutation, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In still further embodiments, polymorphisms are detected using the SNP-IT primer extension assay (Orchid Biosciences, Princeton, N.J.; See e.g., U.S. Pat. Nos. 5,952,174 and 5,919,626, each of which is herein incorporated by reference). In this assay, SNPs are identified by using a specially synthesized DNA primer and a DNA polymerase to selectively extend the DNA chain by one base at the suspected SNP location. DNA in the region of interest is amplified and denatured. Polymerase reactions are then performed using miniaturized systems called microfluidics. Detection is accomplished by adding a label to the nucleotide suspected of being at the SNP or mutation location. Incorporation of the label into the DNA can be detected by any suitable method (e.g., if the nucleotide contains a biotin label, detection is via a fluorescently labelled antibody specific for biotin).

5. Mass Spectroscopy Assay

In some embodiments, a MassARRAY system (Sequenom, San Diego, Calif.) is used to detect variant sequences (See e.g., U.S. Pat. Nos. 6,043,031; 5,777,324; and 5,605,798; each of which is herein incorporated by reference). DNA is isolated from blood samples using standard procedures. Next, specific DNA regions containing the mutation or SNP of interest, about 200 base pairs in length, are amplified by PCR. The amplified fragments are then attached by one strand to a solid surface and the non-immobilized strands are removed by standard denaturation and washing. The remaining immobilized single strand then serves as a template for automated enzymatic reactions that produce genotype specific diagnostic products.

Very small quantities of the enzymatic products, typically five to ten nanoliters, are then transferred to a SpectroCHIP array for subsequent automated analysis with the SpectroREADER mass spectrometer. Each spot is preloaded with light absorbing crystals that form a matrix with the dispensed diagnostic product. The MassARRAY system uses MALDI-TOF (Matrix Assisted Laser Desorption Ionization—Time of Flight) mass spectrometry. In a process known as desorption, the matrix is hit with a pulse from a laser beam. Energy from the laser beam is transferred to the matrix and it is vaporized resulting in a small amount of the diagnostic product being expelled into a flight tube. As the diagnostic product is charged when an electrical field pulse is subsequently applied to the tube they are launched down the flight tube towards a detector. The time between application of the electrical field pulse and collision of the diagnostic product with the detector is referred to as the time of flight. This is a very precise measure of the product's molecular weight, as a molecule's mass correlates directly with time of flight with smaller molecules flying faster than larger molecules. The entire assay is completed in less than one thousandth of a second, enabling samples to be analyzed in a total of 3-5 second including repetitive data collection. The SpectroTYPER software then calculates, records, compares and reports the genotypes at the rate of three seconds per sample.

6. Variant Analysis by Differential Antibody Binding

In other embodiments of the present invention, antibodies (See below for antibody production) are used to determine if an individual contains an allele encoding a variant Turkey RYR gene. In preferred embodiments, antibodies are utilized that discriminate between mutant (i.e., truncated proteins; e.g., SEQ ID NOS: 6 and 7); and wild-type proteins (SEQ ID NO: 5). In some particularly preferred embodiments, the antibodies are directed to the C-terminus of TαRYR.

7. Kits for Analyzing Risk of PSE Meat

The present invention also provides kits for determining whether an individual animal contains a wild-type or variant (e.g., polymorphic or mutant) allele of Turkey RYR. In some embodiments, the kits are useful determining whether the subject is at risk of developing PSE meat. The diagnostic kits are produced in a variety of ways. In some embodiments, the kits contain at least one reagent for specifically detecting a mutant Turkey RYR allele or protein. In preferred embodiments, the kits contains reagents for detecting if the turkey is homozygous for the TαRYRII allele. In preferred embodiments, the reagent is a nucleic acid that hybridizes to nucleic acids containing the SNP and that does not bind to nucleic acids that do not contain the SNP. In other preferred embodiments, the reagents are primers for amplifying the region of DNA containing the SNP. In still other embodiments, the reagents are antibodies which preferentially bind either the wild-type or truncated TαRYR proteins. In some embodiments, the kit contains instructions for determining whether the subject is susceptible to producing PSE meat. In preferred embodiments, the instructions specify that risk for developing Crohn's disease is determined by detecting the presence of alleles homozygous for TαRYRII. In some embodiments, the kits include ancillary reagents such as buffering agents, nucleic acid stabilizing reagents, protein stabilizing reagents, and signal producing systems (e.g., florescence generating systems as Fret systems). The test kit may be packages in any suitable manner, typically with the elements in a single container or various containers as necessary along with a sheet of instructions for carrying out the test in some embodiments, the kits also preferably include a positive control sample.

IV. Generation of Turkey RYR Antibodies

Antibodies can be generated to allow for the detection of Turkey RYR protein. The antibodies may be prepared using various immunogens. In one embodiment, the immunogen is a TαRYR peptide to generate antibodies that recognize TαRYR. Such antibodies include, but are not limited to polyclonal, monoclonal, chimeric, single chain, Fab fragments, and Fab expression libraries.

Various procedures known in the art may be used for the production of polyclonal antibodies directed against TαRYR. For the production of antibody, various host animals can be immunized by injection with the peptide corresponding to the TαRYR epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward TαRYR, it is contemplated that any technique that provides for the production of antibody molecules by continuous cell lines in culture will find use with the present invention (See e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein, Nature 256:495-497 [1975]), as well as the trioma technique, the human B-cell hybridoma technique (See, e.g., Kozbor, et al., Immunol. Tod., 4:72 [1983]), and the EBV-hybridoma technique to produce human monoclonal antibodies (Cole, et al., in *Monoclonal Antibodies and Cancer Therapy*, Alan R. Liss, Inc., pp. 77-96 [1985]).

In an additional embodiment of the invention, monoclonal antibodies are produced in germ-free animals utilizing technology such as that described in PCT/US90/02545). Furthermore, it is contemplated that human antibodies will be generated by human hybridomas (Cote et al., Proc. Natl. Acad. Sci. USA 80:2026-2030 [1983]) or by transforming human B cells with EBV virus in vitro (Cole et al., in *Monoclonal Antibodies and Cancer Therapy*, Alan R. Liss, pp. 77-96 [1985]).

In addition, it is contemplated that techniques described for the production of single chain antibodies (U.S. Pat. No. 4,946,778; herein incorporated by reference) will find use in producing Turkey RYR specific single chain antibodies. An additional embodiment of the invention utilizes the techniques described for the construction of Fab expression libraries (Huse, et al., Science 246:1275-1281 [1989]) to allow rapid and easy identification of monoclonal Fab fragments with the desired specificity for TαRYR.

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g.,gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. (As is well known in the art, the immunogenic peptide should be provided free of the carrier molecule used in any immunization protocol. For example, if the peptide was conjugated to KLH, it may be conjugated to BSA, or used directly, in a screening assay.)

The foregoing antibodies can be used in methods known in the art relating to the localization and structure of Turkey RYR (e.g., for Western blotting), measuring levels thereof in appropriate biological samples, etc. The antibodies can be used to detect TαRYR in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of TαRYR using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of TαRYR detected by immunoblotting (Western blotting). Immunoblotting techniques are generally more effective with antibodies generated against a peptide corresponding to an epitope of a protein, and hence, are particularly suited to the present invention.

Another method uses antibodies as agents to alter signal transduction. Specific antibodies that bind to the binding domains of TαRYR or other proteins involved in intracellular signalling can be used to inhibit the interaction between the various proteins and their interaction with other ligands. Antibodies that bind to the complex can also be used therapeutically to inhibit interactions of the protein complex in the signal transduction pathways leading to the various physiological and cellular effects of TαRYR ion transport. Such antibodies can also be used diagnostically to measure abnormal expression of TαRYR, or the aberrant formation of protein complexes, which may be indicative of a disease state.

V. Gene Therapy Using TαRYR

The present invention also provides methods and compositions suitable for gene therapy to alter TαRYR expression, production, or function. As described above, the present invention provides TαRYR genes and provides methods of obtaining RYR genes from other species. Thus, the methods described below are generally applicable across many species. In some embodiments, it is contemplated that the gene therapy is performed by providing a subject with a wild-type allele of TαRYRI (i.e., the allele associated with non-PSE meat). Subjects in need of such therapy are identified by the methods described above. As described above, TαRYR is (primarily) expressed in the muscle cells. Accordingly, subjects could be treated after birth or, in a preferred embodiment, subjects are the product of transgenic engineering wherein the desired gene is incorporated into the genome of the subject before fertilization of the oocyte (see, section VI, below).

Viral vectors commonly used for in vivo or ex vivo targeting and therapy procedures are DNA-based vectors and retroviral vectors. Methods for constructing and using viral vectors are known in the art (See, e.g., Miller and Rosman, BioTech., 7:980-990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt, et al., Mol. Cell. Neurosci., 2:320-330 [1991]), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet, et al. (J. Clin. Invest., 90:626-630 [1992]; See also, La Salle et al., Science 259:988-990 [1993]); and a defective adeno-associated virus vector (Samulski et al., J. Virol., 61:3096-3101 [1987]; Samulski, et al., J. Virol., 63:3822-3828 [1989]; and Lebkowski, et al., Mol. Cell. Biol., 8:3988-3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-β), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See e.g., WO94/26914). Those adenoviruses of animal origin that can be used within the scope of the present invention include adenoviruses of canine, bovine, murine (e.g., Mav1, Beard, et al., Virol., 75-81 [1990]), ovine, porcine, avian, and simian (e.g., SAV) origin. Preferably, the adenovirus of animal origin is a canine adenovirus, more preferably a CAV2 adenovirus (e.g., Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO95/02697), the E2 region (e.g., WO94/28938), the E4 region (e.g., W094/28152, WO94/12649 and WO95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and W096/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917 [1984]). In particular, they can be prepared by homologous recombination between an adenovirus and a plasmid which carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J. Gen. Virol., 36:59 [1977]), which contains the left-hand portion of the genome of an Ad5 adenovirus (12%) integrated into its genome, and cell lines that are able to complement the E1 and E4 functions, as described in applications WO94/26914 and WO95/02697. Recombinant adenoviruses are recovered and purified using standard molecular biological techniques, that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. No. 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399,346, 4,650,764, 4,980,289 and 5,124,263; all of which are herein incorporated by reference; Mann et al., Cell 33:153 [1983]; Markowitz, et al., J. Virol., 62:1120 [1988]; PCT/US95/14575; EP 453242; EP178220; Bernstein, et al. Genet. Eng., 7:235 [1985]; McCormick, BioTechnol., 3:689 [1985]; WO 95/07358; and Kuo, et al., Blood 82:845 [1993]). The retroviruses are integrating viruses that infect dividing cells. The retrovirus genome includes two LTRs, an encapsidation sequence and three coding regions (gag, pol and env). In recombinant. retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Feigner, et. al., Proc. Natl. Acad. Sci. USA 84:7413-7417 [1987]; See also, Mackey, et al., Proc. Natl. Acad. Sci. USA 85:8027-8031 [1988]; Ulmer, et al., Science 259:1745-1748 [1993]). The use of cationic lipids may promote encapsulation of negatively charged nucleic acids, and also promote fusion with negatively charged cell membranes (Feigner, and Ringold, Science 337:387-388 [1989]). Particularly useful lipid compounds and compositions for transfer of nucleic acids are described in WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963-967 [1992]; Wu and Wu, J. Biol. Chem., 263:14621-14624 [1988]; and Williams et al., Proc. Natl. Acad. Sci. USA 88:2726-2730 [1991]). Receptor-mediated DNA delivery approaches can also be used (Curiel, et al., Hum. Gene Ther., 3:147-154 [1992]; and Wu and Wu, J. Biol. Chem., 262:4429-4432 [1987]).

VI. Transgenic Animals Expressing Exogenous TαRYR Genes and Alleles, Homologs, Mutants, and Variants Thereof The present invention contemplates the generation of transgenic animals comprising an exogenous TαRYR gene or alleles, homologs, mutants, or variants thereof. In preferred embodiments, the transgenic animal displays an altered phenotype as compared to PSE susceptable animals (for example, meat having higher postmortem pH and better water holding capacity). In some embodiments, the altered phenotype is the overexpression of mRNA for a TαRYRI gene as compared to levels of TαRYRII expression. In other embodiments, the altered phenotype is the decreased expression of mRNA for an endogenous TαRYRII gene as compared to TαRYRI. Methods for analyzing the presence or absence of such phenotypes include Northern blotting, mRNA protection assays, and RT-PCR as well as examination of postmortem meat. In other embodiments, the transgenic animals have a knock out mutation of the TαRYRII allele.

The transgenic animals of the present invention find use in dietary and drug screens. In some embodiments, the transgenic animals (e.g., animals displaying PSE-meat phenotype) are treated with drugs or diets and the production of PSE-meat is evaluated. In other embodiments, test compounds (e.g., a drug that is suspected of being useful to decrease of eliminate the production of PSE-meat) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter which allows reproducible injection of 1-2 picoliters (pl) of DNA solution. The use of zygotes as a target for gene transfer has a major advantage in that in most cases the injected DNA will be incorporated into the host genome before the first cleavage (Brinster, et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260-1264 [1976]). Efficient infection of the blastomeres is obtained by enzymatic treatment to remove the zona pellucida (Hogan et al., in *Manipulating the Mouse Embryo,* Cold Spring Harbor Laboratory Press, Cold Spring Harbor, N.Y. [1986]). The viral vector system used to introduce the transgene is typically a replication-defective retrovirus carrying the transgene (D. Jahner, et al., Proc. Natl. Acad Sci. USA 82:6927-693 [1985]). Transfection is easily and efficiently obtained by culturing the blastomeres on a monolayer of virus-producing cells (Van der Putten, supra; Stewart, et al., EMBO J., 6:383-388 [1987]). Alternatively, infection can be performed at a later stage. Virus or virus-producing cells can be injected into the blastocoele (D. Jahner, et al., Nature 298:623-628 [1982]). Most of the founders will be mosaic for the transgene since incorporation occurs only in a subset of cells which form the transgenic animal. Further, the founder may contain various retroviral insertions of the transgene at different positions in the genome which generally will segregate in the offspring. In addition, it is also possible to introduce transgenes into the germline, albeit with low efficiency, by intrauterine retroviral infection of the midgestation embryo (Jahner, et al., supra [1982]). Additional means of using retroviruses or retroviral vectors to create transgenic animals known to the art involves the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans, et al., Nature 292:154-156 [1981]; Bradley, et al., Nature 309:255-258 [1984]; Gossler, et al., Proc. Acad. Sci. USA 83:9065-9069 [1986]; and Robertson, et al., Nature 322:445-448 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468-1474 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells which have integrated the transgene. This technique obviates the need for growth of the transfected ES cells under appropriate selective conditions prior to transfer into the blastocoel.

In still other embodiments, homologous recombination is utilized knock-out gene function or create deletion mutants (e.g., mutants in which the LRRs of TαRYR are deleted). Methods for homologous recombination are described in U.S. Pat. No. 5,614,396, incorporated herein by reference.

VII. Drug Screening Using TαRYR

The present invention provides methods and compositions for using TαRYR as a target for screening drugs that can alter, for example, the pH of post-mortem muscle.

The present invention is not limited to any particular mechanism of action. Indeed, an understanding of the mechanism of action is not necessary to practice the present invention. Nevertheless, it is contemplated that the TαRYR protein is a homotetrameric $Ca^{2+}$ channel protein localized to the sarcoplasmic reticulum (SR) (Lai, et al., 1988). The large N-terminal domains of each RYR subunit combine to form the "foot" structure which protrudes from the SR and binds to the DHPR embedded in the T-tubule membrane. During skeletal muscle excitation-contraction coupling, depolarization of the sarcolemma/T-tubule membrane system leads to a conformational change in the DHPR which is transmitted to RYR, causing the channel to open and release $Ca^{2+}$ from the SR (Catterall, 1991).

In one screening method, the two-hybrid system is used to screen for compounds (e.g., drug) capable of altering (e.g., inhibiting) TαRYR function(s) (e.g., membrane channel function) in vitro or in vivo. In one embodiment, a GAL4 binding site, linked to a reporter gene such as lacZ, is contacted in the presence and absence of a candidate compound with a GAL4 binding domain linked to a TαRYR fragment and a GAL4 transactivation domain II linked to a dihydropyridine receptor (DHPR) fragment. Expression of the reporter gene is monitored and a decrease in the expression is an indication that the candidate compound inhibits the interaction of TαRYR with DHPR. Alternately, the effect of candidate compounds on the interaction of TαRYR with other proteins (e.g., proteins known to interact directly or indirectly with DHPR) can be tested in a similar manner.

In another screening method, candidate compounds are evaluated for their ability to alter TαRYR signalling by contacting TαRYR, DHPR, DHPR-associated proteins, or fragments thereof, with the candidate compound and determining binding of the candidate compound to the peptide. The protein or protein fragments is/are immobilized using methods known in the art such as binding a GST-TαRYR fusion protein to a polymeric bead containing glutathione. A chimeric gene encoding a GST fusion protein is constructed by fusing DNA encoding the polypeptide or polypeptide fragment of interest to the DNA encoding the carboxyl terminus of GST (See e.g., Smith et al., Gene 67:31 [1988]). The fusion construct is then transformed into a suitable expression system (e.g., E. coli XA90) in which the expression of the GST fusion protein can be induced with isopropyl-beta-D-thiogalactopyranoside (IPTG). Induction with IPTG should yield the fusion protein as a major constituent of soluble, cellular proteins. The fusion proteins can be purified by methods known to those skilled in the art, including purification by glutathione affinity chromatography. Binding of the candidate compound to the proteins or protein fragments is correlated with the ability of the compound to disrupt the signal transduction pathway and thus regulate TαRYR physiological effects (e.g., $Ca^{2+}$ flux of the sarcoplasmic reticulum).

In another screening method, one of the components of the TαRYR/DHPR signalling system, such as TαRYR or a fragment of TαRYR, is immobilized. Polypeptides can be immobilized using methods known in the art, such as adsorption onto a plastic microtiter plate or specific binding of a GST-fusion protein to a polymeric bead containing glutathione. For example, GST-TαRYR is bound to glutathione-Sepharose beads. The immobilized peptide is then contacted with another peptide with which it is capable of binding in the presence and absence of a candidate compound. Unbound peptide is then removed and the complex solubilized and analyzed to determine the amount of bound labeled peptide. A decrease in binding is an indication that the candidate compound inhibits the interaction of TαRYR with the other peptide. A variation of this method allows for the screening of compounds that are capable of disrupting a previously-formed protein/protein complex. For example, in some embodiments a complex comprising TαRYR or a TαRYR fragment bound to another peptide is immobilized as described above and contacted with a candidate compound. The dissolution of the complex by the candidate compound correlates with the ability of the compound to disrupt or inhibit the interaction between TαRYR and the other peptide.

Another technique for drug screening provides high throughput screening for compounds having suitable binding affinity to TαRYR peptides and is described in detail in WO 84/03564, incorporated herein by reference. Briefly, large numbers of different small peptide test compounds are synthesized on a solid substrate, such as plastic pins or some other surface. The peptide test compounds are then reacted with TαRYR peptides and washed. Bound TαRYR peptides are then detected by methods well known in the art.

Another technique uses TαRYR antibodies, generated as discussed above. Such antibodies capable of specifically binding to TαRYR peptides compete with a test compound for binding to TαRYR. In this manner, the antibodies can be used to detect the presence of any peptide that shares one or more antigenic determinants of the TαRYR peptide.

In some embodiments of the present invention, compounds are screened for their ability to inhibit the binding of pathogen components (e.g., including, but not limited to, bacterial cell surface proteins; fungi proteins, parasite proteins, and virus proteins) to TαRYR. Any suitable screening assay may be utilized, including, but not limited to, those described herein.

The present invention contemplates many other means of screening compounds. The examples provided above are presented merely to illustrate a range of techniques available. One of ordinary skill in the art will appreciate that many other screening methods can be used.

In particular, the present invention contemplates the use of cell lines transfected with TαRYR and variants or mutants thereof for screening compounds for activity, and in particular to high throughput screening of compounds from combinatorial libraries (e.g., libraries containing greater than $10^4$ compounds). The cell lines of the present invention can be used in a variety of screening methods. In some embodiments, the cells can be used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, the host cells are preferably transfected as described above with vectors encoding TαRYR or variants or mutants thereof. The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, $IP_3$, cAMP, arachidonic acid release) due to stimulation of membrane receptors and ion channels (e.g., ligand gated ion channels; see Denyer, et al., Drug Discov. Today 3:323-32 [1998]; and Gonzales, et al., Drug. Discov. Today 4:431-39 [1999]). Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the host cells are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75-80 [1996]), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The cells are also useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product. As described above, it is contemplated that TαRYR binds to DHRP, and this binding results in the conformational change in TαRYR. Therefore, in some embodiments, the reporter gene construct comprises the 5' regulatory region (e.g., promoters and/or enhancers) of a protein whose expression is controlled by DHRP in operable association with a reporter gene (see, Inohara, et al., J. Biol. Chem. 275:27823-31 [2000] for a description of the luciferase reporter construct pBVIx-Luc). Examples of reporter genes finding use in the present invention include, but are not limited to, chloramphenicol transferase, alkaline phosphatase, firefly and bacterial luciferases, beta-galactosidase, beta-lactamase, and green fluorescent protein. The production of these proteins, with the exception of green fluorescent protein, is detected through the use of chemiluminescent, colorimetric, or bioluminescent products of specific substrates (e.g., X-gal and luciferin). Comparisons between compounds of known and unknown activities may be conducted as described above.

VIII. Pharmaceutical Compositions Containing TαRYR Nucleic Acid, Peptides, and Analogs The present invention further provides pharmaceutical compositions which may comprise all or portions of TαRYR polynucleotide sequences, TαRYR polypeptides, inhibitors or antagonists of TαRYR bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

Peptides can be administered to the subject intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one subject depends upon many factors, including the subject's size, body surface area, age, the particular compound to be administered, sex, time and route of administration, general health, and interaction with other drugs being concurrently administered.

Accordingly, in some embodiments of the present invention, Turkey RYR nucleotide and Turkey RYR amino acid sequences can be administered to an animal alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, Turkey RYR polynucleotide sequences or Turkey RYR amino acid sequences may be administered alone to individuals subject to or suffering from a disease.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a subject to be treated.

Pharmaceutical compositions suitable for use in the present invention include compositions wherein the active ingredients are contained in an effective amount to achieve the intended purpose. For example, an effective amount of Turkey RYR may be that amount that suppresses the production of PSE meat. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations which can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For polynucleotide or amino acid sequences of Turkey RYR, conditions indicated on the label may include treatment of condition related to the production of PSE meat.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts lessens the production of PSE meat.

A therapeutically effective dose refers to that amount of Turkey RYR which ameliorates symptoms of the disease state (i.e., the production of PSE meat). Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds which exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the subject, and the route of administration.

The exact dosage is chosen by the individual physician in view of the subject to be treated. Dosage and administration are adjusted to provide sufficient levels of the active moiety or to maintain the desired effect. Additional factors which may be taken into account include the severity of the disease state; age, weight, and gender of the subject; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference). Those skilled in the art will employ different formulations for TαRYR than for the inhibitors of TαRYR. Administration to the bone marrow may necessitate delivery in a manner different from intravenous injections.

EXPERIMENTAL

The following examples serve to illustrate certain preferred embodiments and aspects of the present invention and are not to be construed as limiting the scope thereof.

In the disclosure which follows, the following abbreviations apply: ° C. (degrees Centigrade); vol (volume); w/v (weight to volume); v/v (volume to volume); µl (microliters); ml (milliliters); µg (micrograms); mg (milligrams); M (molar); mM (milliMolar); µM (microMolar); nm (nanometers); kdal (kilodaltons); SDS (sodium dodecyl sulfate); $NaPO_4$ (sodium phosphate); Tris (tris(hydroxymethyl)-aminomethane); PMSF (phenylmethylsulfonylfluoride); TBE (Tris-Borate-EDTA, e.g., Tris buffer titrated with boric acid rather than HCl and containing EDTA); PBS (phosphate buffered saline); PAGE (polyacrylamide gel electrophoresis); Tween (polyoxyethylene-sorbitan); Hybrid, Inc. (Kitchener, ON); Invitrogen (Carlsbad, Calif.); Clontech (Palo Alto, Calif.); MRC (Cincinnati, Ohio); Roche (Indianapolis, Ind.); Promega (Madison, Wis.); Epicenter (Madison, Wis.); New England Biolabs (Beverly, Mass.); Scleicher & Schuell (Keene, N.H.); Sigma (Saint Louis, Mo.).

Materials and Methods

Turkey Breast Muscle Sampling and Breast Meat Quality Evaluation. Genetically unimproved random-bred control (RBC1) turkeys (McCartney, 1964) were obtained from Dr. K. Nestor (Ohio Agricultural Research and Development Center, Wooster, Ohio). The growth-selected turkeys were obtained from Hybrid, Inc. (Kitchener, ON). Both turkey lines were simultaneously raised from 1 day-old hatchlings to market weight (average weights were 22.8 lbs. for RBC1 turkey line and 30.4 lbs. for the growth-selected turkey line) at the MSU poultry farm. Turkeys were slaughtered according to industry practices. The pectoralis major muscle from one side was collected within 5 minutes of death and was immediately sectioned, snap frozen in liquid nitrogen and stored at −80° C. for total RNA and genomic DNA extraction. The pectoralis major muscle from the remaining side was used to evaluate meat quality indicators including the pH of the muscle at 15 minutes post mortem and the percentage of water loss from the meat at 24 h post mortem (Pietrzak, et al., 1998).

RNA Preparation and PCR Amplification of cDNA. Total RNA was extracted from turkey breast muscle using Trizol reagent (Invitrogen, Carlsbad, Calif.). First strand cDNA was synthesized using SuperScript II RNase H Reverse Transcriptase (Invitrogen) following the manufacturer's protocols. Primers used in the reverse transcription and PCR were designed by using the CODEHOP program (Rose, et al., 1998). The sequence for the forward primer was 5'-CTG-CACCAGGAGGGCCACATGGACGA-3' [SEQ ID NO: 13] and for the reverse primer was 5'-CGGTCCAGTTTGCAC-CAGCCAGTCCAGG-3' [SEQ ID NO: 14]. The PCR amplification was conducted using Advantage cDNA polymerase (Clontech, Palo Alto, Calif.) and the first strand cDNA as template. The amplification consisted of an initial denaturation at 94° C. for 1 minute followed by 35 cycles of 94° C. for 20 sec, 63° C. for 20 sec and 68° C. for 1 min and a final extension at 68° C. for 5 minutes.

Isolation and PCR Amplification of Genomic DNA. Genomic DNA was isolated from turkey skeletal muscle using DNAzol (MRC, Cincinnati, Ohio) following the manufacturer's protocols. The standard PCR mix, in a final volume of 50 ul, consisted of 100-200 mg of template, 20 nM of primers, 500 uM dNTPs, 1× buffer 1 from the Expand Long Template PCR system (Roche, Indianapolis, Ind.) and 0.75 ul of enzyme mix provided as part of the system. The amplification consisted of an initial denaturation at 94° C. for 1 min followed by 35 cycles at 94° C. for 10 sec, 52° C. for 45 sec 68° C. for 3 min and a final extension at 68° C. for 7 min. Forward and reverse primers were designed based on the turkey aRYR cDNA sequence. The forward primer sequence was 5'-GACGCGTGTCGCTCAGCCGCTCGC-3' [SEQ ID NO: 15] and the reverse primer sequence was 5'-CCAG-CAGCTCATAGAGGAGGTTGACG-3' [SEQ ID NO: 16].

Cloning and Sequencing of Turkey aRYR. All PCR products were cloned into either pGEM T-Easy (Promega, Madison, Wis.) or pCC1 (Epicenter, Madison, Wis.) vectors following the manufacturer's protocols. Clones were screened, isolated and sequenced on both strands. Some clones were further digested into smaller fragments and subcloned into the pNEB193 vector (New England Biolabs, Beverly, Mass.) to facilitate sequencing.

Restriction Digestion and Hybridization. The insert carrying each aRYR allele was released from the cloning vector through restriction digestion and the insert was further digested with Bam HI and Pst I. The digested fragments were analyzed by agarose gel electrophoresis and transferred to nylon membranes (Nytran, Scleicher & Schuell, Keene, N.H.) for hybridization analysis. Two probes, E12 and E14, used in hybridization were designed based on the turkey aRYR cDNA sequence. These probes correspond to human RYR1 cDNA nucleotides number 1231 to 1348 and numbers 1568 to 1678, respectively. Probes were labeled with digoxigenin-11-dUTP and were detected with an anti-DIG antibody conjugated with alkaline phosphatase (Roche). The color development was conducted by using pre-mixed BCIP/NBT solution (Sigma, Saint Louis, Mo.).

Statistical Analysis. Least squares means of meat quality traits by genotype were compared using the mixed model procedure of SAS with a protected least significant difference test (Freud and Wilson, 1997).

EXAMPLE 1

Identification of aRYR Transcript Variants in Turkey. To test the hypothesis that mutations in turkey αRYR predispose turkeys to development of PSE meat, we began screening the region corresponding to the 3' end of mutation hot spot 1 of human RYRI. We identified three transcript variants spanning nucleotides number 1231-1947, corresponding to the human RYR1 cDNA sequence (accession no. Jo5200). The longest transcript (W) shared 70% and 60% amino acid sequence identity with mammalian RYR1 and bullfrog αRYR (Oyamada, et al., 1994), respectively (FIG. 1). Compared to turkey βRYR (our unpublished data) and chicken βRYR (Ottini, et al., 1996), the amino acid sequence identity was 66% and 58%, respectively. The other two transcript variants were characterized by the deletion of either 81-bp (variant AS-81; nucleotides number 1350-1430) or 193-bp (variant AS-193; nucleotides number 1350-1542) from the W transcript. The 81-bp deletion is predicted to result in a 27-amino acid deletion corresponding to $SER^{416}$-$SER^{443}$ of human RYR1. These 27 amino acid residues are highly conserved compared with mammalian RYR1, but are less conserved compared with bullfrog, fish and turkey αRYRs. The removal of 193-bp is predicted to lead to a frame-shift which would introduce a premature stop codon after amino acid residue 416. Thus, this transcript variant would not encode a complete functional channel protein. During analysis of the turkey αRYR cDNA sequence between bases 1231-1947, we did not observe any of the point mutations reported for human or porcine MH (Jurkat-Rott, et al., 2000).

EXAMPLE 2

Two aRYR Genomic DNA Alleles. We next addressed the question of whether the deletions in the aRYR cDNA sequence originate in the genome or were the result of alternative splicing. Upon analysis of the genomic DNA sequence in the region corresponding to W, AS-81 and AS-193, we identified two copies of αRYR from different birds using genomic DNA as template. These alleles differed in size by approximately 1 kb. We refer to these two copies of turkey αRYR genomic DNA as alleles αRYR-I and αRYR-II. Due to the size of the inserts and the abundance of tandem repeated sequences in the introns which made it difficult to design sequencing primers, each allele was digested to smaller fragments with restriction enzymes, subcloned and sequenced. This strategy allowed us to sequence approximately 90% of αRYR-I and 75% of αRYR-II including their complete exon sequences. The turkey αRYR genomic DNA sequence is still unknown; therefore, each intron and exon and exon/intron boundaries of both alleles were identified according to the corresponding intron and exon of the human RYR1 gene (Phillips, et al., 1996). The sequences of both turkey genomic DNA alleles analyzed in this study spanned from the last one-third of exon 12, intron 12, exon 13, intron 13 and to the end of exon 14. Splice junction boundaries agreed with the consensus sequences reported for splice donor sites (starting with GT) and splice acceptor sites (ending with TAG) (Shapiro and Senapathy, 1987).

Each allele was subjected to digestion by two different restriction enzymes, Bam HI and Pst I, and each allele showed a unique digestion pattern for both enzymes. In order to map the location of the restriction fragments, two different probes were used in Southern hybridization analysis. Based on the patterns of digestion and hybridization, we constructed a map for each allele (FIG. 2). According to the Pst I restriction digestion pattern, we estimated that the size of intron 12 in αRYR-II in approximately 1 kb longer than that in αRYR-I and that size of intron 13 in αRYR-I is approximately 100 bp longer than that in αRYR-II. However, sequence analysis showed that exons 12-14 in alleles αRYR-I and αRYR-II were identical.

Sequence comparison of turkey and human genomic DNA indicated that both turkey αRYR alleles were 3 nucleotides shorter than human RYRI in exon 13. The nucleotides numbers in exon 14 of both turkey alleles were the same as in human RYRI. However, the sizes of introns 12 and 13 in both turkey alleles were different from those observed in human RYRI.

EXAMPLE 3

Figure 3:
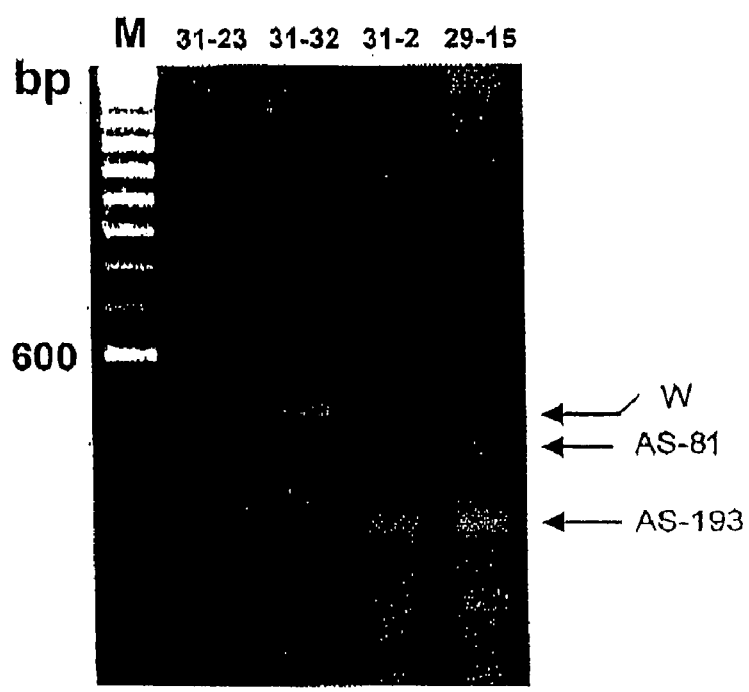
FIG. 3 shows Expression pattern of turkey αRYR transcript variants. αRYR cDNA samples corresponding to nucleotides 1231-1760 from individual birds were analyzed by RT-PCR and electrophoresis on a 1.5% agarose gel. The identification number of each bird is shown on the top of each lane in the gel. Three patterns of expression aer observed. Bird 31-23 shows expression of all three transcript variants; bird 31-32 shows expression of only W; bird 31-2 shoes expression of W and AS-193 and bird 29-15 shows expression of AS-81 and AS-193. M: 100 bp DNA ladder.

Expression of αRYR Transcript Variants. cDNA from turkeys (N=76) was screened by RT-PCR to study the expression patterns of the transcript variants. Most birds expressed all three transcript variants but there were birds that expressed W only, W with AS-193 but no AS-81 or AS-81 and AS-193 but no W (FIG. 3). These data were reproducible upon three screening experiments. We have not yet observed any birds expressing only AS-81 or AS-193 or W with AS-81. If birds expressed only AS-193, they probably could not survive because they would not have a functional α channel protein. The presence of a functional β channel does not rescue this deficiency (Airey, et al., 1993). Sequence analysis of both turkey αRYR alleles showed no evidence that the missing nucleotides in the cDNA sequence result from deletion of the analogous residues in the genomic DNA. Therefore, we concluded that the different transcript variants result form alternative splicing. Consistent with this conclusion was the identification in the 81-bp segment of three conserved sequence elements for the 3' splice site (Black, 2003). These include a special "A" residue followed by a polypyrimidine tract (TCCT), followed by a terminal CAG at the end of 81 bp (FIG. 4). When analyzed using a splice site prediction program (SpliceProximalCheck, EBI, UK), the 3' end of the 81-bp segment was recognized as a true acceptor site. Compared to the genomic DNA sequence, the three αRYR transcripts were characterized as: 1) the W transcript which carries a deletion of 81 bp located at the beginning of exon 13; 2) the AS-81 transcript which carries a deletion of 193 bp corresponding to the exon 13; 3) and the AS-193 transcript which carries a deletion of 193 bp corresponding to the exon 13. A schematic diagram of the locations of the alternative splicing sites in the turkey αRYR allele and the corresponding splice variants is shown in FIG. 4. The coexistence of W, AS-81 and AS-193 suggests that the use of splicing acceptor sites including the 3' end of intron 12 and 3' end of the 81 bp segment and the 3' end of intron 13 is not mutually exclusive even though they shared the same splice donor site at the 5' end of intron 12. In addition, to make AS-81 or AS-193, the splice acceptor site at the end of intron 12 is simply skipped and the splice acceptor site in exon 13 or at the end of intron 13 is used.

The physiological significance of the 27-amino acid deletion in the foot domain of turkey RYR is unknown. The deletion occurs within the cytoplasmic clamp domain which has been proposed to serve as part of the protein-protein contact site of RYR1 with the DHPR (Wu, et al., 1997); Baker, et al., 2002). Coupling of the DHPR and RYR in avian skeletal muscle controls the opening and closing of RYR during muscle contraction (O'Brien, et al., 1995). The deletion also occurs in a region which is highly sensitive to amino acid changes as indicated by the clustering of five mutations in this region in human MH (Jurkat-Rott, et al., 2000). Thus, the deletion in RYR may affect the interaction between the RYR and DHPR, which in turn could affect regulation of Ca-release.

It is not clear at this point whether AS-81 transcript variant of turkey RYR can only form homotetrameric channels or if formation of heterotetramers with the wild-type transcript is possible. A recent study showed that a RYR3 splice variant which had a 29-amino acid deletion of $His^{4406}$-$Lys^{4434}$ did not form a functional channel when expressed alone in HEK293 cells. However, when it was co-expressed with the wild type RYR3, it formed functional heterotetrameric channels with reduced caffeine sensitivity (Jiang, et al., 2003).

Several transcript variants have been reported in mammalian RYR1 and RYR3; this is the first report of avian RYR transcript variants. Most of the RYR1 or RYR3 transcript variants are characterized by the presence or absence of amino acid residues in either the modulatory or transmembrane domains in the C-terminal half of the protein (Zorzato, et al., 1994; Futatsugi, et al., 1995; Marziali, et al., 1996; Miyatake, et al., 1996; Tosso and Brenig, 1998; Jaing, et al., 2002). There are no previous reports of alternative spicing in the N-terminal domain of RYRI. The two splice regions of rabbit RYR3, located near the 5'-end and the middle, have been identified (Jiang, et al., 2003). Like the 193-bp deletion identified in the N-terminus of turkey αRYR in our study, the latter two splicing products were predicted to result in the synthesis of truncated RYR3 proteins.

EXAMPLE 4

Figure 5:
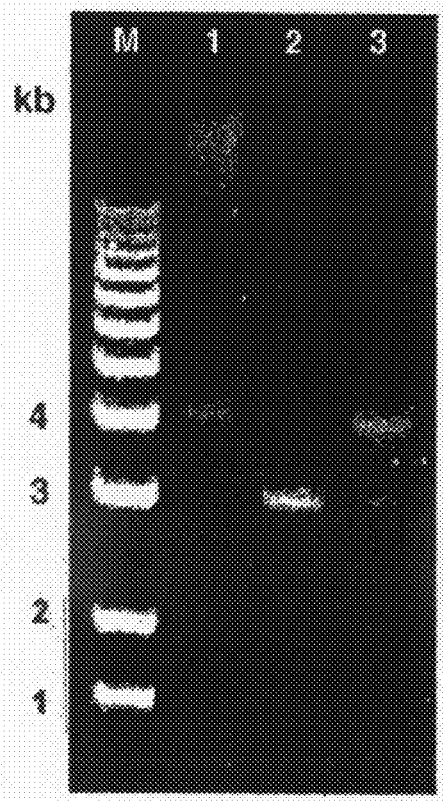
FIG. 5 shows turkey genotypes based on αRYR-I and αRYR-II alleles. Screening of genotypes was performed by PCR. PCR products were analyzed by electrophoresis on a 0.9% agarose gel. The results showed that turkeys could be grouped into three different genotypes: homozygous αRYR-II (lane 1), homozygous αRYR-I (lane 2) and heterozygous αRYR-I and αRYR-II (lane 3). M: 1 kb DNA ladder.

Distribution and Meat Quality Evaluation of Turkey αRYR Genotypes. Muscle samples from birds were randomly selected (N=35) from the RBC1 and Hybrid lines and screened by PCR to determine their genotypes. Based on the two αRYR alleles, turkeys could be grouped into three different genotypes: birds homozygous for αRYR-I, birds homozygous for αRYR-II and heterozygous birds carrying αRYR-I and αRYR-II alleles (FIG. 5). Based on the genotypes of turkey and the corresponding expression of the mRNA transcript variants, we concluded that birds expressing the transcripts with either 81-bp or 193-bp deletions were either homozygous for αRYR-I or αRYR-II or were heterozygous. This suggests that alternative splicing occurred in transcripts derived from both αRYR alleles. In addition, both homozygous genotypes were identified in random-bred and in growth-selected turkey populations. Homozygous αRYR-I was the most frequent genotype in our random-bred group (56%) whereas the frequencies of αRYR-I and αRYR-II in growth-selected group were approximately equal (47% vs. 41%). The heterozygous birds accounted for less than 12% in both populations. Each genotype was correlated with meat quality traits. PSE turkey meat is characterized by low early postmortem muscle pH and poor water holding capacity due to the denaturation of myosin (Pietrzak, et al., 1997). The 15-minute postmortem pH of muscle from the homozygous αRYR-II genotype (pH15+6.01±0.054, N=12) was significantly higher that the homozygous αRYR-I genotype (pH15=5.80±0.043, N=19; P<0.01). The percentage of exudate between the two homozygous genotypes was not significantly different. However, there appeared to be an association between the αRYR-II genotype and improved water-holding capacity (% exudate+0.53±0.1 for αRYR-II and 0.79±0.08 for αRYR-I genotypes respectively; P+0.056). Because only four heterozygous birds were identified, the statistical analysis was not performed for these birds.

There was no significant relationship between the presence of the alternative splice transcript variants and meat quality. However, we did not quantify the expression of transcript variant. It is possible that environmental factors such as heat stress could alter the ratio of splice variants. Our results suggest that turkeys homozygous for αRYR-I are more likely to develop PSE meat under standard growth and slaughter processes. Additionally, our results show that turkeys homozygous for the αRYR-II genotype exhibited a significantly higher postmortem muscle pH and a better water-holding capacity than the αRYR-I genotype. That is, they showed a significant reduction of PSE meat symptoms.

From the foregoing, it should be obvious that the present invention provides for methods for the selection of turkeys having reduced symptoms of PSE-meat production.

What is claimed is:

1. A method of genotyping turkeys, comprising:
   a) providing i) a forward primer and a reverse primer, wherein the sequence of said forward primer is SEQ ID NO:15 and wherein the sequence of said reverse primer is SEQ ID NO:16; and ii) genomic nucleic acid samples from a plurality of turkeys;
   b) amplifying said genomic nucleic acid samples with said primers so as to generate amplified products; and
   c) visualizing said amplified products on a gel to genotype said plurality of turkeys.

2. The method of claim 1, further comprising d) identifying amplified product consisting of a single band approximately 4 kilobases.

3. The method of claim 1, wherein said nucleic acid samples are obtained from muscle tissue.

4. The method of claim 3, wherein said muscle tissue is turkey breast muscle.

5. The method of claim 1, wherein said samples are taken from slaughtered turkeys.

6. The method of claim 1, wherein said samples are taken from live turkeys.

7. The method of claim 6, wherein said live turkeys identified as generating amplified product consisting of a single band of approximately 4 kilobases are used for breeding.

8. The method of claim 6, wherein said live turkeys are young turkeys.

9. The method of claim 8, wherein said live young turkeys identified as generating amplified product consisting of a single band of approximately 4 kilobases are subsequently grown to maturity.

10. The method of claim 6, wherein said live turkeys are mature turkeys.

11. The method of claim 10, wherein said live mature turkeys identified as generating amplified product consisting of a single band of approximately 4 kilobases are slaughtered for commercial meat production.

12. A method of selecting turkeys for meat production based on genotyping, comprising:
   a) providing i) a forward primer and a reverse primer, wherein the sequence of said forward primer is set forth in SEQ ID NO:15 and wherein the sequence of said reverse primer is set forth in SEQ ID NO:16; and ii) genomic nucleic acid samples from a plurality of live turkeys;
   b) amplifying said genomic nucleic acid samples with said primers to generate amplified products under conditions such that turkeys with an amplified product consisting of a single band approximately 4 kilobases are identified;
   c) selecting said live turkeys identified as in step b) for meat production.

13. The method of claim 12, wherein said nucleic acid samples are obtained from muscle tissue.

14. The method of claim 13, wherein said muscle tissue is turkey breast muscle.

15. The method of claim 12, wherein said selecting for meat production comprises slaughtering said selected turkeys.

16. The method of claim 12, wherein said selecting for meat production comprises utilizing said turkeys identified as in step b) for breeding.

17. The method of claim 12, wherein said live turkeys are young turkeys.

18. The method of claim 17, wherein said selecting for meat production comprises growing said turkeys identified as in step b) to maturity.

19. The method of claim 12, wherein said turkeys not identified as in step b) are not used for meat production.

* * * * *